United States Patent
Yao et al.

(10) Patent No.: US 12,157,778 B2
(45) Date of Patent: Dec. 3, 2024

(54) PEPTIDES FOR ACTIVATION OF CELL SIGNALING IN OSTEOPROGENITOR CELLS

(71) Applicant: The Regents of the University of California, Oakland, CA (US)

(72) Inventors: Wei Yao, El Dorado Hills, CA (US); Ruiwu Liu, Sacramento, CA (US); Kit S. Lam, Davis, CA (US); Wenwu Xiao, Sacramento, CA (US); Nancy Lane, Hillsborough, CA (US)

(73) Assignee: The Regents of the University of California, Oakland, CA (US)

( * ) Notice: Subject to any disclaimer, the term of this patent is extended or adjusted under 35 U.S.C. 154(b) by 850 days.

(21) Appl. No.: 17/146,009

(22) Filed: Jan. 11, 2021

(65) Prior Publication Data

US 2021/0395302 A1 Dec. 23, 2021

Related U.S. Application Data

(63) Continuation of application No. PCT/US2019/042660, filed on Jul. 19, 2019.

(60) Provisional application No. 62/700,743, filed on Jul. 19, 2018.

(51) Int. Cl.
| | |
|---|---|
| *A61K 38/07* | (2006.01) |
| *A61K 31/663* | (2006.01) |
| *A61K 47/64* | (2017.01) |
| *A61P 19/10* | (2006.01) |
| *C07K 5/103* | (2006.01) |

(52) U.S. Cl.
CPC ............ *C07K 5/101* (2013.01); *A61K 31/663* (2013.01); *A61K 47/64* (2017.08); *A61P 19/10* (2018.01)

(58) Field of Classification Search
None
See application file for complete search history.

(56) References Cited

U.S. PATENT DOCUMENTS

| | | | |
|---|---|---|---|
| 7,576,175 | B2 | 8/2009 | Lam et al. |
| 9,119,884 | B2 | 9/2015 | Lam et al. |
| 9,561,256 | B2 * | 2/2017 | Lam ........................ C07K 5/101 |
| 2010/0233161 | A1 | 9/2010 | Koltermann |

FOREIGN PATENT DOCUMENTS

WO  2013/032527 A1  3/2013

OTHER PUBLICATIONS

Extended European Search Report mailed on Mar. 18, 2022 for EP Application No. 19837646.9, 10 pages.
PCT/US2019/042660, International Search Report and Written Opinion, Oct. 7, 2019, 9 pages.

* cited by examiner

*Primary Examiner* — Fred H Reynolds
(74) *Attorney, Agent, or Firm* — Kilpatrick Townsend and Stockton LLP

(57) ABSTRACT

The present invention provides compounds and pharmaceutical compositions of peptidomimetic ligands. The peptidomimetic ligands can be conjugated with phosphonate drugs. The compounds and pharmaceutical compositions of the present invention are useful in the treatment of osteoporosis and for the promotion of bone growth due to their specificity for the $\alpha_4\beta_1$ integrin on mesenchymal stem cells and for the surface of bone.

7 Claims, 24 Drawing Sheets

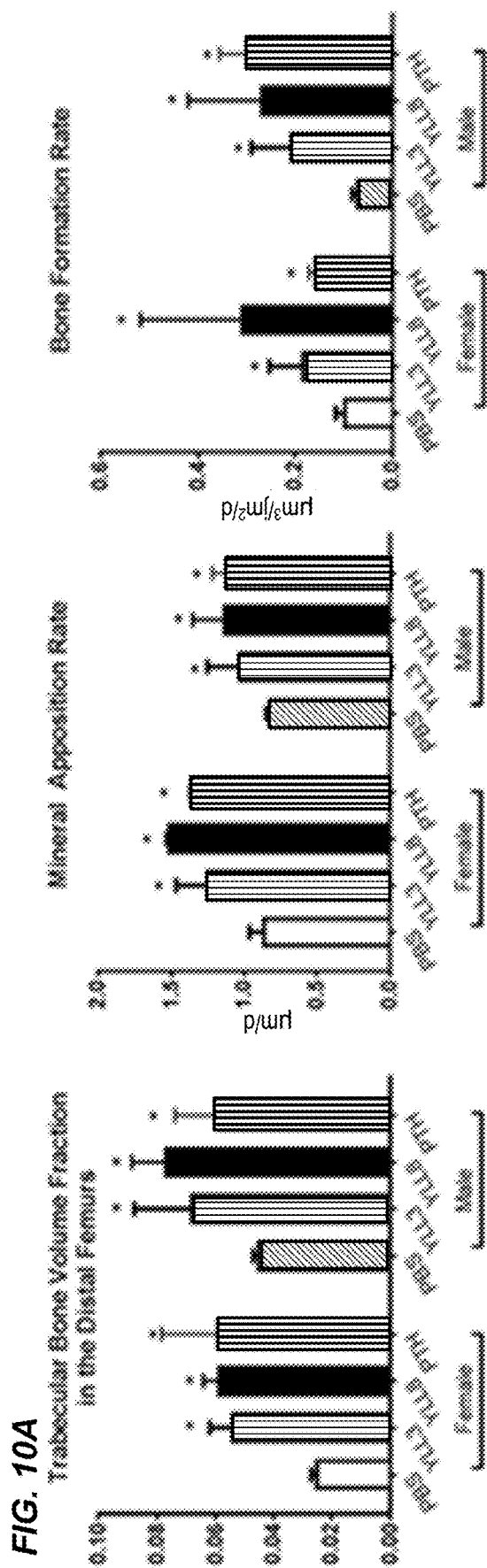

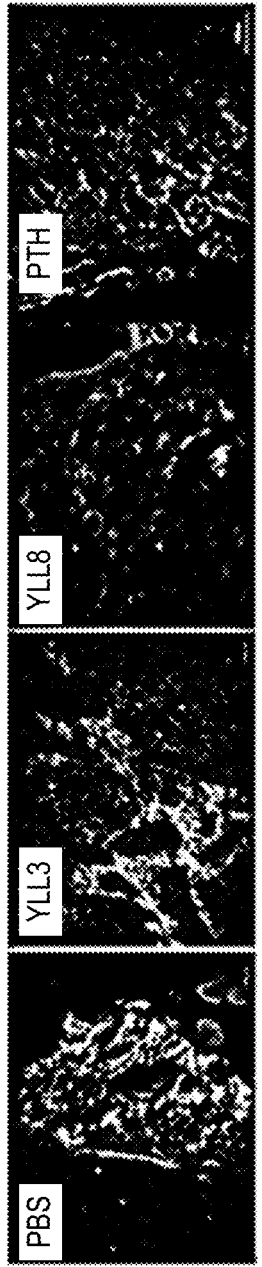
FIG. 13A
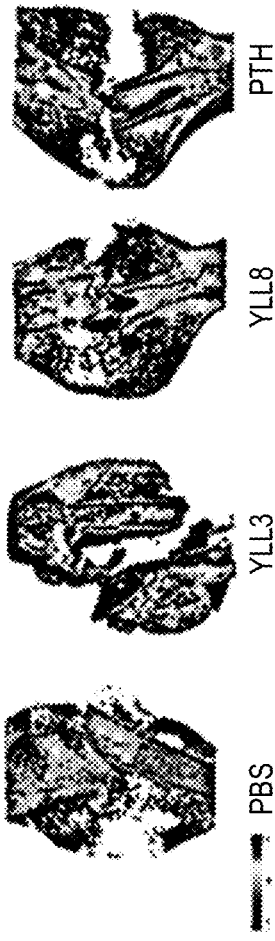
FIG. 13B
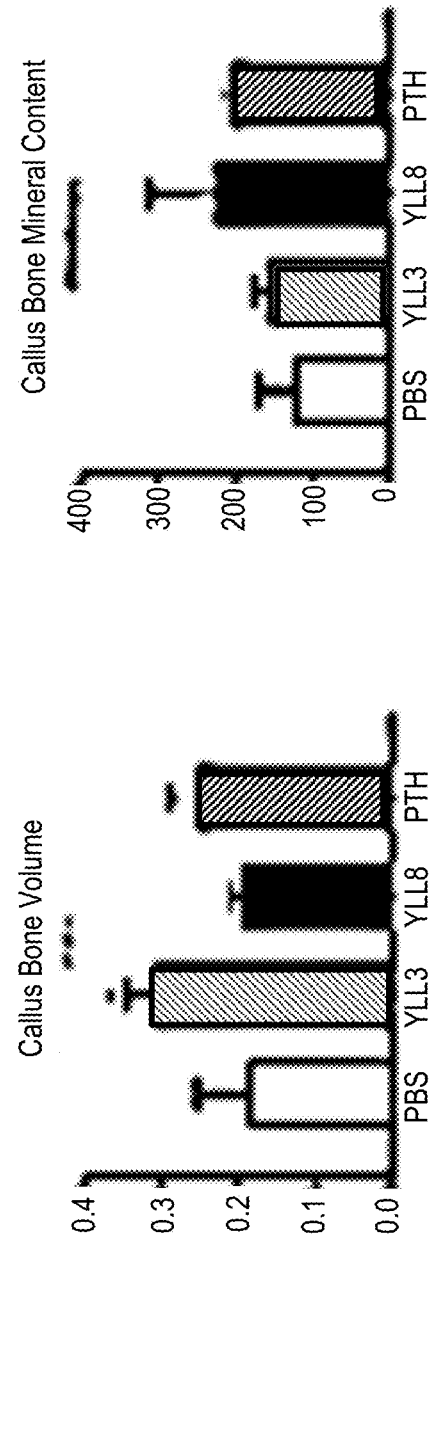

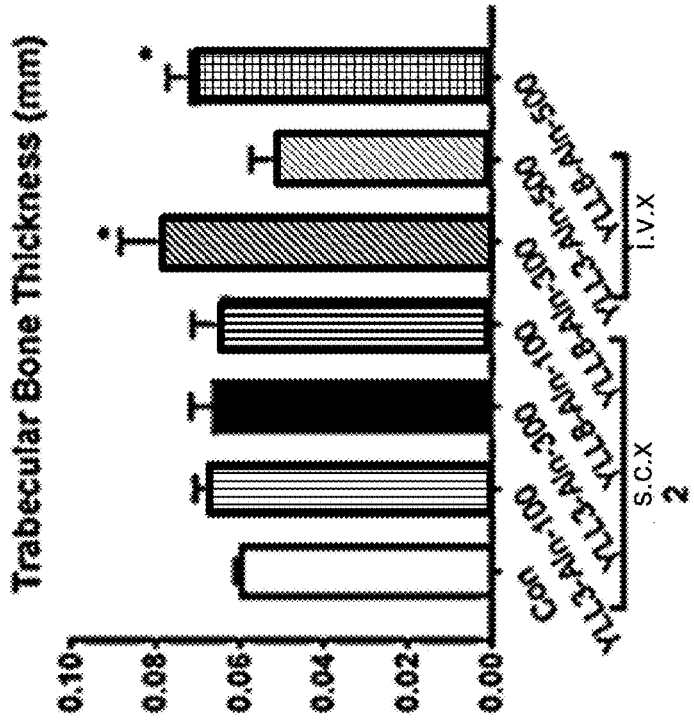
FIG. 15A
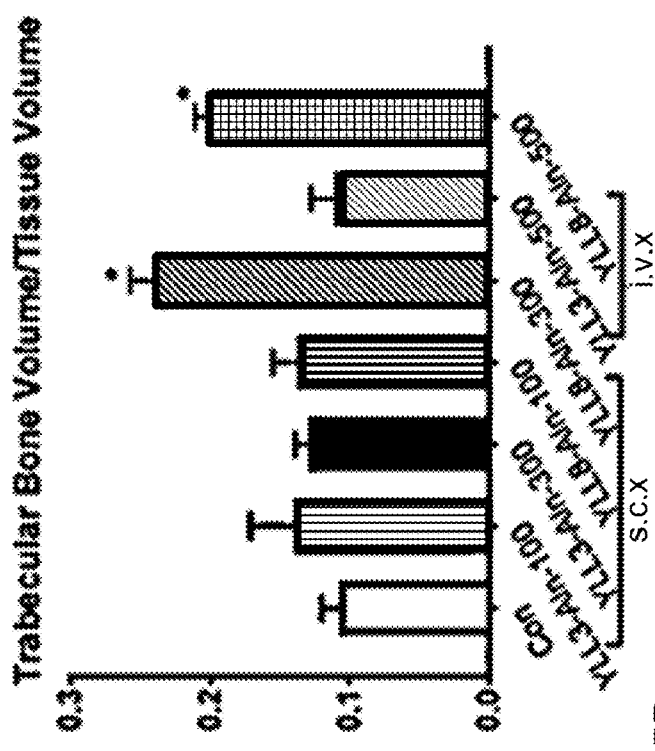
FIG. 15B
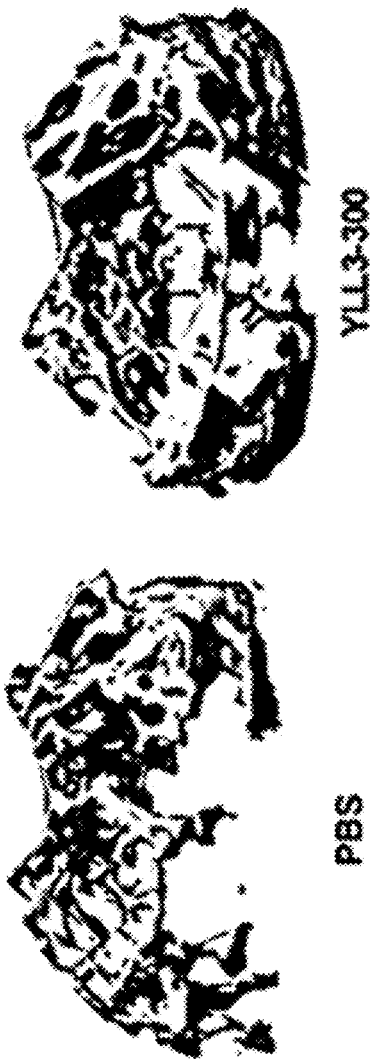

PEPTIDES FOR ACTIVATION OF CELL SIGNALING IN OSTEOPROGENITOR CELLS

CROSS-REFERENCES TO RELATED APPLICATIONS

The present application is a continuation of International Appl. No. PCT/US2019/042660, filed Jul. 19, 2019, which claims the benefit of U.S. Provisional Appl. No. 62/700,743 filed Jul. 19, 2018, the full disclosure which are incorporated herein by reference in their entirety for all purposes.

STATEMENT AS TO RIGHTS TO INVENTIONS MADE UNDER FEDERALLY SPONSORED RESEARCH AND DEVELOPMENT

This invention was made with government support under Grant No. AR061366 awarded by the National Institutes of Health. The government has certain rights in the invention.

BACKGROUND OF THE INVENTION

Osteoporosis is a disease of increased bone fragility that results from estrogen deficiency and aging. It is a major public health problem with nearly 50% of Caucasian women and 25% of Caucasian men at risk for an osteoporotic fracture in their lifetimes (Publication from National Osteoporosis Foundation). Furthermore, over 2 million osteoporotic fractures occur annually in the US, with 27% vertebra and 14% hip fractures. Accordingly, osteoporosis represents a significant health concern, especially with the aging segment of our population growing rapidly worldwide.

Aging is associated with a reduction in bone marrow skeletal osteoprogenitor cells and the proper microenvironment to support these osteoprogenitors to differentiate into osteoblasts to form bone. This decrease in the number of mesenchymal stem cells (MSCs) in the bone marrow with aging leads to reduced osteogenesis and may be the most important factor responsible for reduced bone formation and increase bone fragility (Heersche, J. N., C. G. Bellows, and Y. Ishida, *J Prosthet Dent*, 1998, 79(1): p. 14-6; Ettinger, M. P., *Arch Intern Med*, 2003. 163(18): p. 2237-46). Currently, nearly all of the treatments for osteoporosis reduce bone loss by decreasing osteoclastic bone resorption and thereby preventing the further breakdown of bone. Importantly, this class of antiresorptive drugs does not restore the lost bone structure. Current medications that enhance bone formation include hPTH (1-34) (Teriparatide), PTHrp (Abaloparatide), and Evenity (Romosozumab), and are approved by the FDA for the treatment of osteoporosis. Abaloparatide may be more potent than Teriparatide and has a more rapid onset of fracture reduction than Teriparatide with uncoupling of bone remodeling. Treatments with Teriparatide and Abaloparatide are limited to 2 years with a boxed warning of risk for osteosarcomas being observed in preclinical studies. Both Teriparatide and Abaloparatide are not recommended for patients with a higher risk for osteosarcoma, a history of irradiation, primary hyperparathyroidism, and any form of the secondary hyperparathyroidism. Moreover, all the current pharmacologic agents reduce the risk of vertebral fractures by about 50% or higher, but their efforts on hip fracture reduction remain low.

Therapeutic modalities that target bone formation by either increasing the number and or the activity of osteoblasts may be a more attractive approach for enhancing bone formation and promoting bone regeneration. Although bone regeneration by induction of osteogenesis from MSCs is a rational strategy to treat osteoporosis, systemic infusions of MSCs in vivo has failed to promote an osteogenic response in bone due to the inability of MSCs to migrate to the bone surface which is a major clinical problem for MSC transplantation (Gao, J., et al., *Cells Tissues Organs*, 2001. 169(1): p. 12-20; Meyerrose, T. E., et al., *Stem Cells*, 2007, 25(1): p. 220-7). In addition, engraftment of the MSCs requires donor ablation using chemotherapy and/or radiation which may result in concomitant damage to endogenous mesenchymal cells (Bacigalupo, A., *Best Pract Res Clin Haematol*, 2004, 17(3): p. 387-99).

Cell adhesion is a process by which cells associate with each other, migrate towards a specific target, or localize within the extracellular matrix. Cell adhesion constitutes one of the fundamental mechanisms underlying numerous biological phenomena. Investigations into the molecular basis for cell adhesion have revealed that various cell surface macromolecules, collectively known as cell adhesion molecules or receptors, mediate cell-cell and cell-matrix interactions. For example, members of the integrin family of cell surface receptors mediate cell-cell and cell-matrix interactions and regulate cell motility, migration, survival, and proliferation (Hynes, *Cell*, 69: 11-25 (1992); Hynes, *Cell*, 1110:673-687 (2002)). Integrins are non-covalent heterodimeric complexes consisting of two subunits, $\alpha$ and $\beta$. There are at least 18 different $\alpha$ subunits and at least 8 different $\beta$ subunits.

Mesenchymal stem cells within the bone marrow have a multi-lineage potential and represent a mixture of precursors for mesenchymal-derived cell types including osteoblasts, chondrocytes and adipocytes (Owen, M. et al., *Ciba Found Symp*, 1988, 136: p. 42-60; Bruder, S. P., et al., *J Cell Biochem*, 1994, 56(3): p. 283-94; Prockop, D. J., *Science*, 1997, 276(5309): p. 71-4). Bone cells at all maturation stages rely heavily on cell-matrix and cell-cell interactions (Mukherjee, S., et al., *J Clin Invest*, 2008, 118(2): p. 491-504; Grzesik, W. J. and P. G. Robey, *J Bone Miner Res*, 1994, 9(4): p. 487-96; Vukicevic, S., et al., *Cell*, 1990, 63(2): p. 437-45; Mbalaviele, G., et al., *J Bone Miner Res*, 2006, 21(12): p. 1821-7). Bone marrow is the site where the committed osteoblast progenitors reside, and the osteogenic differentiation is the default pathway for MSC lineage commitment (Halleux, C., et al., *J Musculoskelet Neuronal Interact*, 2001, 2(1): p. 71-6; Muraglia, A., et al., *J Cell Sci*, 2000, 113 (Pt 7): p. 1161-6). Mobilization of the osteoblastic progenitors to the bone surface is a critical step for the osteoblasts to mature and form mineralized tissue (Adams, G. B., et al., *Nature*, 2006, 439(7076): p. 599-603; Chen, X. D., et al., *J Bone Miner Res*, 2007, 22(12): p. 1943-56). Once the osteoblastic progenitors are "directed" to the bone surface, they synthesize a range of proteins including osteocalcin, osteopontin, bone sialoprotein, osteonectin, collagen-I and fibronectin that will further enhance the adhesion and maturation of osteoblasts (Gronthos, S., et al., *Periodontol 2000*, 2006, 41: p. 188-95; Gronthos, S., et al., *Bone*, 2001, 28(2): p. 174-81; Gronthos, S., et al., *J Bone Miner Res*, 1997, 12(8): p. 1189-97). These interactions are largely mediated by transmembrane integrin receptors that primarily utilize an arginine-glycine-aspartate (RGD) sequence to identify and bind to specific ligands. MSCs express integrins $\alpha$1, 2, 3, 4, 6, 11, CD51 (integrin $\alpha$V), and CD29 (integrins $\beta$1) (Brooke, G., et al., *Stem Cells Dev*, 2008). Integrins $\alpha_1\beta_1$, $\alpha_2\beta_1$, $\alpha_v\beta_1$, $\alpha_v\beta_5$, $\alpha_5\beta_1$ and $\alpha_4\beta_1$ are reported to be expressed in the osteoblastic cells (Grzesik, W. J. and Robey, P. G., *J Bone Miner Res*, 1994, 9(4): p. 487-96; Gronthos, S., et al., *Bone*, 2001, 28(2): p. 174-81; Gronthos, S., et al., *J*

Bone Miner Res, 1997. 12(8): p. 1189-97; Cowles, E. A., L. L. Brailey, and G. A. Gronowicz, *J Biomed Mater Res*, 2000, 52(4): p. 725-37). Overexpression of $\alpha_4$ Integrin on MSCs has been reported to increase homing of the MSCs to bone (Mukherjee, S., et al., *J Clin Invest*, 2008, 118(2): p. 491-504).

Bisphosphonates are widely used for the treatment of osteoporosis. This class of drugs is also used as a "vehicle" for delivering bone-targeted drugs to osseous tissue as prodrugs based on their bisphosphonate moiety. Bisphosphonates have been used to deliver sustained release diclofenac, a non-steroidal anti-inflammatory drug to bone in rats (Hirabayashi, H., et al., *J Control Release*, 2001, 70(1-2): p. 183-91). The bisphosphonate dose needed for this drug-delivery purpose is usually 10-100 fold lower than the doses needed for the treatments of osteoporosis, hypocalcaemia, Paget's disease or metastatic bone cancer.

It is well-understood that bone formation is beneficial for the treatment of a wide variety of disparate disorders in mammals including simple aging, bone degeneration and osteoporosis, fracture healing, fusion or arthrodesis, osteogenesis imperfecta, etc., as well as for successful installation of various medical orthopedic and periodontal implants such as screws, rods, titanium cage for spinal fusion, hip joints, knee joint, ankle joints, shoulder joints, dental plates and rods, etc.

Increasing bone mineralization to treat conditions characterized at least in part by increased bone resorption, such as osteopenia, bone fractures, osteoporosis, arthritis, tumor metastases, Paget's disease and other metabolic bone disorders, using cathepsin K inhibitors and TGF-beta binding proteins, etc., are well-known as shown by U.S. Publication No. 2004/0235728 to Selwyn Aubrey Stoch, published Nov. 25, 2004, and Mary E. Brunkow et al., U.S. Pat. No. 6,489,445 and U.S. Publication No. 2004/0009535, published Jan. 15, 2004. In the Brunkow '445 patent and '535 publication, the TGF-beta binding proteins include Sost polypeptide (full length and short peptide) antibodies that interfere with the interaction between the TGF-beta binding protein sclerostin and a TGF-beta superfamily member, and in particular a bone morphogenic protein. In the Brunkow '445 patent a novel family of human TGF-beta binding proteins and nucleic acids encoding them are recited. The protein binds to at least human bone morphogenic protein-5 and human bone morphogenic protein-6. The aforementioned diseases are due to a systemic loss of bone mineral and thus the administration of the antibody therapeutic is for the systemic (whole body) increase in bone mineral density.

U.S. Publication No. 2006/0165799, published Jul. 27, 2006, teaches a bone-filling composition for stimulating bone-formation and bone-consolidation comprising biocompatible calcium sulfate and viscous biopolymers. The composition is intended to be administered into the missing part of injured bone without diffusing to surrounding organs.

U.S. Publication No. 2005/025604, published Nov. 17, 2005, shows induction of bone formation by mechanically inducing an increase in osteoblast activity and elevating systemic blood concentration of a bone anabolic agent, including optionally elevating systemic blood concentration of an antiresorptive agent.

U.S. Pat. No. 7,576,175, issued Aug. 18, 2009, shows $\alpha_4\beta_1$ integrin ligands that display high binding affinity, specificity, and stability. The ligands comprise a peptide having "n" independently selected amino acids, wherein at least one amino acid is an unnatural amino acid or a D-amino acid, and wherein n is an integer of from 3 to 20.

U.S. Publication No. 2010/0021379, published Jan. 28, 2010, shows antibody conjugates comprising a targeting agent covalently attached to an antibody or fragment thereof. The targeting agent includes a ligand comprising a peptide or peptidomimetic specific for an integrin receptor such as the $\alpha_4\beta_1$ integrin.

What is needed in the art is new compositions and methods for treating osteoporosis and promoting bone growth.

BRIEF SUMMARY OF THE INVENTION

In one embodiment, the invention provides a compound according to Formula I:

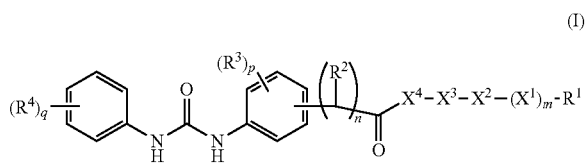

or a pharmaceutically acceptable salt thereof,
wherein:
$R^1$ is selected from the group consisting of —OH, —NH$_2$, and -L-D;
$R^2$ is selected from the group consisting of H, $C_{1-6}$ alkyl, and $C_{3-8}$ cycloalkyl;
each $R^3$ and $R^4$ is independently selected from the group consisting of H, halogen, $C_{1-6}$ alkyl, $C_{1-6}$ alkoxy, and $C_{1-6}$ haloalkyl;
$X^1$, $X^2$, and $X^3$ are independently-selected amino acid residues;
$X^4$ is selected from the group consisting of an ($N^6$-modified)lysine residue, a citrulline residue, a homocitrulline residue, a leucine residue, an (N-methyl)leucine residue, an isoleucine residue, an (N-methyl) isoleucine residue, and a homophenylalanine residue;
L is a linker;
D is a phosphonate drug; and
subscripts m, n, p, and q are each independently an integer from 0 to 4.

In another embodiment, the invention provides a pharmaceutical composition containing a compound as described herein, or a pharmaceutically acceptable salt thereof, and one or more pharmaceutically acceptable excipients.

In another embodiment, the invention provides a method of treating osteoporosis. The method includes administering to a subject in need thereof a therapeutically effective amount of a compound, or a pharmaceutically acceptable salt thereof, or a pharmaceutical composition containing a therapeutically effective amount of a compound, or a pharmaceutically acceptable salt thereof as described herein.

In another embodiment, the invention provides a method of promoting bone growth. The method includes administering to a subject in need thereof a therapeutically effective amount of a compound, or a pharmaceutically acceptable salt thereof, or a pharmaceutical composition containing a therapeutically effective amount of a compound, or a pharmaceutically acceptable salt thereof as described herein.

In another embodiment, the invention provides a method of treating low bone mass. The method includes administering to a subject in need thereof a therapeutically effective amount of a compound, or a pharmaceutically acceptable salt thereof, or a pharmaceutical composition containing a therapeutically effective amount of a compound, or a pharmaceutically acceptable salt thereof as described herein.

In another embodiment, the invention provides a method of treating a disease or condition characterized by secondary low bone mass. The method includes administering to a subject in need thereof a therapeutically effective amount of a compound, or a pharmaceutically acceptable salt thereof, or a pharmaceutical composition containing a therapeutically effective amount of a compound, or a pharmaceutically acceptable salt thereof as described herein.

BRIEF DESCRIPTION OF THE DRAWINGS

FIG. 6A shows the quantitative measurement of Alkaline Phosphatase (ALP) at day 10 or alizarin red (AR) levels at day 21 of the YLL3 and YLL8 beads. FIG. 6B shows representative images of ALP staining in BMSCs cultured with beads displaying YLL3 or YLL8 at day 10. FIG. 6C shows representative images of AR staining in BMSCs cultured with beads displaying YLL3 or YLL8 at day 21. FIG. 6D shows results of BMSCs that were cultured with YLL3 and YLL8 peptides at 6×10-8 M in osteogenic media for 10 or 21 days to measure ALP levels at day 10, and AR levels at day 21. *, p<0.05 vs. Con.

FIG. 7A is a layout of an Akt signaling array. FIG. 7B shows BMSCs that were cultured with peptides or hPTH (1-34) at $6 \times 10^{-8}$ M in osteogenic medium for three days, and then the Akt array was performed using cell lysates. FIG. 7C shows quantitative pixel density from selected wells in FIG. 7B.

FIG. 9D shows representative images of trabecular bone samples taken from male mice and FIG. 9E shows representative images of cortical bone samples taken from male mice. *, p<0.05 vs. PBS.

FIGS. 10A-10D show the effects of YLL8 on bone formation in vivo. Four-month-old female and male mice were treated with PBS control, YLL8 at 5 µg/kg (~6×10$^{-9}$M) or PTH at 25 µg/kg, sc., 5×/week for 21 days (n=4-6/group). All mice received Alizarin red and Calcein at −7 and −2 days before euthanization. FIG. 10A shows trabecular bone volume and surface-based bone formation measured in the distal femur metaphysis (DFM). FIG. 10B shows representative images of the DFM trabecular region in female mice. FIG. 10C shows representative images of the DFM trabecular region in male mice. FIG. 10D shows cortical bone mass measured at the mid-femurs by micro CT; bone strength was obtained by three-point bending of the femurs. *, p<0.05 vs. PBS.

FIGS. 13A-13D show callus mineralization in fracture healing using YLL3. Female Prx1-GFP/ERT mice were fractured at two months of age and received tamoxifen at 10 mg/kg for three days. YLL3 or YLL8 were given at 10 µg/kg, and hPTH (1-34) was given at 50 µg/kg, s.c., 5×/week for 10 or 21 days. Alizarin red was given at −1 day before authorization. FIG. 13A shows representative fractured femur images from a Prx1-GFP/ERT mouse at day 10. FIG. 13B shows representative callus images from the outer edge of the callus in indicated treatment groups at day 10 post fracture and representative micro CT thickness mapping of the callus, callus bone volume, and bone mineral content from indicated treatment groups at day 10 post-fracture. FIG. 13C shows representative fractured femur images from a Prx1-GFP/ERT mouse at day 21. FIG. 13D shows representative callus images from the outer edge of the callus in indicated treatment groups at 21 days post-fracture and representative micro CT thickness mapping of the callus, callus bone volume, and bone mineral content from indicated treatment groups at day 21 post-fracture.

FIGS. 15A-15C show two-month-old female mice treated with PBS control; YLL3-Aln or YLL8-Aln at 100 m/kg or 300 m/kg, subcutaneously, once every two weeks for 2 doses; or YLL3-Aln or YLL8-Aln at 500 m/kg, one IV dose. Mice were euthanized at 28 days (n=4-5/group). FIG. 15A shows quantitative trabecular bone volume and trabecular bone thickness. FIG. 15B shows representative 3D images of the trabecular region taken from the distal femurs in indicated treatment groups. FIG. 15C shows middle femoral cortical bone volume and cortical bone thickness measured in femurs by micro CT representative images of the middle femoral cortex in indicated treatment groups. *, p<0.05 vs. PBS.

DETAILED DESCRIPTION OF THE INVENTION

Figure 1:
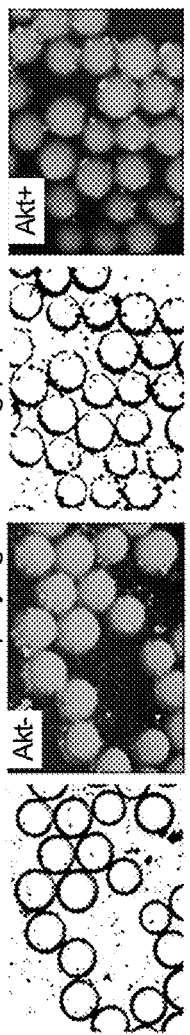
FIG. 1 shows the flow chart for screening cell signaling activators that have affinity for osterix+ osteoprogenitor cells.
Figure 1:
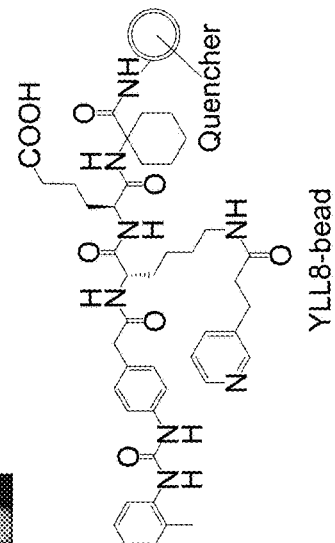
Figure 1:
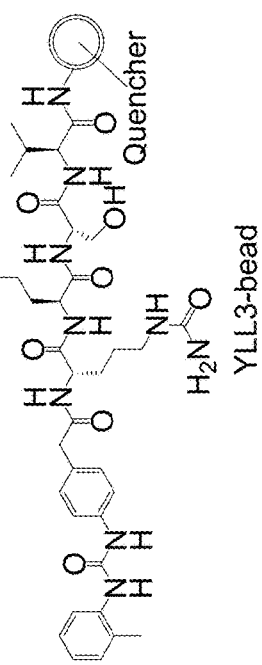

The present invention provides peptidomimetic ligand compounds, pharmaceutical compositions containing the compounds, and methods of using the compounds. The peptidomimetic ligands can also be conjugated with phosphonate drugs, such as alendronate. The compounds and pharmaceutical compositions of the present invention are useful for promoting bone growth, the treatment of osteoporosis, the treatment of low bone mass, and the treatment a disease or condition characterized by secondary low bone mass due to their ability to activate Akt signaling.

I. DEFINITIONS

The abbreviations used herein have their conventional meaning within the chemical and biological arts.

As used herein, the terms "Ale," "Aln" or "Alen" refer to Alendronate.

Where substituent groups are specified by their conventional chemical formulae, written from left to right, they equally encompass the chemically identical substituents that would result from writing the structure from right to left, e.g., —CH$_2$O— is equivalent to —OCH$_2$—.

As used herein, the terms "halo" or "halogen," by themselves or as part of another substituent, mean, unless otherwise stated, a fluorine, chlorine, bromine, or iodine atom.

As used herein, the term "alkyl" refers to a straight or branched, saturated, aliphatic radical having the number of carbon atoms indicated. For example, $C_1$-$C_6$ alkyl includes, but is not limited to, methyl, ethyl, propyl, butyl, pentyl, hexyl, iso-propyl, iso-butyl, sec-butyl, tert-butyl, etc.

As used herein, the term "haloalkyl" refers to alkyl as defined above where some or all of the hydrogen atoms are substituted with halogen atoms. For example, haloalkyl includes trifluoromethyl, fluoromethyl, 1,2,3,4,5-pentafluoro-phenyl, etc. The term "perfluoro" defines a compound or radical which has at least two available hydrogens substituted with fluorine. For example, perfluorophenyl refers to 1,2,3,4,5-pentafluorophenyl, perfluoromethane refers to 1,1,1-trifluoromethyl, and perfluoromethoxy refers to 1,1,1-trifluoromethoxy.

As used herein, the term "heteroalkyl" refers to an alkyl group having from 1 to 3 heteroatoms such as N, O and S. Additional heteroatoms can also be useful, including, but not limited to B, Al, Si and P. The heteroatoms can also be oxidized, such as, but not limited to, —S(O)— and —S(O)$_2$—. For example, heteroalkyl can include ethers, thioethers, alkyl-amines and alkyl-thiols.

As used herein, the term "alkoxy" refers to alkyl with the inclusion of an oxygen atom, for example, methoxy, ethoxy, etc.

As used herein, the term "aryl" refers to a monocyclic or fused bicyclic, tricyclic or greater, aromatic ring assembly containing 6 to 16 ring carbon atoms. For example, aryl may be phenyl, benzyl or naphthyl, preferably phenyl. "Arylene" means a divalent radical derived from an aryl group. Aryl groups can be mono-, di- or tri-substituted by one, two or three radicals selected from alkyl, alkoxy, aryl, hydroxy, halogen, cyano, amino, amino-alkyl, trifluoromethyl, alkylenedioxy and oxy-$C_2$-$C_3$-alkylene; all of which are optionally further substituted, for instance as hereinbefore defined; or 1- or 2-naphthyl; or 1- or 2-phenanthrenyl.

Alkylenedioxy is a divalent substitute attached to two adjacent carbon atoms of phenyl, e.g. methylenedioxy or ethylenedioxy. Oxy-$C_2$-$C_3$-alkylene is also a divalent substituent attached to two adjacent carbon atoms of phenyl, e.g. oxyethylene or oxypropylene. An example for oxy-$C_2$-$C_3$-alkylene-phenyl is 2,3-dihydrobenzofuran-5-yl.

As used herein, the term "heteroaryl" refers to a monocyclic or fused bicyclic or tricyclic aromatic ring assembly containing 5 to 16 ring atoms, where from 1 to 4 of the ring atoms are a heteroatom. For example, heteroaryl includes pyridyl, indolyl, indazolyl, quinoxalinyl, quinolinyl, isoquinolinyl, benzothienyl, benzofuranyl, furanyl, pyrrolyl, thiazolyl, benzothiazolyl, oxazolyl, isoxazolyl, triazolyl, tetrazolyl, pyrazolyl, imidazolyl, thienyl, or any other radicals substituted, especially mono- or di-substituted, by e.g. alkyl, nitro or halogen. Pyridyl represents 2-, 3- or 4-pyridyl, advantageously 2- or 3-pyridyl. Thienyl represents 2- or 3-thienyl. Quinolinyl represents preferably 2-, 3- or 4-quinolinyl. Isoquinolinyl represents preferably 1-, 3- or 4-isoquinolinyl. Benzopyranyl, benzothiopyranyl represents preferably 3-benzopyranyl or 3-benzothiopyranyl, respectively. Thiazolyl represents preferably 2- or 4-thiazolyl, and most preferred, 4-thiazolyl. Triazolyl is preferably 1-, 2- or 5-(1,2,4-triazolyl). Tetrazolyl is preferably 5-tetrazolyl.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', —NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro($C_1$-$C_4$)alkoxy, and perfluoro($C_1$-$C_4$)alkyl, in a number ranging from zero to the total number of open valences on the aromatic ring system; and where R', R" and R'" are independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl.

As used herein, the term "cycloalkyl" refers to a saturated or partially unsaturated, monocyclic, fused bicyclic or bridged polycyclic ring assembly containing from 3 to 12 ring atoms, or the number of atoms indicated. For example, $C_{3-8}$cycloalkyl includes cyclopropyl, cyclobutyl, cyclopentyl, cyclohexyl, and up to cyclooctyl.

As used herein, each of the above terms (e.g., "alkyl," "aryl" and "heteroaryl") are meant to include both substituted and unsubstituted forms of the indicated radical.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NR(SO$_2$)R', —CN and —NO$_2$ in a number ranging from zero to (2m'+1), where m' is the total number of carbon atoms in such radical. R', R", R'" and R"" are each independently selected from hydrogen, $C_1$-$C_8$ alkyl and heteroalkyl, unsubstituted aryl and heteroaryl, (unsubstituted aryl)-($C_1$-$C_4$)alkyl, and (unsubstituted aryl)oxy-($C_1$-$C_4$)alkyl. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and acyl (e.g., —$C(O)CH_3$, —$C(O)CF_3$, —$C(O)CH_2OCH_3$, and the like).

As used herein, the term "peptide" refers to a compound made up of a single chain of D- or L-amino acids or a mixture of D- and L-amino acids joined by peptide bonds. Generally, peptides are about 2 to about 50 amino acids in length. Preferably, the peptides of the present invention are about 2 to about 25 amino acids in length, more preferably 3 to 20 amino acids in length, and most preferably 3 to 10 amino acids in length.

As used herein, the term "amino acid" refers to naturally occurring, unnatural, and synthetic amino acids, as well as amino acid analogs and amino acid mimetics that function in a manner similar to the naturally occurring amino acids.

As used herein, the terms "naturally-occurring amino acids" refer to those amino acids which are encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof. Stereoisomers of a naturally-occurring α-amino acids include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof.

As used herein, the terms "unnatural amino acids" include, without limitation, amino acid analogs, amino acid mimetics, synthetic amino acids, $N^6$-modified lysines, and N-methyl amino acids in either the L- or D-configuration that function in a manner similar to the naturally-occurring amino acids. Unnatural amino acids are not encoded by the genetic code and can, but do not necessarily have the same basic structure as a naturally occurring amino acid.

As used herein, the terms "amino acid analogs" refer to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

As used herein, the terms "amino acid mimetics" refer to chemical compounds that have a structure that is different from the general chemical structure of an amino acid, but that function in a manner similar to a naturally-occurring amino acid. Suitable amino acid mimetics include, without limitation, β-amino acids and γ-amino acids. In β-amino acids, the amino group is bonded to the β-carbon atom of the carboxyl group such that there are two carbon atoms between the amino and carboxyl groups. In γ-amino acids, the amino group is bonded to the γ-carbon atom of the carboxyl group such that there are three carbon atoms between the amino and carboxyl groups. Suitable R groups for β- or γ-amino acids include, but are not limited to, side-chains present in naturally-occurring amino acids and unnatural amino acids.

As used herein, the terms "$N^6$-modified lysines" refer to unnatural amino acids based on lysine, in which the nitrogen atom of lysine's R-group side chain, $H_2N$—$CH_2$—$CH_2$—$CH_2$—$CH_2$—, is modified with a suitable substituent described above, such as, for example, substituted or unsubstituted alkyl, substituted or unsubstituted heteroalkyl, substituted or unsubstituted haloalkyl, substituted or unsubstituted cycloalkyl, substituted or unsubstituted alkoxy, substituted or unsubstituted aryl, or substituted or unsubstituted heteroaryl. For example, the nitrogen atom of lysine's R-group side chain can be substituted with 3-(pyridin-3-yl)propanoyl or 3-(pyridin-3-yl)prop-2-enoyl.

Amino acids can be characterized by at least one of several properties. For example, amino acids can be positively charged, negatively charged, hydrophilic, or hydrophobic.

As used herein, the terms "positively charged amino acid" refer to those amino acids having a basic or positively charged side chain at pH values below the pKa, and include, but are not limited to, Lys, Arg, His, HoArg, Agp, Agb, Dab, Dap and Orn and stereoisomers thereof. Basic amino acids can generally be referred to by the symbol "$X^+$".

As used herein, the terms "negatively charged amino acid" refer to those amino acids having an acidic or negatively charged side chain at pH values above the pKa, and include, but are not limited to, Asp, Glu, Aad, Bec and stereoisomers thereof. Acidic amino acids can generally be referred to by the symbol "$X^-$". One of skill in the art will appreciate that other basic and acidic amino acids are known in the art.

As used herein, the terms "neutrally charged amino acids" refer to those amino acids having a neutrally charged side chain at pH values equal to the pKa.

As used herein, the terms "hydrophilic amino acid" refer to those amino acids having a polar and uncharged side chain and include, but are not limited to, Asn, Ser, Thr, and Gln.

As used herein, the terms "hydrophobic amino acids" refer to those amino acids having a hydrophobic side chain and include, but are not limited to, Val, Leu, Ile, Met, and Phe. In some embodiments, the hydrophobic amino acid is selected from proline, a proline analog, and a stereoisomer thereof. In some embodiments, the proline analog is hydroxyproline.

As used herein, the terms "D-amino acids" refer to the D stereoisomer of an amino acid. The letters D and L are conventionally used in the art to refer to the stereoisomers of an amino acid. D-amino acids are those amino acids that could be synthesized from the dextrorotary isomer of glyceraldehyde, i.e. D-glyceraldehyde. Similarly, L-amino acids are those amino acids that could be synthesized from the levorotary isomer of glyceraldehyde, i.e. L-glyceraldehyde.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid (i.e., hydrophobic, hydrophilic, positively charged, neutral, negatively charged). The chemically similar amino acid includes, without limitation, a naturally-occurring amino acid such as an L-amino acid, a stereoisomer of a naturally occurring amino acid such as a D-amino acid, and an unnatural amino acid such as an amino acid analog, amino acid mimetic, synthetic amino acid, N-substituted glycine, and N-methyl amino acid. Exemplified hydrophobic amino acids include valine, leucine, isoleucine, methionine, phenylalanine, and tryptophan. Exemplified aromatic amino acids include phenylalanine, tyrosine and tryptophan. Exemplified aliphatic amino acids include serine and threonine. Exemplified basic amino acids include lysine, arginine and histidine. Exemplified amino acids with carboxylate side-chains include aspartate and glutamate. Exemplified amino acids with carboxamide side chains include asparagines and glutamine. Conservative substitution tables providing functionally similar amino acids are well known in the art. Such conservatively modified variants are in addition to and do not exclude polymorphic variants, interspecies homologs, and alleles of the invention.

Conservative substitution tables providing functionally similar amino acids are well known in the art. For example, substitutions may be made wherein an aliphatic amino acid (e.g., G, A, I, L, or V) is substituted with another member of the group. Similarly, an aliphatic polar-uncharged group such as C, S, T, M, N, or Q, may be substituted with another member of the group; and basic residues, e.g., K, R, or H, may be substituted for one another. In some embodiments, an amino acid with an acidic side chain, e.g., E or D, may be substituted with its uncharged counterpart, e.g., Q or N, respectively; or vice versa. Each of the following eight groups contains other exemplary amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

As used herein, the term "linker" refers to a moiety that possesses one or more different reactive functional groups that allows for covalent attachment of moieties such as a peptide to a chelating agent. In some embodiments, the linking moiety possesses two different reactive functional groups, i.e., a heterobifunctional linker. Suitable linkers include, without limitation, those available from Pierce Biotechnology, Inc. (Rockford, IL). In some embodiments, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached.

Linkers useful in the present invention includes those possessing one or more different reactive functional groups that allow for covalent attachment of moieties such as a peptide to a chelating agent. The linking moiety possesses two or more different reactive functional groups. In some cases multivalent linkers can be used. Suitable linkers include, without limitation, those available from Pierce Biotechnology, Inc. (Rockford, IL). In some embodiments, the linker provides a carboxyl group for the attachment of a chelating agent and an amino group for the attachment of a peptide. However, one skilled in the art understands that any reactive functional group can be present on the linker, as long as it is compatible with a functional group on the moiety that is to be covalently attached. As used herein, the term "chelating agent-linker conjugate" refers to a chelating agent covalently attached to a linker. Such chelating agent-linker conjugates can be attached to a peptide via a functional group present on the linker. Some suitable linkers include, but are not limited to, β-alanine, 2,2'-ethylenedioxy bis(ethylamine) monosuccinamide (Ebes) and bis(Ebes)-Lys. Other suitable linkers include those with biotin. Additional linkers can be found in *Bioconjugate Techniques*, Greg T. Hermanson, Academic Press, 2d ed., 2008 (incorporated by reference in its entirety herein).

As used herein, the term "salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic carboxylic acids (acetic acid, propionic acid, glutamic acid, citric acid and the like), organic sulfonic acids (methanesulfonic acid), salts, quaternary ammonium (methyl iodide, ethyl iodide, and the like) salts. It is understood that the pharmaceutically acceptable salts are non-toxic. Additional information on suitable pharmaceutically acceptable salts can be found, for example, in REMINGTON: THE SCIENCE AND PRACTICE OF PHARMACY, $21^{st}$ Ed., Copyright 2006, Lippincott Williams & Wilkins, Philadelphia PA ("Remington"), which is incorporated herein by reference.

Pharmaceutically acceptable salts of the acidic compounds of the present invention include salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts.

As used herein, the term "hydrate" refers to a compound that is complexed to at least one water molecule. The compounds of the present invention can be complexed with from 1 to 10 water molecules.

As used herein, the terms "pharmaceutically acceptable excipient" and "pharmaceutically acceptable carrier" refer to a substance that aids the administration of an active agent to and absorption by a subject. "Pharmaceutically acceptable excipient" refers to an excipient that can be included in the compositions of the invention and that causes no significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors and colors, and the like. One of skill in the art will recognize that other pharmaceutical excipients are useful in the present invention.

As used herein, the term "osteoporosis" refers to a disease of increased bone fragility and/or decrease or reduction in bone density by any defined or undefined cause or condition. "Low bone mass" or "osteopenia" is a condition, not a disease, which may develop into osteoporosis upon continual loss of bone density over time. Low bone mass is characterized by a T-score of −1 to −2.15. Osteoporosis is characterized by a T-score less than −2.15. Among defined causes or conditions to which the methods of the present invention are directed include primary osteoporosis associated with menopause (natural, premature, or surgical), aging, or both, as well as secondary osteoporosis or secondary low bone mass, associated with medical conditions such as Paget's, chronic renal disease, amenorchea from eating disorders, transplantation, hyperthyroidism, parathyroidism, or the use of certain medications, such as various cancer chemotherapies, gonadotropin releasing hormone agonists, medroxy progesterone acetate for birth control, corticosteroids, anticonvulsants, and others.

As used herein, the phrase "Akt signaling" refers to any of a number of biochemical pathways involving the enzymatic activity of serine/threonine-specific protein kinase Akt, also known as protein kinase B or PKB. Akt is itself activated upon phosphorylation by phosphatidylinositol 3-kinase (PI3K) and other kinases. Activated Akt phosphorylates a number of cellular targets resulting in regulation of processes including but not limited to cell viability, angiogenesis, osteogenesis, and cellular metabolism that is associated with cell viability.

As used herein, the term "isomers" refers to compounds with the same chemical formula but which are structurally distinguishable.

As used herein, the term "tautomer" refers to one of two or more structural isomers which exist in equilibrium and which are readily converted from one isomeric form to another.

As used herein, the terms "patient" or "subject" refers to a living organism suffering from or prone to a condition that can be treated by administration of a pharmaceutical composition as provided herein. Non-limiting examples include humans, other mammals and other non-mammalian animals.

As used herein, the term "therapeutically effective amount" refers to an amount of a conjugated functional agent or of a pharmaceutical composition useful for treating or ameliorating an identified disease or condition, or for exhibiting a detectable therapeutic or inhibitory effect. The effect can be detected by any assay method known in the art.

As used herein, the terms "treat", "treating" and "treatment" refers to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the methods of the invention successfully treat a patient's delirium by decreasing the incidence of disturbances in consciousness or cognition.

As used herein, the terms "disorder" or "condition" refer to a state of being or health status of a patient or subject capable of being treated with the peptidomimetic ligand compounds of the present invention.

As used herein, the terms "a," "an," or "a(n)", when used in reference to a group of substituents or "substituent group" herein, mean at least one. For example, where a compound is substituted with "an" alkyl group or aryl group, the compound is optionally substituted with at least one alkyl group and/or at least one aryl group, wherein each alkyl group and/or aryl group is optionally different. In another example, where a compound is substituted with "a" substituent group, the compound is substituted with at least one substituent group, wherein each substituent group is optionally different. Where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, or physiological conditions.

II. PEPTIDOMIMETIC LIGANDS AND PHOSPHONATE DRUG CONJUGATES

In some embodiments, the present invention provides a peptidomimetic ligand compound of Formula I:

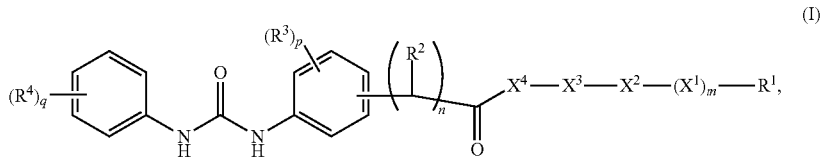

(I)

or a pharmaceutically acceptable salt thereof, wherein $R^1$ is selected from the group consisting of —OH, —NH$_2$, and -L-D. $R^2$ is selected from the group consisting of H, $C_{1-6}$ alkyl, and $C_{3-8}$ cycloalkyl. Each $R^3$ and $R^4$ is independently selected from the group consisting of H, halogen, $C_{1-6}$ alkyl, $C_{1-6}$ alkoxy, and $C_{1-6}$ haloalkyl. $X^1$, $X^2$, and $X^3$ are independently-selected amino acid residues. $X^4$ is selected from the group consisting of an ($N^6$-modified)lysine residue, a citrulline residue, a homocitrulline residue, a leucine residue, an (N-methyl)leucine residue, an isoleucine residue, an (N-methyl)isoleucine residue, and a homophenylalanine residue. L is a linker. D is a phosphonate drug. Subscripts m, n, p, and q are each independently an integer from 0 to 4.

In some embodiments, $R^2$ is selected from H, methyl, ethyl, n-propyl, isopropyl, n-butyl, sec-butyl, isobutyl, tert-butyl, n-pentyl, branched pentyl, n-hexyl, branched hexyl, cyclopropane, cyclobutane, cyclopentane, cyclohexane, cycloheptane, and cyclooctane. In some embodiments, $R^2$ is selected from H, methyl, ethyl, n-propyl, isopropyl, n-butyl, sec-butyl, isobutyl, tert-butyl, n-pentyl, branched pentyl, n-hexyl, and branched hexyl. In some embodiments, $R^2$ is selected from H, methyl, ethyl, n-propyl, and isopropyl. In some embodiments, subscript n is 0, 1, or 2. In some embodiments, subscript n is 1 or 2. In some embodiments, subscript n is 1. In some embodiments, subscript n is 1 or 2 and $R^2$ is selected from H, methyl, ethyl, n-propyl, and isopropyl. In some embodiments, subscript n is 1 or 2 and $R^2$ is selected from H and methyl. In some embodiments, subscript n is 1 and $R^2$ is H.

In some embodiments, each $R^3$ and $R^4$ is independently selected from H, fluoro, chloro, bromo, iodo, methyl, ethyl, n-propyl, isopropyl, n-butyl, sec-butyl, isobutyl, tert-butyl, n-pentyl, branched pentyl, n-hexyl, and branched hexyl. In some embodiments, each $R^3$ and $R^4$ is independently selected from H, fluoro, chloro, bromo, iodo, methyl, ethyl, n-propyl, and isopropyl. In some embodiments, each $R^3$ and $R^4$ is independently selected from H, chloro, bromo, iodo and methyl. In some embodiments, $R^3$ is H and $R^4$ is selected from H, chloro, bromo, and methyl. In some embodiments, $R^3$ is H and $R^4$ is selected from H and methyl. In some embodiments, subscript p is 0 and subscript q is 0, 1, 2, or 3. In some embodiments, subscript p is 0 and subscript q is 1 or 2. In some embodiments, subscript p is 0 and subscript q is 0. In some embodiments, subscript p is 0, subscript q is 1 and $R^4$ is methyl.

In some embodiments, $X^1$, $X^2$, and $X^3$ are independently-selected amino acid residues including, but not limited to, naturally occurring amino acids; D-amino acids; unnatural amino acids which include, without limitation, amino acid analogs, amino acid mimetics, N-substituted glycines, N-methyl amino acids, phenylalanine analogs, and derivatives of lysine (Lys), ornithine (Orn) and α,γ-diaminobutyric acid (Dbu) in either the L- or D-configuration; hydrophilic amino acids; hydrophobic amino acids; positively charged amino acids; and negatively charged amino acids. In some embodiments, subscript m is 0, 1, 2, or 3. In some embodiments, subscript m is 0, 1, or 2. When subscript m is 2, the moiety —$(X^1)_m$— is —$X^{1a}$—$X^{1b}$—, wherein $X^{1a}$ and $X^{1b}$ are also independently-selected amino acid residues as defined for $X^1$, $X^2$, and $X^3$, described above and below.

Naturally-occurring amino acids are those encoded by the genetic code, as well as those amino acids that are later modified, e.g., hydroxyproline, γ-carboxyglutamate and O-phosphoserine. Naturally-occurring α-amino acids include, without limitation, alanine (Ala), cysteine (Cys), aspartic acid (Asp), glutamic acid (Glu), phenylalanine (Phe), glycine (Gly), histidine (His), isoleucine (Ile), arginine (Arg), lysine (Lys), leucine (Leu), methionine (Met), asparagine (Asn), proline (Pro), glutamine (Gln), serine (Ser), threonine (Thr), valine (Val), tryptophan (Trp), tyrosine (Tyr), and combinations thereof.

Stereoisomers of a naturally-occurring α-amino acids include, without limitation, D- and L-amino acids. D-amino acids suitable for use in the present invention include, without limitation, D-alanine (D-Ala), D-cysteine (D-Cys), D-aspartic acid (D-Asp), D-glutamic acid (D-Glu), D-phenylalanine (D-Phe), D-histidine (D-His), D-isoleucine (D-Ile), D-arginine (D-Arg), D-lysine (D-Lys), D-leucine (D-Leu), D-methionine (D-Met), D-asparagine (D-Asn), D-proline (D-Pro), D-glutamine (D-Gln), D-serine (D-Ser), D-threonine (D-Thr), D-valine (D-Val), D-tryptophan (D-Trp), D-tyrosine (D-Tyr), and combinations thereof. In some embodiments, the D-amino acid is selected from a D-α-amino acid, a D-β-amino acid, a D-γ-amino acid, and a combination thereof. In some embodiments, the D-α-amino acid is selected from a stereoisomer of a naturally-occurring α-amino acid, an unnatural D-α-amino acid, and a combination thereof.

Unnatural amino acids include, without limitation, amino acid analogs, amino acid mimetics, N-substituted glycines, N-methyl amino acids, phenylalanine analogs, and derivatives of lysine (Lys), ornithine (Orn) and α,γ-diaminobutyric acid (Dbu) in either the L- or D-configuration that function in a manner similar to the naturally-occurring amino acids. Unnatural amino acids are not encoded by the genetic code, and can, but do not necessarily, have the same basic structure or function as a naturally occurring amino acid.

Unnatural amino acids useful with the present invention include, but are not limited to azetidinecarboxylic acid, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, tertiary-butylglycine, 2,4-diaminoisobutyric acid, desmosine, 2,2'-diaminopimelic acid, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylalanine, N-methylglycine, N-methylisoleucine, N-methylpentylglycine, N-methylvaline, naphthalanine, norvaline, ornithine, pentylglycine, pipecolic acid, thioproline, aminophenylalanine, hydroxytyrosine, and aminotyrosine.

In some other embodiments, the unnatural amino acid is selected from 1-aminocyclopentane-1-carboxylic acid (Acp), 1-aminocyclobutane-1-carboxylic acid (Acb), 1-aminocyclopropane-1-carboxylic acid (Acpc), citrulline (Cit), homocitrulline (HoCit), α-aminohexanedioic acid (Aad), 3-(4-pyridyl)alanine (4-Pal), 3-(3-pyridyl)alanine (3-Pal), propargylglycine (Pra), α-aminoisobutyric acid (Aib), α-aminobutyric acid (Abu), norvaline (Nva), α,β-diaminopropionic acid (Dpr), α,γ-diaminobutyric acid (Dbu), α-tert-butylglycine (Bug), 3,5-dinitrotyrosine Tyr(3,5-di $NO_2$), norleucine (Nle), 3-(2-naphthyl)alanine (Nal-2), 3-(1-naphthyl)alanine (Nal-1), cyclohexylalanine (Cha), di-n-propylglycine (Dpg), cyclopropylalanine (Cpa), homoleucine (Hle), homoserine (HoSer), homoarginine (Har), homocysteine (Hcy), methionine sulfoxide (Met(O)), methionine methylsulfonium (Met (S-Me)), α-cyclohexylglycine (Chg), 3-benzo-thienylalanine (Bta), taurine (Tau), hydroxyproline (Hyp), O-benzyl-hydroxyproline (Hyp(Bzl)), homoproline (HoPro), β-homoproline (βHoPro), thiazolidine-4-carboxylic acid (Thz), nipecotic acid (Nip), isonipecotic acid (IsoNip), 3-carboxymethyl-1-phenyl-1,3,8-triazaspiro[4,5]decan-4-one (Cptd), tetrahydro-isoquinoline-3-carboxylic acid (3-Tic), 5H-thiazolo[3,2-a]pyridine-3-carboxylic acid (Btd), 3-aminobenzoic acid (3-Abz), 3-(2-thienyl)alanine (2-Thi), 3-(3-thienyl)alanine (3-Thi), α-aminooctanedioc acid (Asu), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-$NO_2$)), 1-amino-1-cyclohexane carboxylic acid (Ach), 1-amino-1-(3-piperidinyl)carboxylic acid (3-Apc), 1-amino-1-(4-piperidinyl)carboxylic acid (4-Apc), 2-amino-3-(4-piperidinyl) propionic acid (4-App), 2-aminoindane-2-carboxylic acid (Aic), 2-amino-2-naphthylacetic acid (Ana), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), ornithine (Orn), azetidine-2-carboxylic acid (Aca), α-amino-3-chloro-4,5-dihydro-5-isoazoleacetic acid (Acdi), thiazolidine-2-carboxylic acid (Thz(2-COOH)), allylglycine (Agl), 4-cyano-2-aminobutyric acid (Cab), 2-pyridylalanine (2-Pal), 2-quinoylalanine (2-Qal), cyclobutylalanine (Cba), a phenylalanine analog, a lysine derivative, a ornithine (Orn) derivative, an α,γ-diaminobutyric acid Dbu derivative, stereoisomers thereof, and combinations thereof (see, Liu and Lam, *Anal. Biochem.*, 295: 9-16 (2001)). As such, the unnatural α-amino acids are present either as unnatural L-α-amino acids, unnatural D-α-amino acids, or combinations thereof.

In some embodiments, the unnatural amino acid residue is selected from the following compounds of Table 1:

TABLE 1

Unnatural amino acids useful with the present invention.

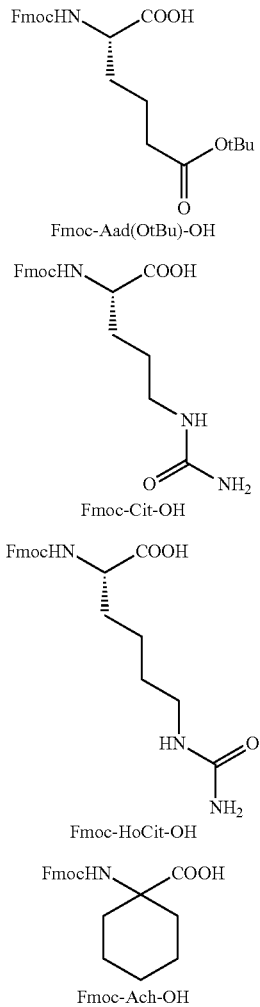

Suitable amino acid analogs include, without limitation, homoserine, norleucine, methionine sulfoxide, methionine methyl sulfonium. Suitable amino acid mimetics include, without limitation, β-amino acids and γ-amino acids. Suitable R groups for β- or γ-amino acids include, but are not limited to, side-chains present in naturally-occurring amino acids and unnatural amino acids.

N-substituted glycines suitable for use in the present invention include, without limitation, N-(2-aminoethyl)glycine, N-β-aminopropyl)glycine, N-(2-methoxyethyl)glycine, N-benzylglycine, (S)—N-(1-phenylethyl)glycine, N-cyclohexylmethylglycine, N-(2-phenylethyl)glycine, N-(3-phenylpropyl)glycine, N-(6-aminogalactosyl)glycine, N-(2-(3'-indolylethyl)glycine, N-(2-(p-methoxyphenylethyl))glycine, N-(2-(p-chlorophenylethyl)glycine, and N-[2-(p-hydroxyphenylethyl)]glycine. N-substituted glycine oligomers, referred to herein as "peptoids," have been shown to be protease resistant (Miller et al., *Drug Dev. Res.*, 35:20-32 (1995)). As such, peptoids containing at least one unnatural α-amino acid, D-amino acid, or a combination thereof are within the scope of the present invention.

Suitable N-methyl amino acids include N-methyl-Ala, N-methyl-Cys, N-methyl-Asp, N-methyl-Glu, N-methyl-Phe, N-methyl-Gly, N-methyl-His, N-methyl-Ile, N-methyl-Arg, N-methyl-Lys, N-methyl-Leu, N-methyl-Met, N-methyl-Asn, N-methyl-Gln, N-methyl-Ser, N-methyl-Thr, N-methyl-Val, N-methyl-Trp, N-methyl-Tyr, N-methyl-Acp, N-methyl-Acb, N-methyl-Acpc, N-methyl-Cit, N-methyl-HoCit, N-methyl-Aad, N-methyl-4-Pal, N-methyl-3-Pal, N-methyl-Pra, N-methyl-Aib, N-methyl-Abu, N-methyl-Nva, N-methyl-Dpr, N-methyl-Dbu, N-methyl-Nle, N-methyl-Nal-2, N-methyl-Nal-1, N-methyl-Cha, N-methyl-Cpa, N-methyl-Hle, N-methyl-HoSer, N-methyl-Har, N-methyl-Hcy, N-methyl-Chg, N-methyl-Bta, N-methyl-2-Thi, N-methyl-3-Thi, N-methyl-Asu, N-methyl-Acdt, N-methyl-Ahch, N-methyl-Akch, N-methyl-Actp, N-methyl-Tyr(3-NO$_2$), N-methyl-Ach, N-methyl-3-Apc, N-methyl-4-Apc, N-methyl-4-App, N-methyl-Tha, N-methyl-Aoa, N-methyl-Aha, N-methyl-Orn, N-methyl-Aca, N-methyl-Agl, N-methyl-Cab, N-methyl-2-Pal, N-methyl-Cba, N-methyl-HoPhe, N-methyl-Phg, N-methyl-Phe(4-NH$_2$), N-methyl-4-Phe(4-Me), N-methyl-Phe(4-F), N-methyl-Phe(4-Cl), N-methyl-Phe(2-Br), N-methyl-Phe(3-Br), N-methyl-Phe(4-Br), N-methyl-Phe(3-CF$_3$), N-methyl-Phe(4-CF$_3$), N-methyl-Phe(4-NO$_2$), N-methyl-Phe(4-CN), N-methyl-Bpa, N-methyl-Phg(4-Cl), N-methyl-Phg(4-Br), N-methyl-Tyr(Me), N-methyl-Lys38, N-methyl-Lys27, N-methyl-Lys73, N-methyl-Lys55, N-methyl-Lys28, N-methyl-Lys72, N-methyl-Lys12, N-methyl-Lys123, N-methyl-Lys63, N-methyl-Lys124, N-methyl-Lys82, N-methyl-Lys31, N-methyl-Lys15, N-methyl-Lys125, N-methyl-Lys43, N-methyl-Lys24, N-methyl-Lys5, N-methyl-Lys4, N-methyl-Lys50, N-methyl-Lys81, N-methyl-Orn38, N-methyl-Orn27, N-methyl-Orn73, N-methyl-Orn55, N-methyl-Orn28, N-methyl-Orn72, N-methyl-Orn12, N-methyl-Orn123, N-methyl-Orn63, N-methyl-Orn124, N-methyl-Orn82, N-methyl-Orn31, N-methyl-Orn15, N-methyl-Orn125, N-methyl-Orn43, N-methyl-Orn24, N-methyl-Orn5, N-methyl-Orn4, N-methyl-Orn50, N-methyl-Orn81, N-methyl-Dbu38, N-methyl-Dbu27, N-methyl-Dbu73, N-methyl-Dbu55, N-methyl-Dbu28, N-methyl-Dbu72, N-methyl-Dbu12, N-methyl-Dbu123, N-methyl-Dbu63, N-methyl-Dbu124, N-methyl-Dbu82, N-methyl-Dbu31, N-methyl-Dbu15, N-methyl-Dbu125, N-methyl-Dbu43, N-methyl-Dbu24, N-methyl-Dbu5, N-methyl-Dbu4, N-methyl-Dbu50, N-methyl-Dbu81, stereoisomers thereof, and combinations thereof.

Suitable phenylalanine analogs useful with the present invention include, without limitation, homophenylalanine (HoPhe), phenylglycine (Phg), 3,3-diphenylalanine (Dpa), 4-aminophenylalanine (Phe(4-NH$_2$)), 2-methylphenylalanine (Phe(2-Me)), 3-methylphenylalanine (Phe(3-Me)), 4-methylphenylalanine (Phe(4-Me)), 4-azidophenylalanine (Phe(4-N$_3$)), 2-fluorophenylalanine (Phe(2-F)), 3-fluorophenylalanine (Phe(3-F)), 4-fluorophenylalanine (Phe(4-F)), 2-chlorophenylalanine (Phe(2-Cl)), 3-chlorophenylalanine (Phe(3-Cl)), 4-chlorophenylalanine (Phe(4-Cl)), 2-bromophenylalanine (Phe(2-Br)), 3-bromophenylalanine (Phe(3-Br)), 4-bromophenylalanine (Phe(4-Br)), 2-iodophenylalanine (Phe(2-I)), 3-iodophenylalanine (Phe(3-I)), 4-iodophenylalanine (Phe(4-I)), 2-trifluoromethylphenylalanine (Phe(2-CF$_3$)), 3-trifluoromethylphenylalanine (Phe(3-CF$_3$)), 4-trifluoromethylphenylalanine (Phe(4-CF$_3$)), 2-methoxyphenylalanine (Phe(2-OMe)), 3-methoxyphenylalanine (Phe(3-OMe)), 2-nitrophenylalanine (Phe(2-NO$_2$)), 3-nitrophenylalanine (Phe(3-NO$_2$)), 4-nitrophenylalanine (Phe(4-NO$_2$)), 2-cyanophenylalanine (Phe(2-CN)), 3-cyanophenylalanine (Phe(3-CN)), 4-cyanophenylalanine (Phe (4-CN)), 3,4-dimethoxyphenylalanine (Phe(3,4-di OMe)), 3,4-difluorophenylalanine (Phe(3,4-di F)), 3,5-difluorophenylalanine (Phe(3,5-di F)), 2,4-dichlorophenylalanine (Phe (2,4-di Cl)), 3,4-dichlorophenylalanine (Phe(3,4-di Cl)), 4-benzoylphenylalanine (Bpa), 4-carboxyphenylalanine (Phe(4-COOH)), 4,4'-biphenylalanine (Bip), 2,3,4,5,6-pentafluorophenylalanine (Phe(F5)), 3,4,5-trifluorophenylalanine (Phe(F3)), 4-chlorophenylglycine (Phg(4-Cl)), 2-chlorophenylglycine (Phg(2-Cl)), 3-chlorophenylglycine (Phg (3-Cl)), 4-bromophenylglycine (Phg(4-Br)), 2-bromophenylglycine (Phg(2-Br)), 3-bromophenylglycine (Phg(3-Br)), 4-ethylphenylalanine (Phe(4-Et)), 4-ethoxyphenylalanine (Phe(4-OEt)), 4-butoxyphenylalanine (Phe(4-OBu)), O-methyltyrosine (Tyr(Me)), O-benzyltyrosine (Tyr (Bzl)), 3,5-dibromotyrosine (Tyr(diBr)), 3,5-diiodotyrosine (Tyr(diI)), homotyrosine (HoTyr), 3-chlorotyrosine (Tyr(3-Cl)), stereoisomers thereof, and combinations thereof.

Suitable derivatives of lysine (Lys), ornithine (Orn) and α,γ-diaminobutyric acid (Dbu) useful with the present invention include, without limitation, Lys38, Lys27, Lys73, Lys55, Lys28, Lys72, Lys12, Lys123, Lys63, Lys124, Lys82, Lys31, Lys15, Lys125, Lys43, Lys24, Lys5, Lys4, Lys50, Lys81, Orn38, Orn27, Orn73, Orn55, Orn28, Orn72, Orn12, Orn123, Orn63, Orn124, Orn82, Orn31, Orn15, Orn125, Orn43, Orn24, Orn5, Orn4, Orn50, Orn81, Dbu38, Dbu27, Dbu73, Dbu55, Dbu28, Dbu72, Dbu12, Dbu123, Dbu63, Dbu124, Dbu82, Dbu31, Dbu15, Dbu125, Dbu43, Dbu24, Dbu5, Dbu4, Dbu50, Dbu81, stereoisomers thereof, and combinations thereof. Derivatives of Orn and Dbu are similar to the lysine derivatives with corresponding carboxylic acid attached to the side chain of Orn and Dbu, respectively. The structures of Lys, Orn, and Dbu derivatives are disclosed in U.S. Pat. No. 7,576,175, which is incorporated herein by reference.

Suitable hydrophobic amino acids useful with the present invention include, without limitation, leucine (Leu), a leucine analog, phenylalanine (Phe), a phenylalanine analog, proline (Pro), a proline analog, valine (Val), isoleucine (Ile), glycine (Gly), alanine (Ala), Met, norvaline (Nva), norleucine (Nle), 1-aminocyclopropane-1-carboxylic acid (Acpc), 1-aminocyclobutane-1-carboxylic acid (Acb), α-cyclohexylglycine (Chg), cyclohexylalanine (Cha), propargylglycine (Pra), cyclopropylalanine (Cpa), homoleucine (Hle), α-aminoisobutyric acid (Aib), α-aminobutyric acid (Abu), 3-(2-thienyl)alanine (2-Thi), 3-(3-thienyl)alanine (3-Thi), 3-(3-pyridyl)alanine (3-Pal), 3-(2-naphthyl)alanine (Nal-2), 2-amino-2-naphthylacetic acid (Ana), tyrosine (Tyr), 3,5-dinitrotyrosine (Tyr(3,5-di NO$_2$)), diethylglycine (Deg), 4-amino-4-carboxy-1,1-dioxo-tetrahydrothiopyran (Acdt), 1-amino-1-(4-hydroxycyclohexyl) carboxylic acid (Ahch), 1-amino-1-(4-ketocyclohexyl)carboxylic acid (Akch), 4-amino-4-carboxytetrahydropyran (Actp), 3-nitrotyrosine (Tyr(3-NO$_2$)), 1-amino-1-cyclohexane carboxylic acid (Ach), 2-aminoindane-2-carboxylic acid (Aic), (2S, 5R)-5-phenylpyrrolidine-2-carboxylic acid (Ppca), 4-thiazoylalanine (Tha), 2-aminooctanoic acid (Aoa), 2-aminoheptanoic acid (Aha), and a stereoisomer thereof. In some embodiments, the proline analog is hydroxyproline.

In some embodiments, the hydrophobic amino acid is selected from the compounds of Table 2:

TABLE 2

Hydrophobic amino acids useful in the present invention.

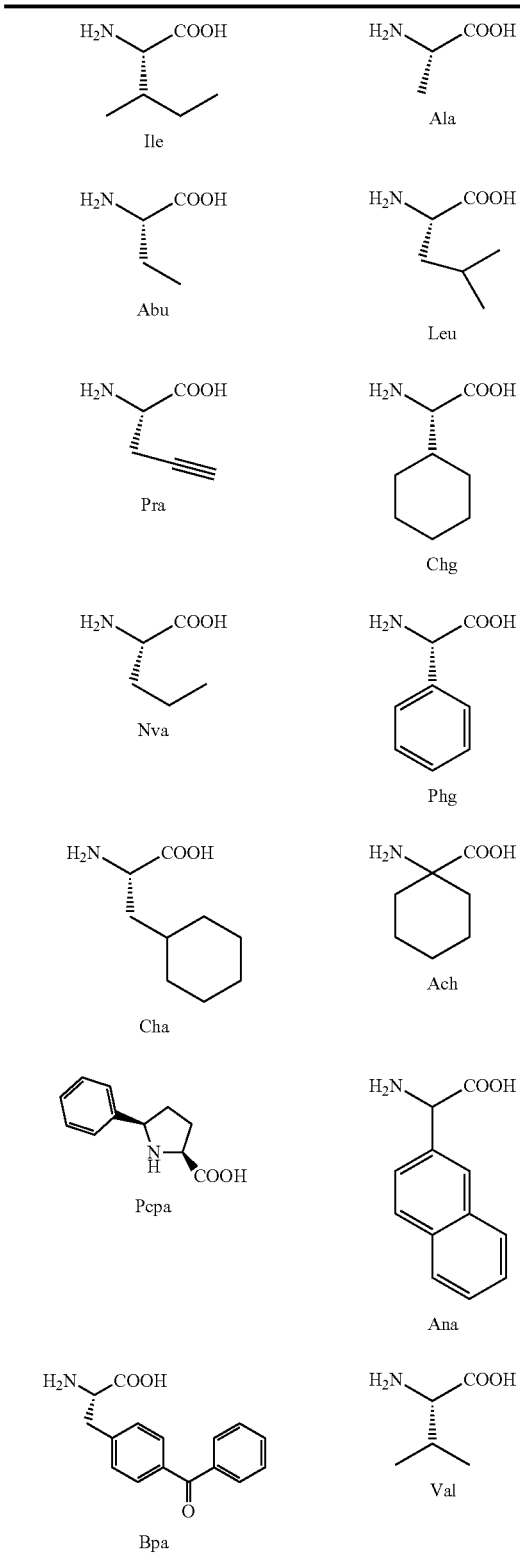

TABLE 2-continued

Hydrophobic amino acids useful in the present invention.

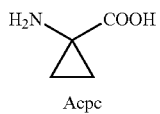
Acpc

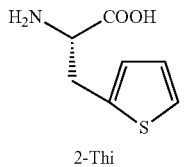
2-Thi

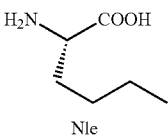
Nle

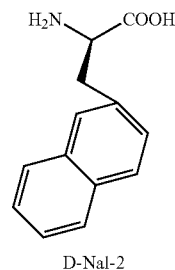 [SMILES: N[C@H](Cc1ccc2ccccc2c1)C(=O)O]
D-Nal-2

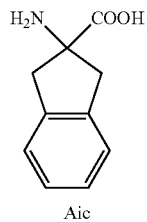
Aic

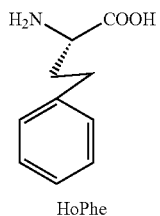 [SMILES: N[C@@H](CCc1ccccc1)C(=O)O]
HoPhe

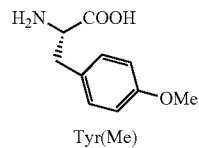 [SMILES: COc1ccc(C[C@H](N)C(=O)O)cc1]
Tyr(Me)

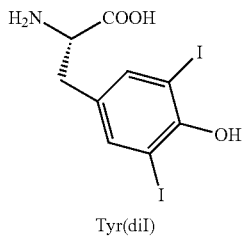 [SMILES: N[C@@H](Cc1cc(I)c(O)c(I)c1)C(=O)O]
Tyr(diI)

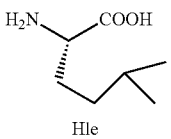
Hle

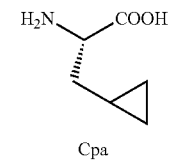
Cpa

TABLE 2-continued

Hydrophobic amino acids useful in the present invention.

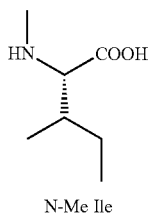
N-Me Ile

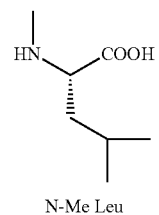
N-Me Leu

In some embodiments, the hydrophobic amino acid is selected from the compounds of Table 3:

TABLE 3

Hydrophobic amino acids useful in the present invention.

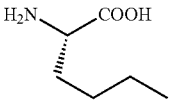
Nle

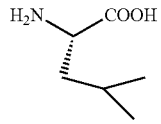
Leu

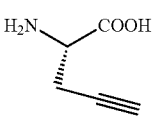
Pra

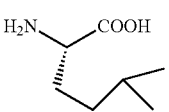
Hle

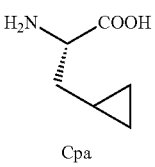
Cpa

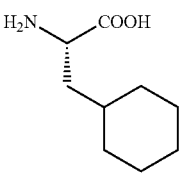
Cha

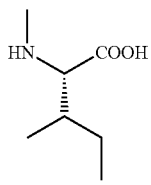
N-Me Ile

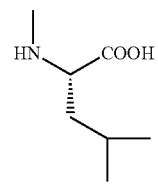
N-Me Leu

Suitable hydrophilic amino acids useful with the present invention include, without limitation, Asn, Ser, Thr, Gln, and stereoisomers thereof. Suitable positively charged amino acids useful with the present invention include, but are not limited to, Lys, Arg, His, HoArg, Agp, Agb, Dab, Dap, Orn, and stereoisomers thereof. Suitable negatively charged amino acids useful with the present invention include, without limitation, aspartic acid, glutamic acid, α-aminohexanedioic acid, α-aminooctanedioc acid, homoaspartic acid, γ-carboxy-glutamic acid, 4-carboxyphenylalanine, and a stereoisomer thereof. In other embodiments, the negatively charged amino acid is selected from Aad, Bec and Bmc.

In some embodiments, $X^1$ can be an unnatural amino acid, a hydrophobic amino acid, a positively charged amino acid, or a negatively charged amino acid. In some embodiments, $X^2$ can be a hydrophilic amino acid, hydrophobic amino acid, or a negatively charged amino acid. In some embodiments, $X^2$ can be a negatively charged amino acid residue, a hydrophilic amino acid residue, a hydroxyproline (Hyp) residue, or a 1-amino-1-cyclohexane carboxylic acid (Ach) residue. In some embodiments, $X^3$ can be a hydrophilic amino acid, hydrophobic amino acid, or a negatively charged amino acid. In some embodiments, when subscript m is 2, and the moiety —$(X^1)_m$— is —$X^{1a}$—$X^{1b}$—, $X^{1a}$ can be an unnatural amino acid, a hydrophobic amino acid, or a negatively charged amino acid; and $X^{1b}$ can be a hydrophilic amino acid, a hydrophobic amino acid, or a negatively charged amino acid.

In some embodiments, $X^4$ is selected from $N^6$-(3-(pyridin-3-yl)propanoyl)-lysine (Lys12), (E)-$N^6$-(3-(pyridin-3-yl)acryloyl)-lysine (Lys38), citrulline (Cit), homocitrulline (HoCit), leucine (Leu), N-methyl-leucine (N-MeLeu), isoleucine (Ile), N-methyl-isoleucine (N-MeIle), and homophenylalanine (HoPhe). In some embodiments, $X^4$ is citrulline (Cit) or $N^6$-(3-(pyridin-3-yl)propanoyl)-lysine (Lys12).

In some embodiments, the compound has a structure according to Formula Ia:

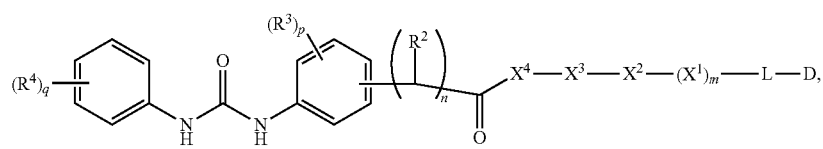

(Ia)

or a pharmaceutically acceptable salt thereof.

In some embodiments, the compound has a structure according to Formula Ib:

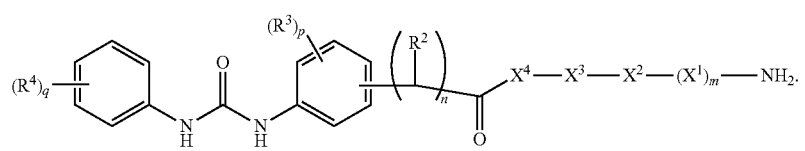

(Ib)

In some embodiments, the compound has a structure according to Formula Ic:

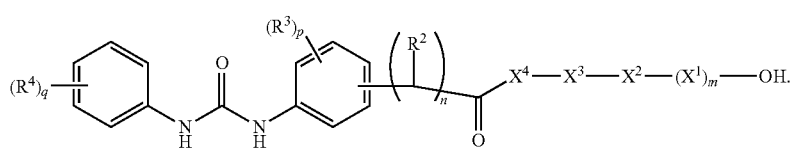

(Ic)

In some embodiments, the compound has a structure according to Formula II:

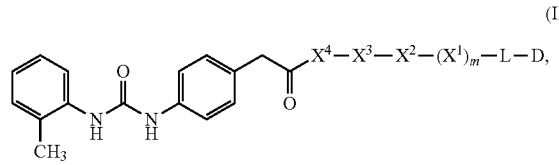

(II)

or a pharmaceutically acceptable salt thereof.

In some embodiments, the invention provides compounds of Formula I, Ia, Ib, Ic, or II wherein $X^1$ can be an unnatural amino acid, a hydrophobic amino acid, a positively charged amino acid, or a negatively charged amino acid; $X^2$ can be a hydrophilic amino acid, hydrophobic amino acid, or a negatively charged amino acid; $X^3$ can be a hydrophilic amino acid, hydrophobic amino acid, or a negatively charged amino acid; and $X^4$ can be $N^6$-(3-(pyridin-3-yl)propanoyl)-lysine (Lys12), (E)-$N^6$-(3-(pyridin-3-yl)acryloyl)-lysine (Lys38), citrulline (Cit), homocitrulline (HoCit), leucine (Leu), N-methyl-leucine (N-MeLeu), isoleucine (Ile), N-methyl-isoleucine (N-MeIle), and homophenylalanine (HoPhe). In some embodiments, when subscript m is 2, and the moiety —$(X^1)_m$— is —$X^{1a}$—$X^{1b}$—, $X^{1a}$ can be an unnatural amino acid, a hydrophobic amino acid, or a negatively charged amino acid; and $X^{1b}$ can be a hydrophilic amino acid, a hydrophobic amino acid, or a negatively charged amino acid.

In some embodiments, the invention provides compounds of Formula I, Ia, Ib, Ic, or II wherein $X^1$ can be proline (Pro), α-aminohexanedioic acid (Aad), valine (Val), arginine (Arg), 1-amino-1-(4-piperidinyl)carboxylic acid (4-Apc), D-histidine (D-His), D-O-methyltyrosine (D-Tyr(Me)), ornithine (Orn), α-aminoisobutyric acid (Aib), tyrosine (Tyr), homocitrulline (HoCit), norleucine (Nle), aspartic acid (Asp), isoleucine (Ile), or D-leucine (D-Leu); $X^2$ can be aspartic acid (Asp), isoleucine (Ile), serine (Ser), glutamic acid (Glu), D-glutamic acid (D-Glu), D-propargylglycine (D-Pra), 1-amino-1-cyclohexane carboxylic acid (Ach), 1-aminocyclopropane-1-carboxylic acid (Acpc), 4-methylphenylalanine (Phe(4-Me)), cyclohexylalanine (Cha), α-aminohexanedioic acid (Aad), hydroxyproline (Hyp), 2-aminoindane-2-carboxylic acid (Aic), glutamine (Gln), or D-α-cyclohexylglycine (D-Chg); $X^3$ can be glutamic acid (Glu), aspartic acid (Asp), α-aminohexanedioic acid (Aad), isoleucine (Ile), serine (Ser), or norleucine (Nle); and $X^4$ can be $N^6$-(3-(pyridin-3-yl)propanoyl)-lysine (Lys12), (E)-$N^6$-

(3-(pyridin-3-yl)acryloyl)-lysine (Lys38), citrulline (Cit), homocitrulline (HoCit), leucine (Leu), N-methyl-leucine (N-MeLeu), isoleucine (Ile), N-methyl-isoleucine (N-MeIle), and homophenylalanine (HoPhe). In some embodiments, when subscript m is 2, and the moiety —(X$^1$)$_m$— is —X$^{1a}$—X$^{1b}$—, X$^{1a}$ can be homocitrulline (HoCit), isoleucine (Ile), D-leucine (D-Leu), or aspartic acid (Asp); and X$^{1b}$ can be aspartic acid (Asp), threonine (Thr), or D-O-methyltyrosine (D-Tyr(Me)).

In some embodiments, the invention provides compounds of Formula I, Ia, Ib, Ic, or II, wherein subscript m is 0, and the moiety —X$^4$—X$^3$—X$^2$— is -Lys12-Aad-Ach-, -Ile-Glu-Acpc-, or -HoPhe-Nle-Glu-. In some embodiments, the invention provides compounds of Formula I, Ia, Ib, or II, wherein subscript m is 1, and the moiety —X$^4$—X$^3$—X$^2$—X$^1$— is —N-MeIle-Glu-Asp-Pro-, -Lys12-Glu-Ile-Aad-, -Cit-Glu-Ser-Val-, -Lys12-Glu-Glu-Arg-, —N-MeLeu-Asp-D-Pra-4-Apc-, -Lys38-Glu-Ile-Aad-, -Lys38-Glu-Glu-Arg-, -HoCit-Ile-Phe(4-Me)-D-His-, -Leu-Ser-Cha-D-Tyr(Me)-, -HoCit-Glu-Glu-Orn-, -Ile-Glu-Aad-Aib-, -Lys38-Aad-Phe(4-Me)-Tyr-, -Lys38-Aad-Aic-Nle-, -Ile-Aad-Ser-Asp-, or -Ile-Aad-Ser-Tyr-. In some embodiments, the invention provides compounds of Formula I, Ia, Ib, Ic, or II, wherein subscript m is 2, and the moiety —X$^4$—X$^3$—X$^2$—X$^{1a}$—X$^{1b}$— is -Lys12-Aad-Hyp-HoCit-Asp-, -HoCit-Aad-Gln-Ile-Asp-, -HoCit-Aad-D-Glu-D-Leu-Thr-, or -HoCit-Aad-D-Chg-Asp-D-Tyr(Me)-. In some embodiments, the invention provides compounds of Formula I, Formula Ia, Formula II, or pharmaceutically acceptable salts thereof, wherein subscript m is 0, and the moiety —X$^4$—X$^3$—X$^2$— is -Lys12-Aad-Ach-. In some embodiments, the invention provides compounds of Formula I, Formula Ia, Formula II, or pharmaceutically acceptable salts thereof, wherein subscript m is 1, and the moiety —X$^4$—X$^3$—X$^2$—X$^1$— is -Cit-Glu-Ser-Val-.

In some embodiments, the compounds of Formula Ib are selected from:

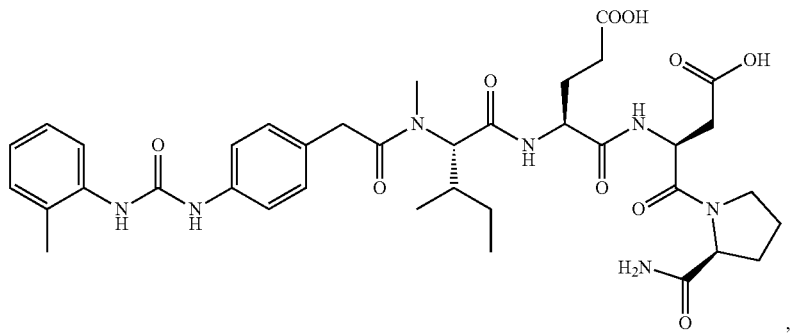

,

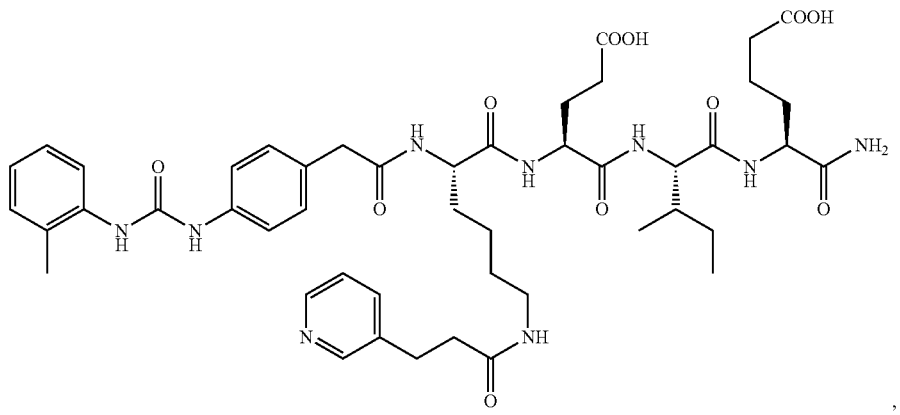

,

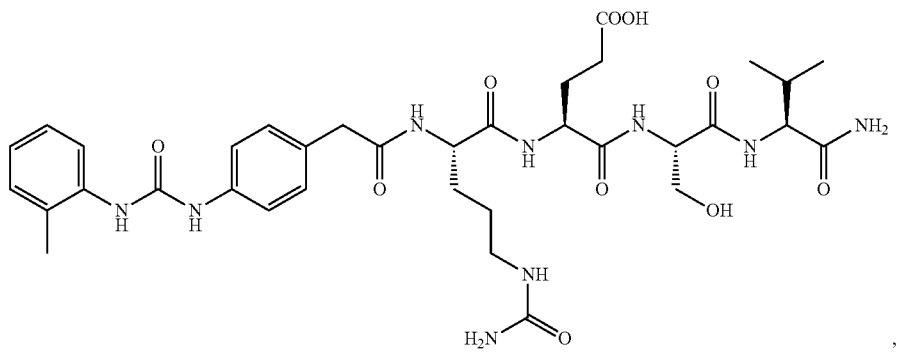

,

-continued
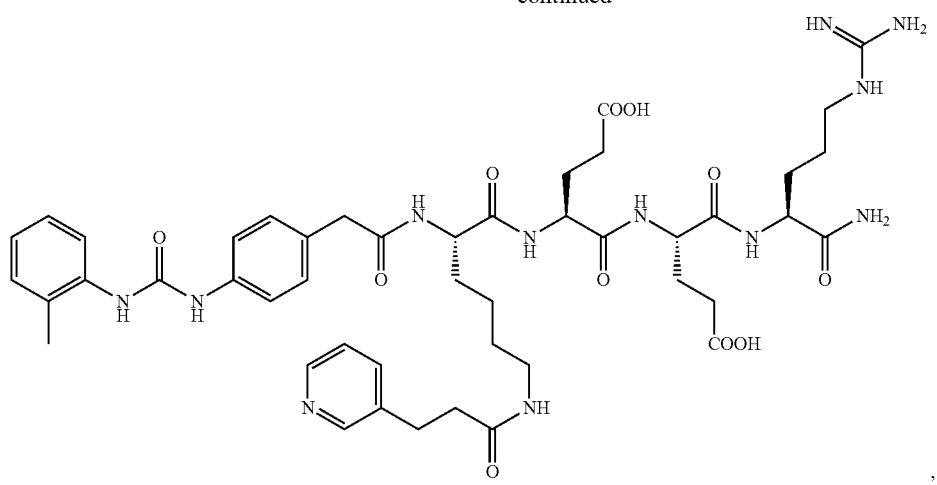
,
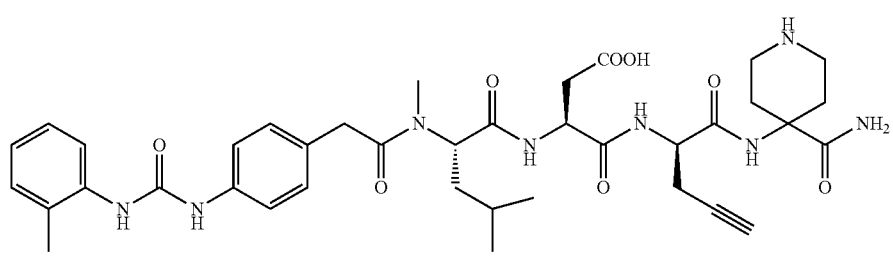
,
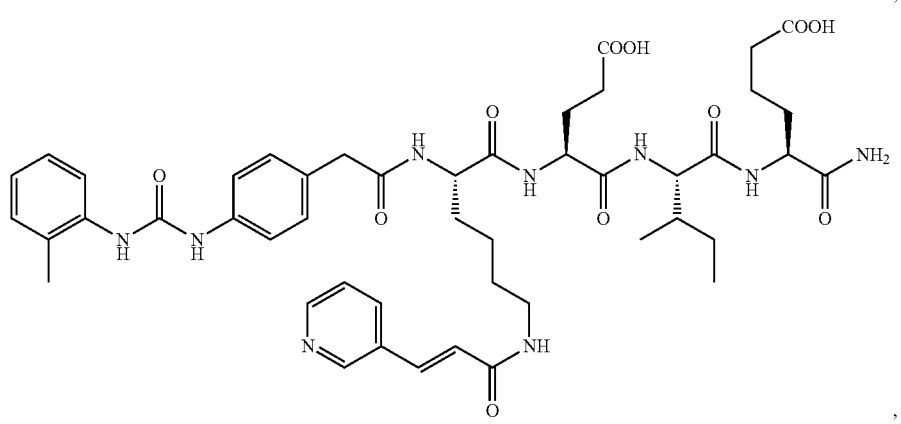
,
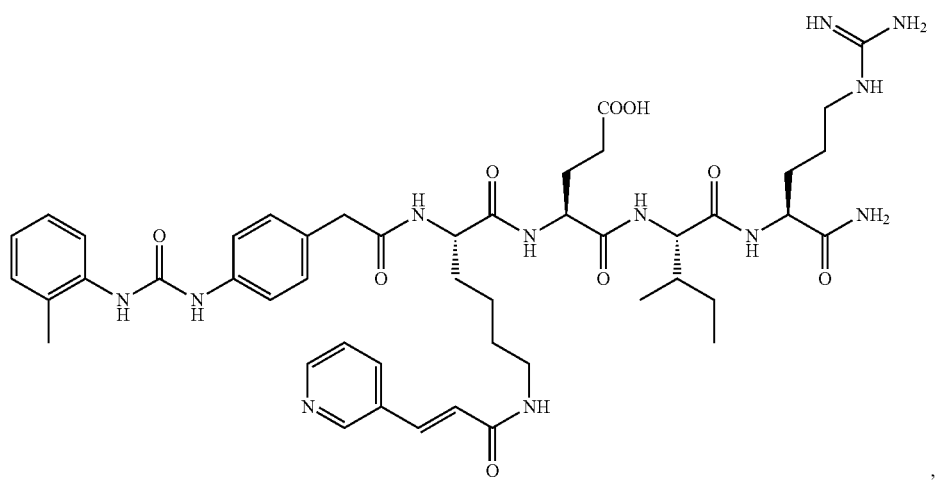
,

-continued
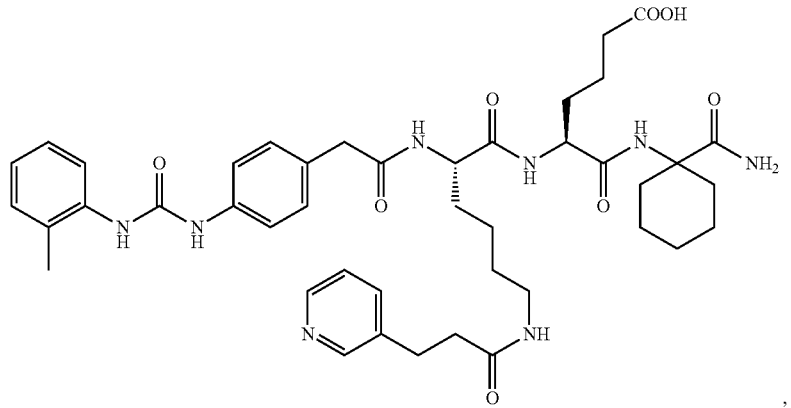
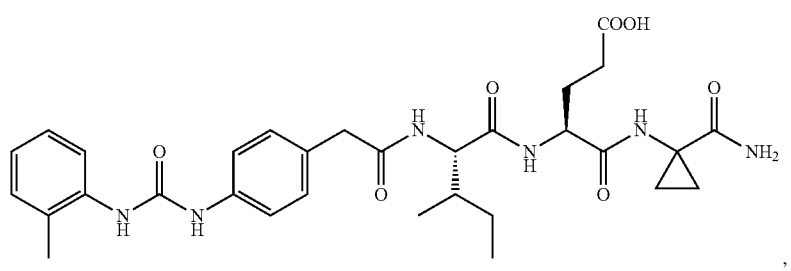
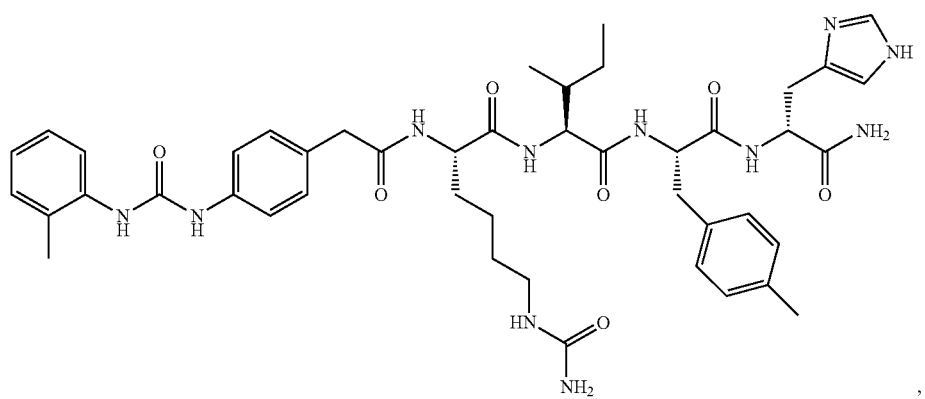
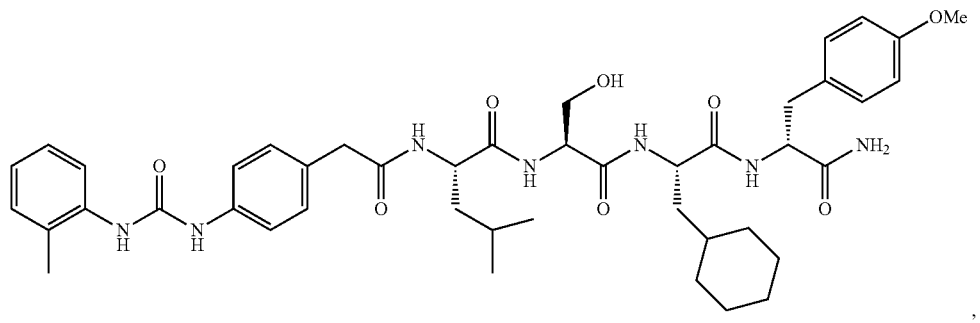

-continued
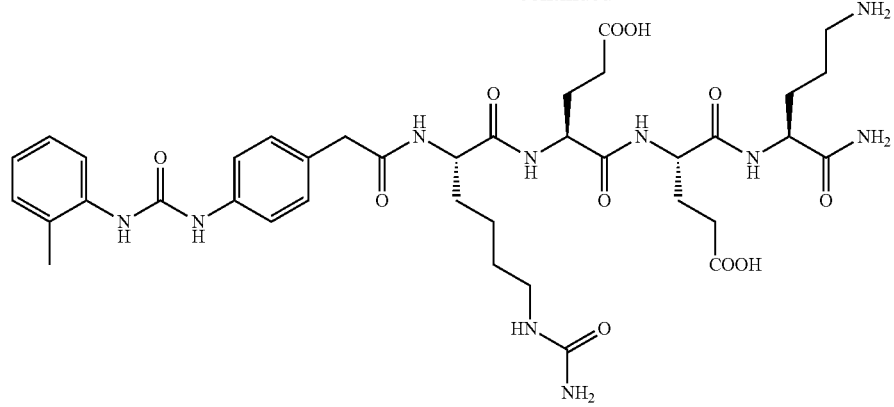
,
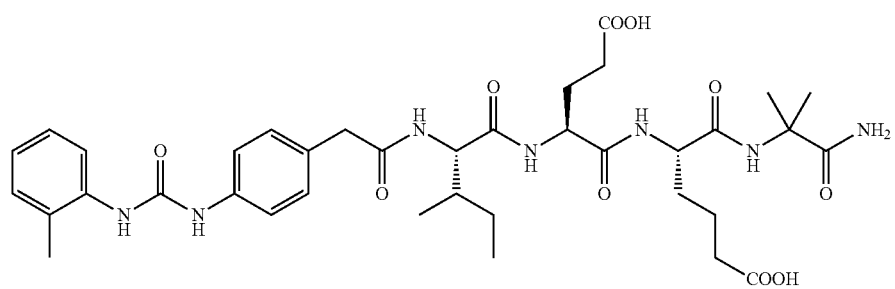
,
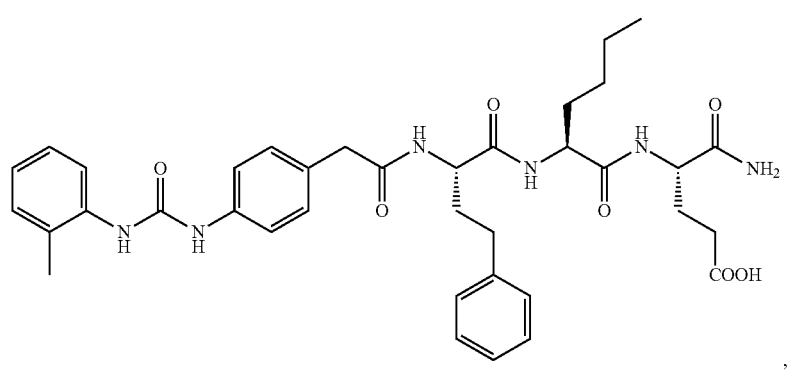
,
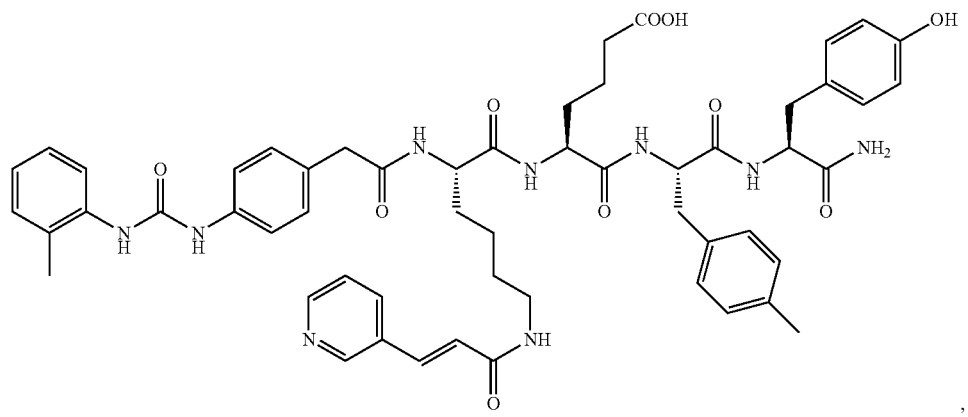
,

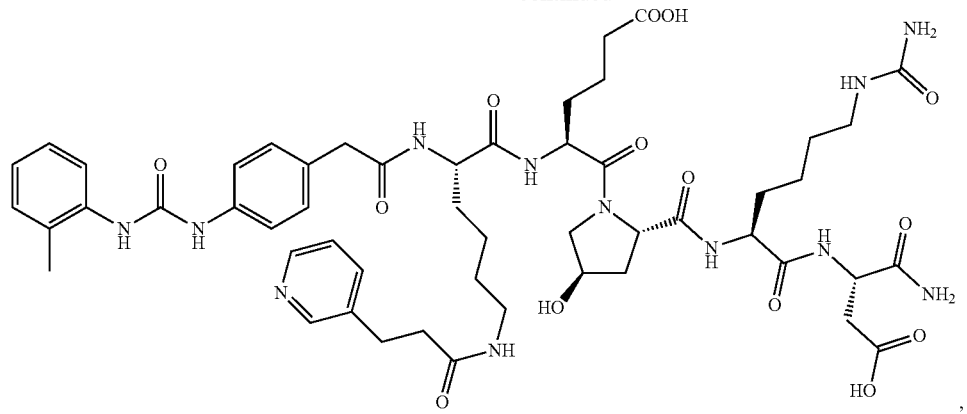
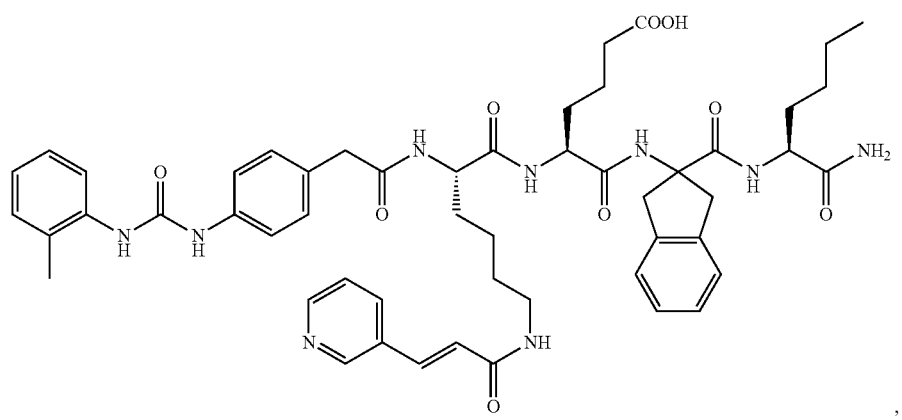
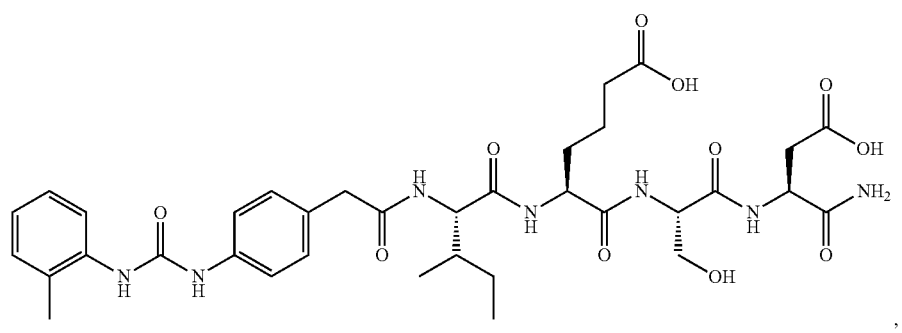
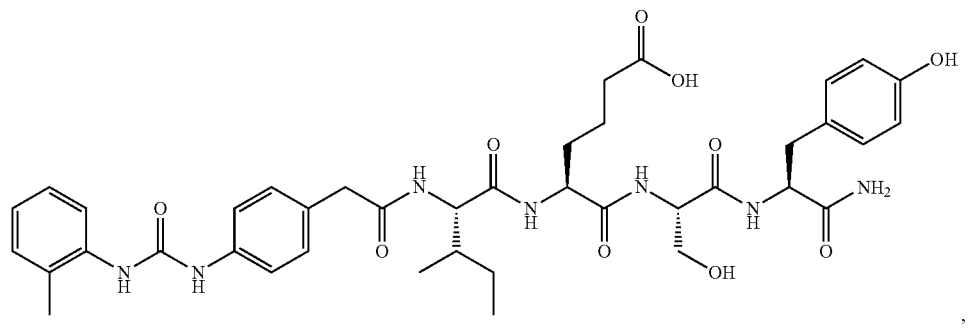

-continued
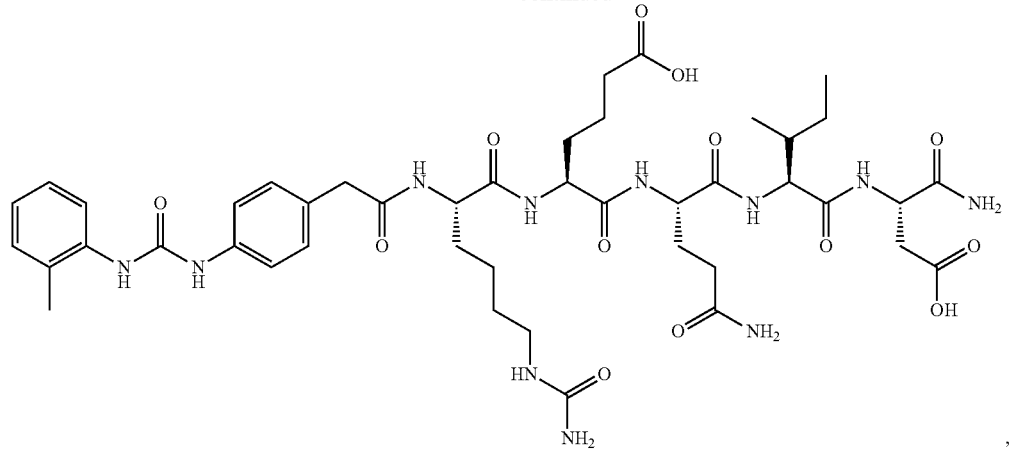
,
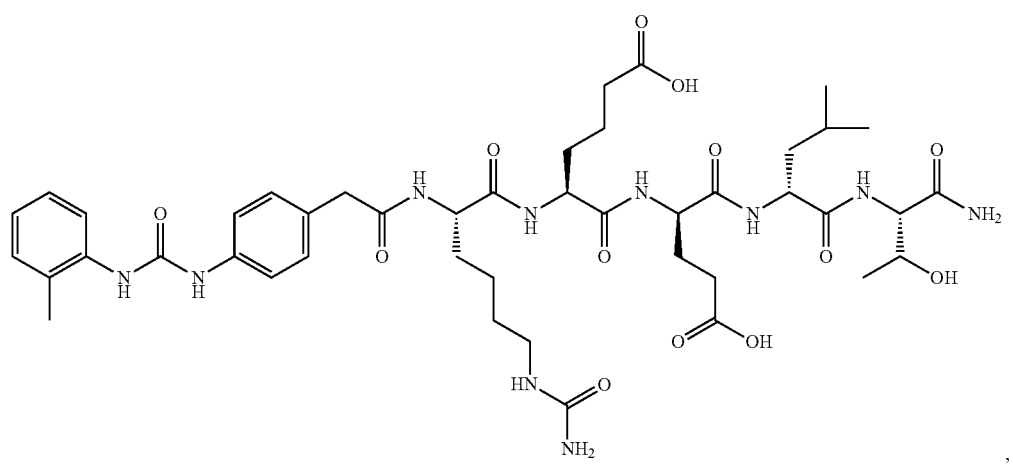
, and
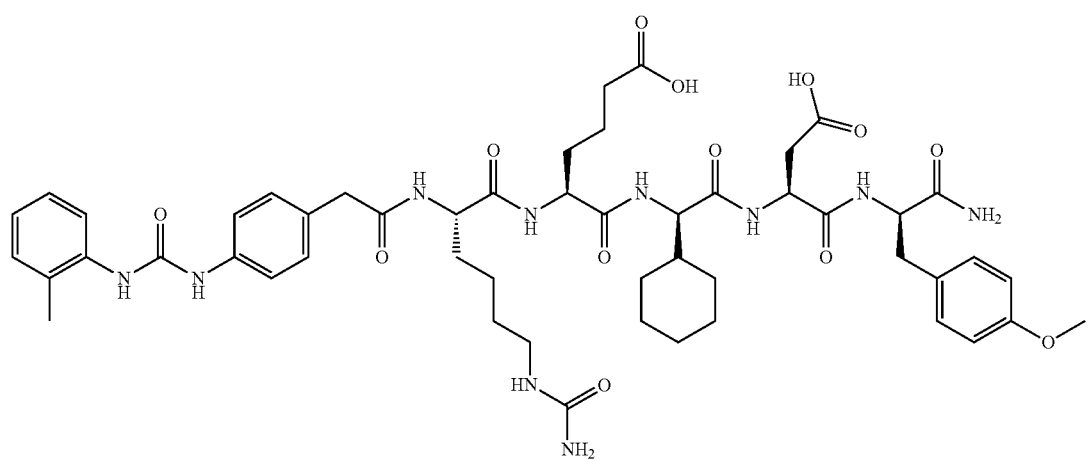 [SMILES: COc1ccc(C[C@@H](NC(=O)[C@H](CC(=O)O)NC(=O)[C@H](NC(=O)[C@H](CCCC(=O)O)NC(=O)[C@H](CCCCNC(N)=O)NC(=O)Cc2ccc(NC(=O)Nc3ccccc3C)cc2)C2CCCCC2)C(N)=O)cc1 ; "."]
.

In some embodiments, the compounds of Formula Ic are selected from:
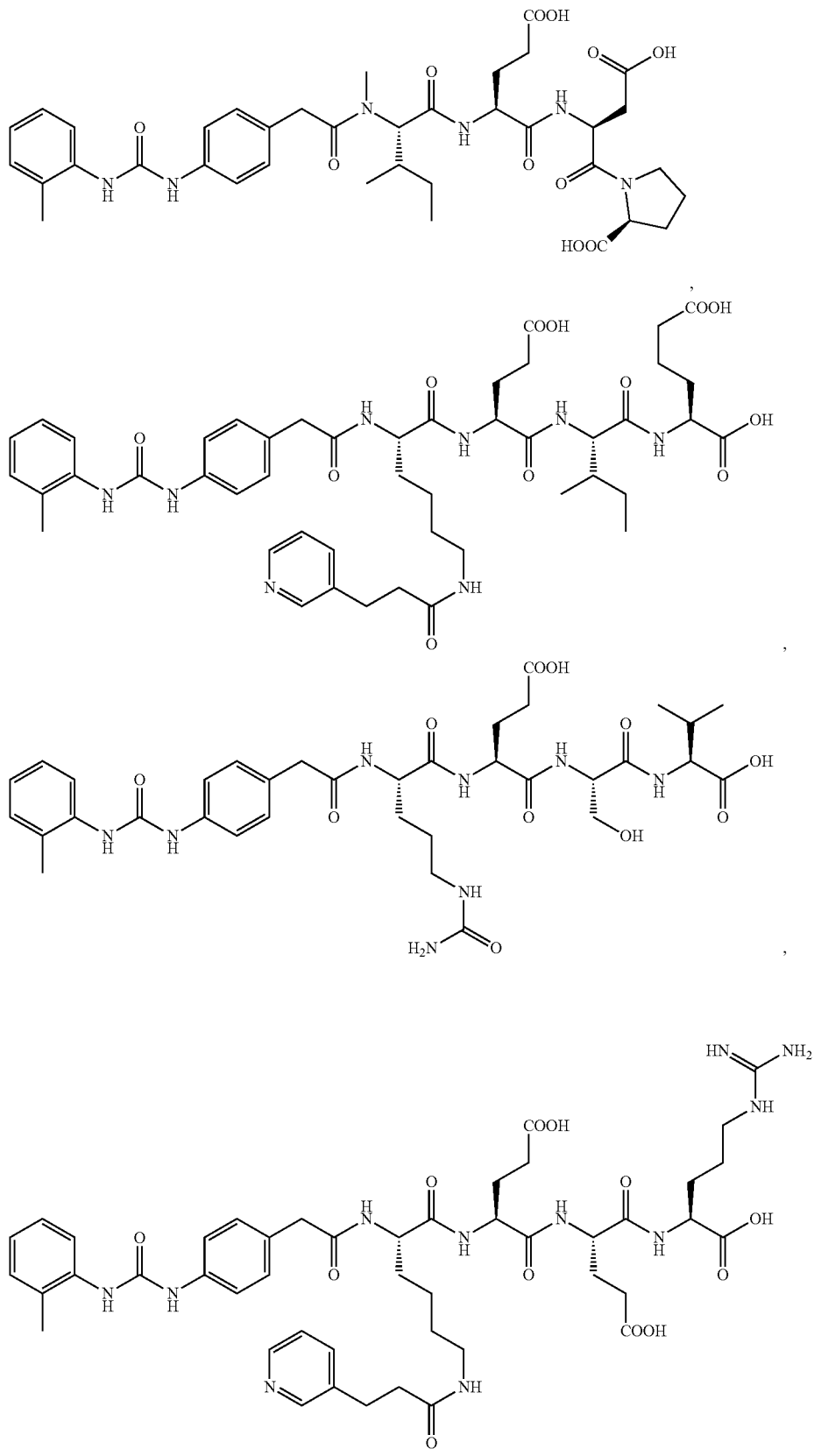

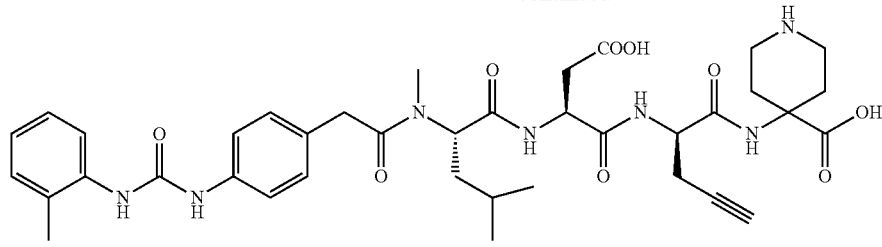
,
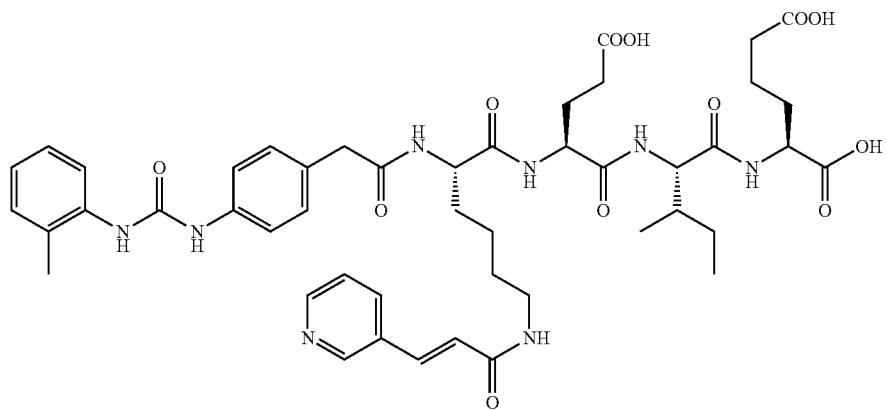
,
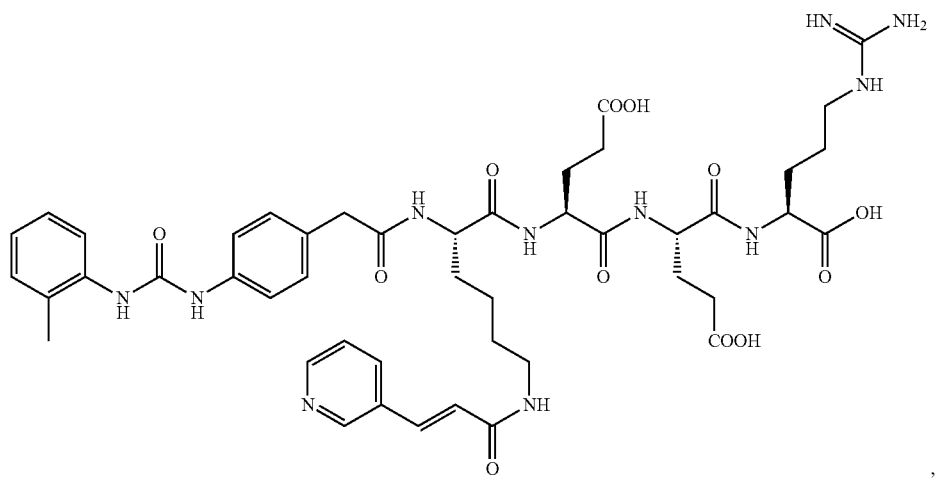
,
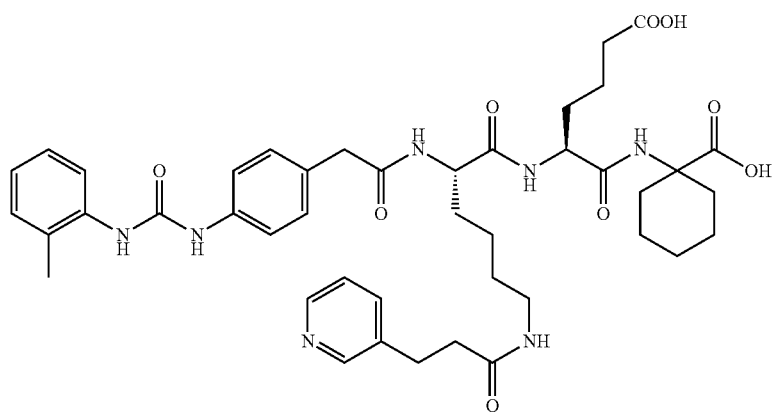
,

-continued
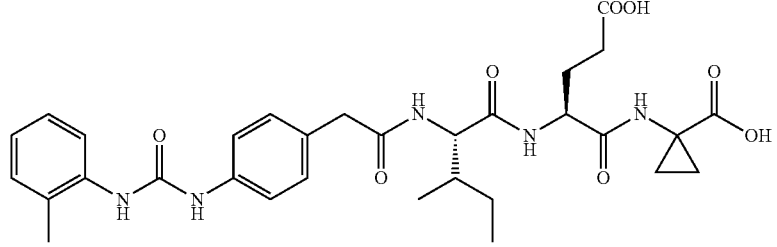
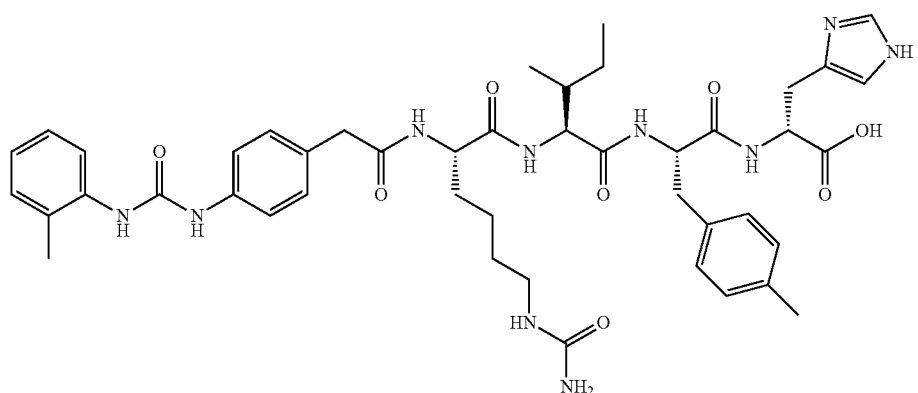
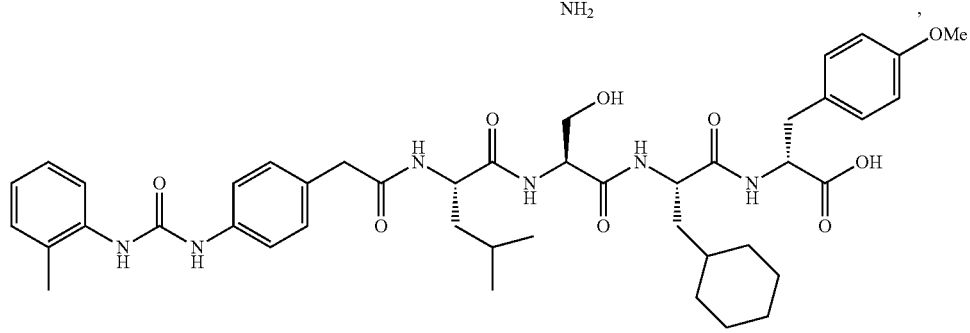
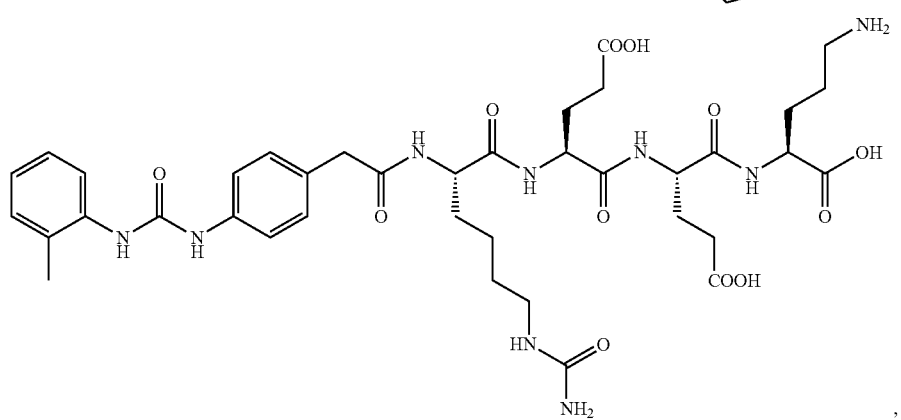
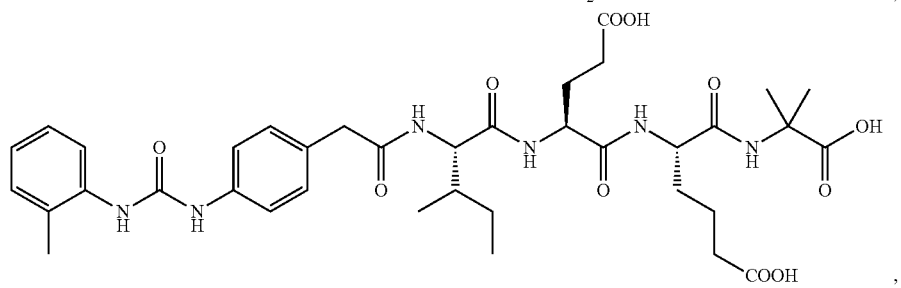

-continued
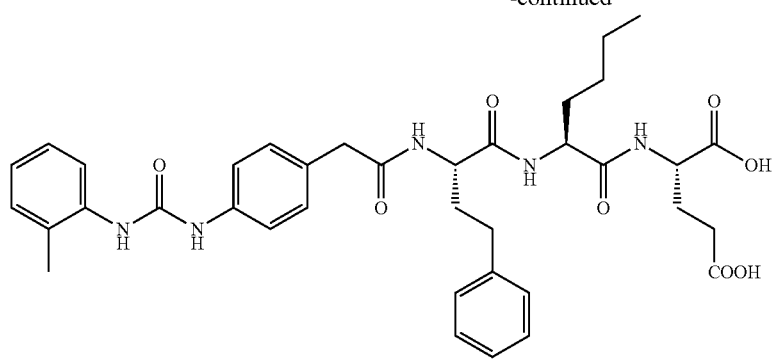
,
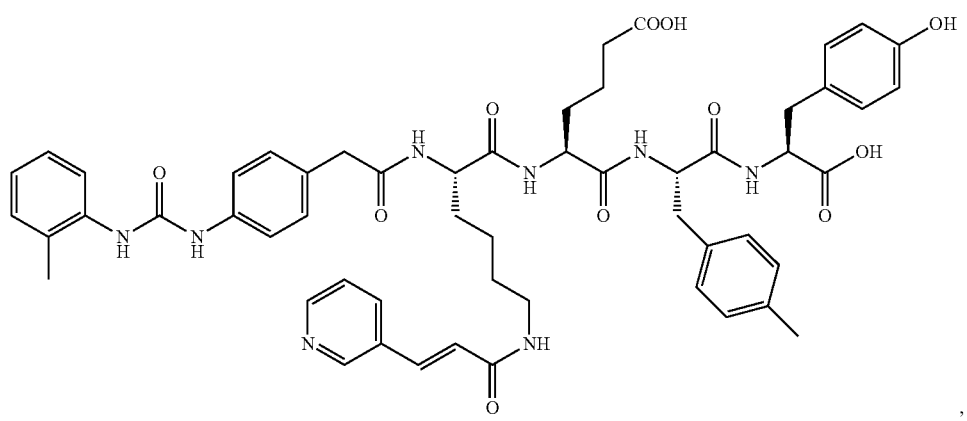
,
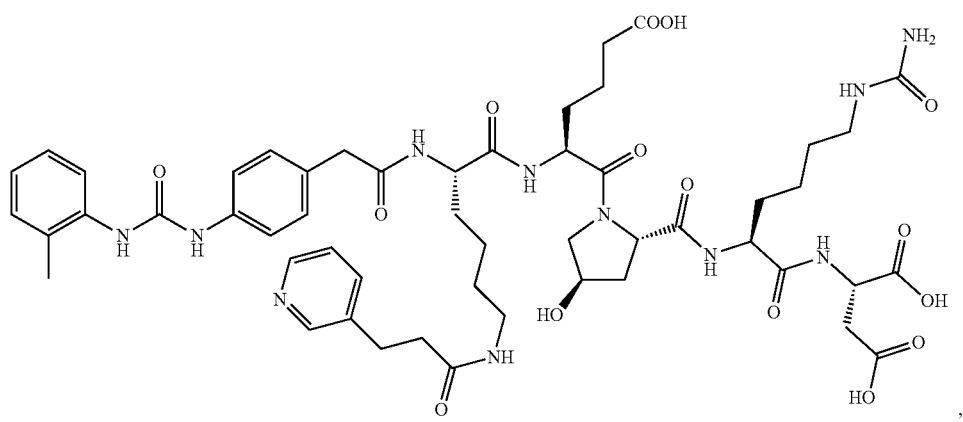
,
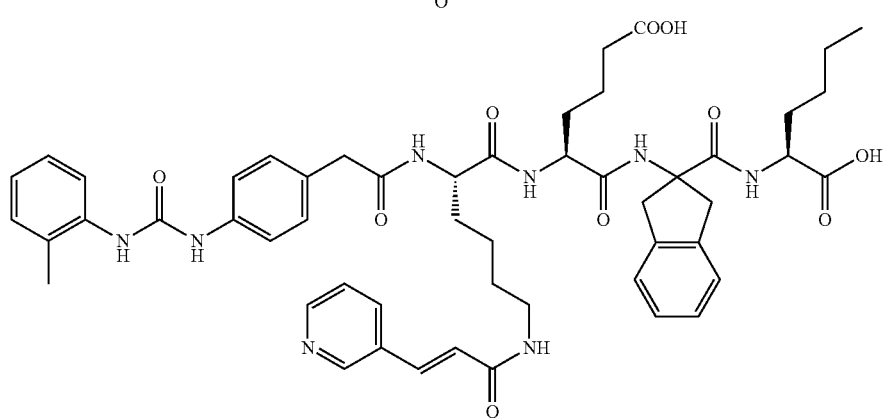
,

-continued
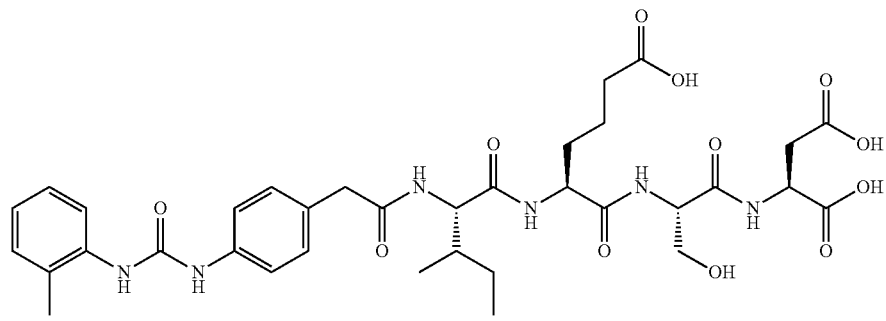
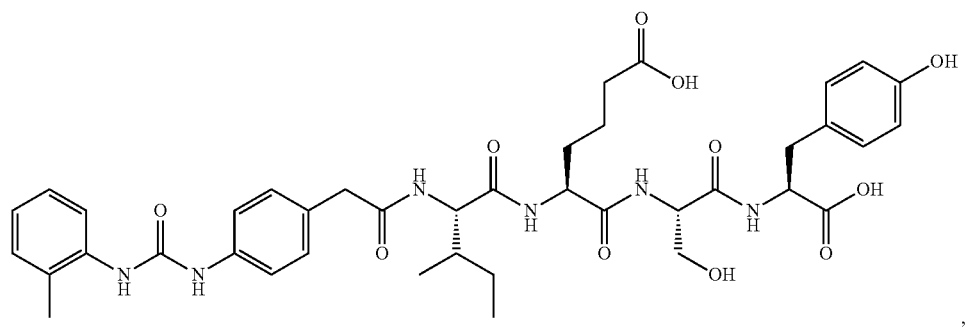
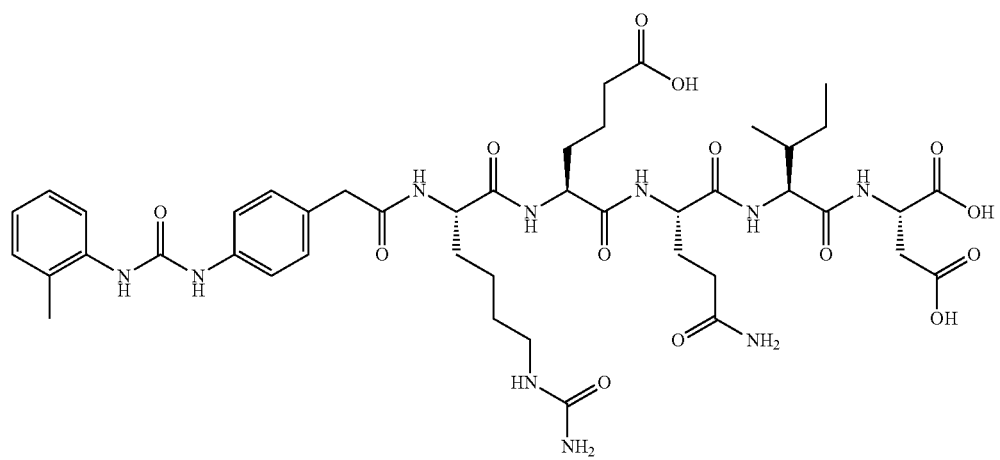

-continued

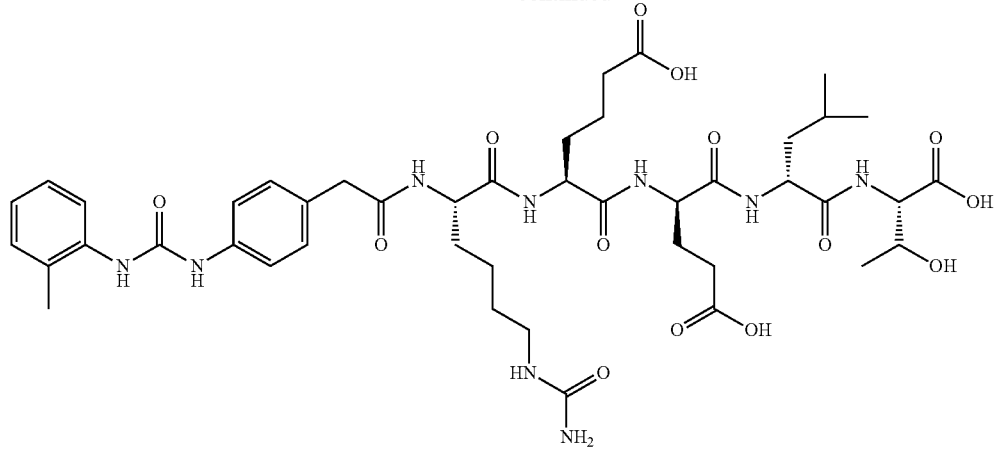

, and

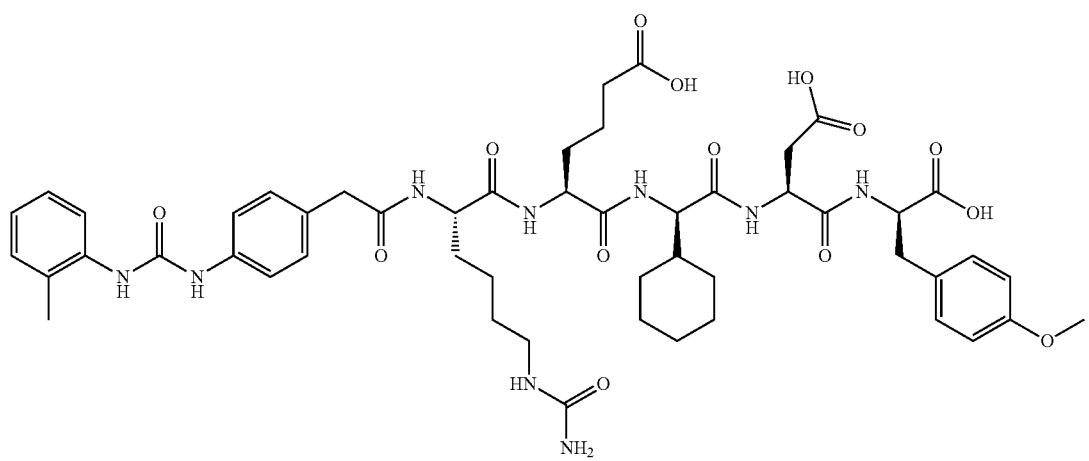

The L moiety of Formula I, Formula Ia, and Formula II can be any suitable linker including, but not limited to, linkers possessing one or more different reactive functional groups that allow for covalent attachment of moieties such as a peptides, monomers, and polymers. The linking moiety can possess two or more different reactive functional groups. In some cases multivalent linkers can be used and multiple peptides of the present invention and/or multiple active agents can be linked via the linker. Suitable linkers include, without limitation, those available from Pierce Biotechnology, Inc. (Rockford, IL). One skilled in the art understands that any reactive functional group can be present on the linker, as long as it is compatible with a functional group on the moiety that is to be covalently attached. Some suitable linkers include, but are not limited to, β-alanine, 2,2'-ethylenedioxy bis(ethylamine) monosuccinamide (Ebes), bis(Ebes)-Lys, and polyethylene glycol. Other suitable linkers include affinity-based linkers that bind moieties via non-covalent interactions (e.g., biotin-containing linkers). Other suitable linkers include cleavable linkers such as disulfide linkers, such as, for example, 4-((2-((2-aminoethyl)disulfanyl)ethyl)amino)-4-oxobutanoic acid, which can be cleaved under reducing conditions, or peptide linkers, which can be cleaved by the action of proteases.

A person of ordinary skill in the art will recognize that other linkers are possible with the compounds of the present invention. Many such linkers can be found in, or prepared by the techniques recited in, "Bioconjugate Techniques" by Greg T Hermanson, Academic Press, San Diego, 1996, which is hereby incorporated by reference. Furthermore, a person of ordinary skill in the art will recognize that other linkers can be prepared based on Click Chemistry synthetic techniques as described in Kolb, H. C., Finn, M. G., Sharpless, K. B., Angew. Chem. Int'l. Ed. 40 (11): 2004-2021 (2001), which is hereby incorporated by reference. Linkers useful with the present invention include those based on the Ebes and PEG moiety. The linker can include either 0 to 6 Ebes or PEG groups. Ebes and PEG groups can be conjugated by the techniques referenced above. In some embodiments, the linker L of Formula I, Formula Ia, and Formula II includes at least one of N-(8-amino-3,6-dioxa-octyl)succinamic acid (Ebes) and polyethylene glycol (PEG).

In some other embodiments, the linker L of Formula I, Formula Ia, and Formula II is selected from:
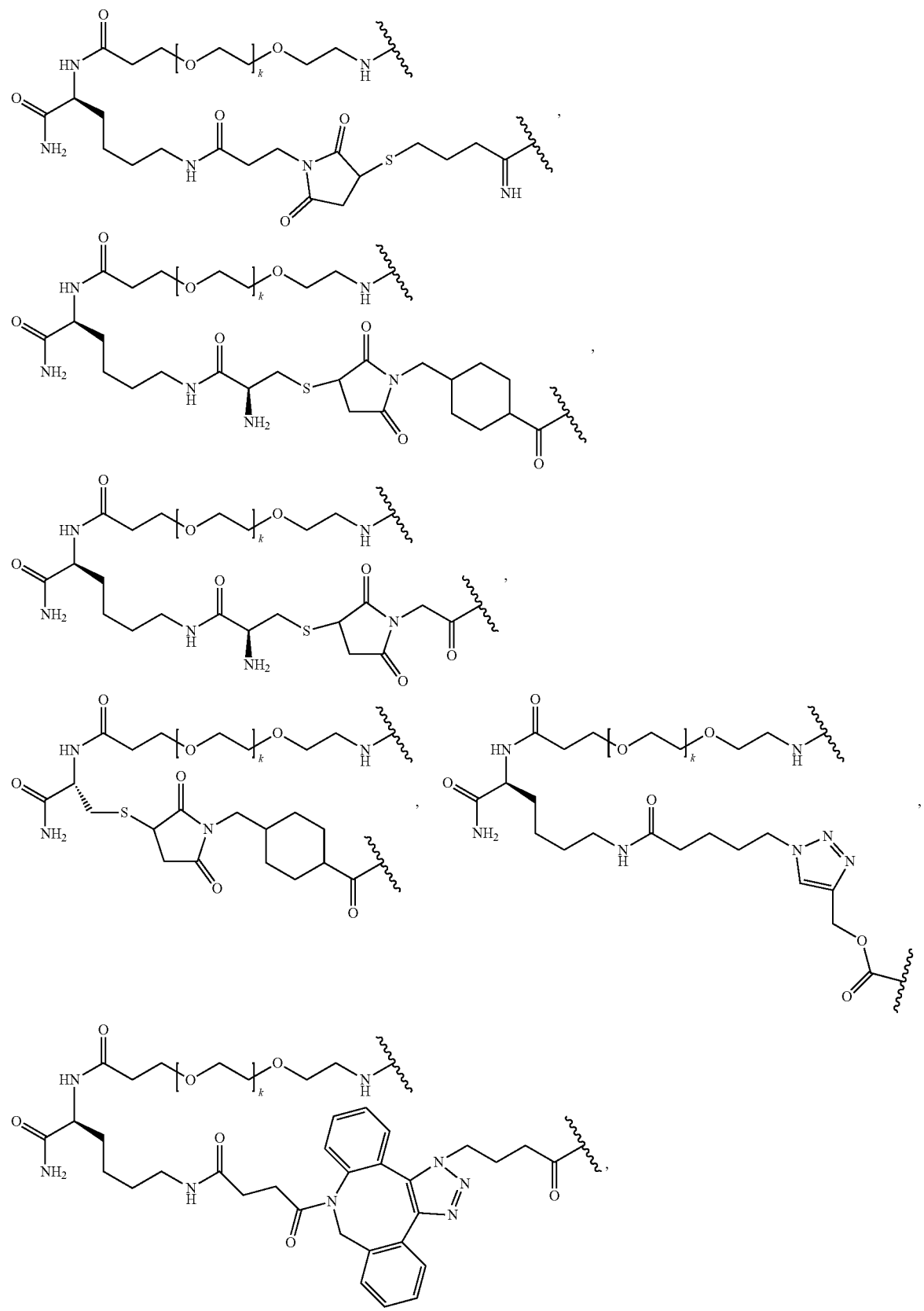

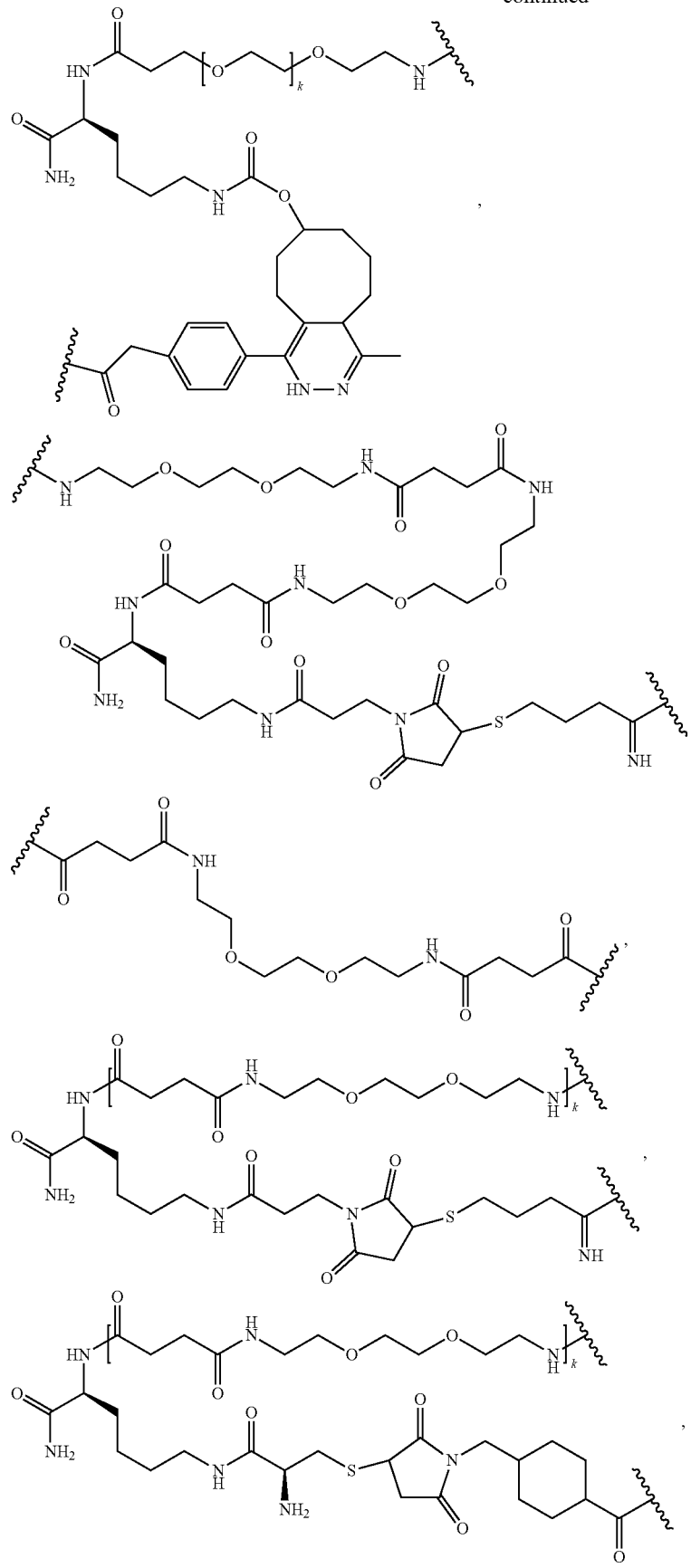

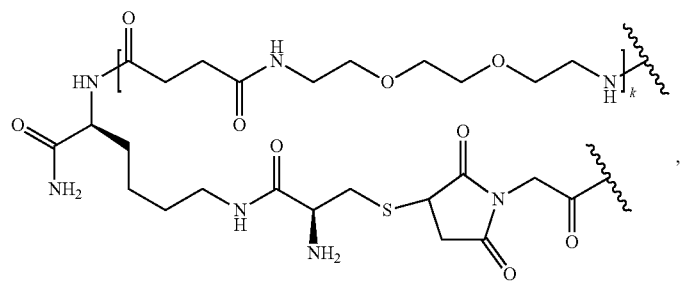
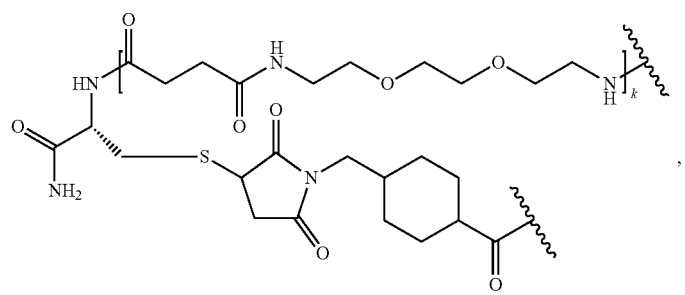
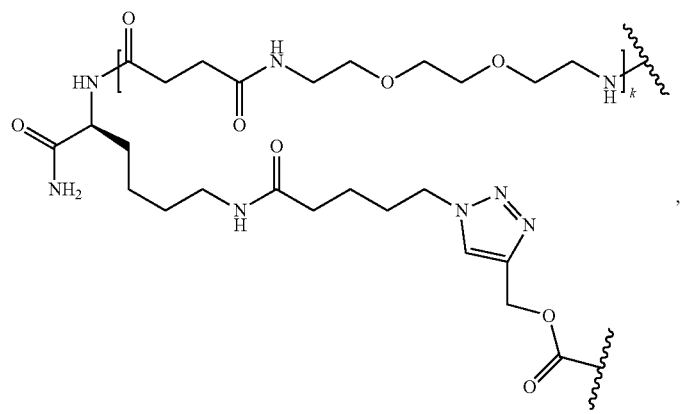
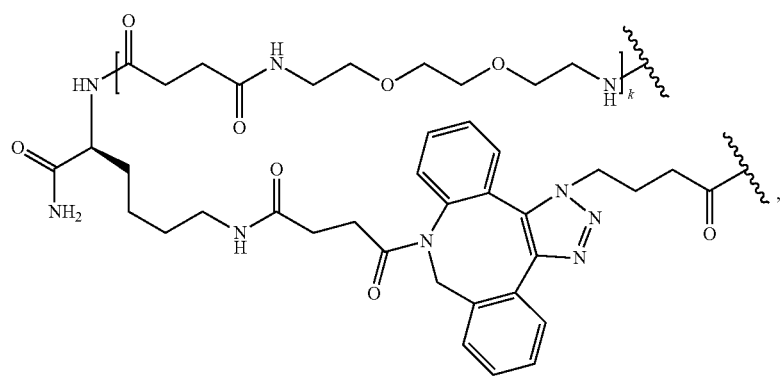

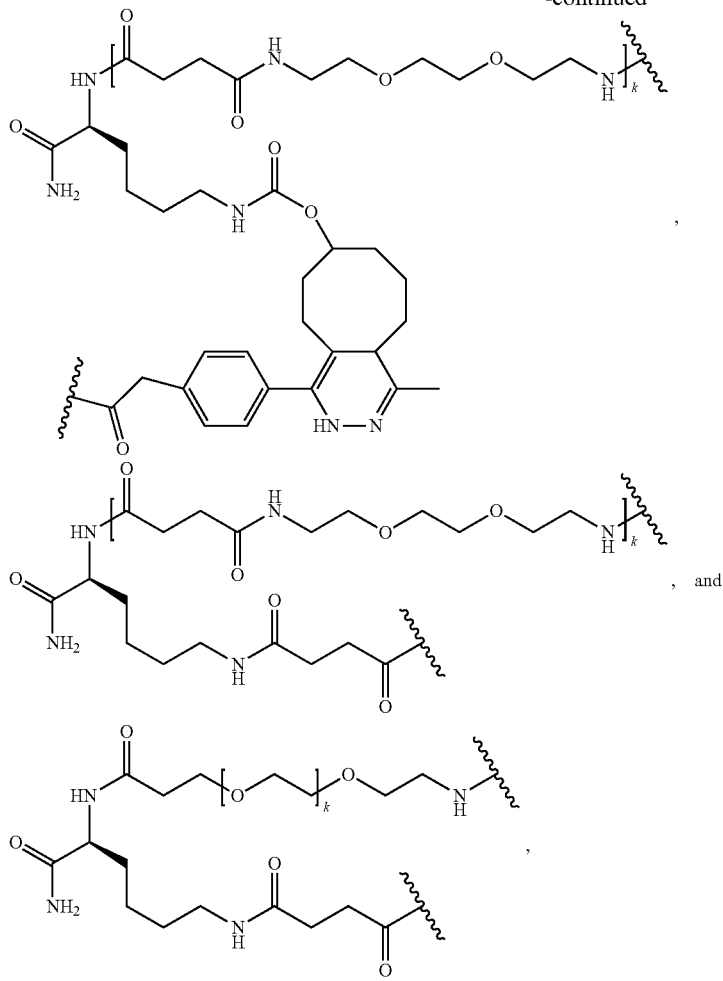

wherein k is from 0 to 6.

The D moiety of Formula I, Formula Ia, and Formula II can be any suitable phosphonate drug including, but not limited to, monophosphonates, bisphosphonates, and trisphosphonates. In some embodiments, the D moiety of Formula I, Formula Ia, and Formula II is a phosphonate or bisphosphonate compound. In some embodiments, the D moiety of Formula I, Formula Ia, and Formula II is a bisphosphonate compound. In some embodiments, the D moiety is a bisphosphonate compound such as, but not limited to, Etidronate (Didronel), Clodronate (Bonefos, Loron), Tiludronate (Skelid), Pamidronate (APD, Aredia), Neridronate, Olpadronate, Alendronate (Fosamax), Ibandronate (Boniva), Risedronate (Actonel) and Zoledronate (Zometa). Additional bisphosphonates are described below in greater detail. One of skill in the art will appreciate that other bisphosphonates are useful in the present invention.

In some embodiments, the D moiety of Formula I, Formula Ia, and Formula II has the formula:

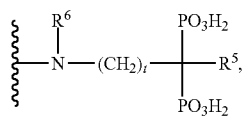

wherein $R^5$ is selected from H, OH and halogen; $R^6$ is selected from H and $C_{1-6}$ alkyl; and subscript t is from 1 to 6.

In some other embodiments, the D moiety of Formula I, Formula Ia, and Formula II has the formula selected from:

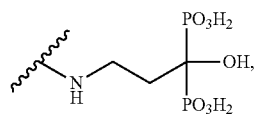

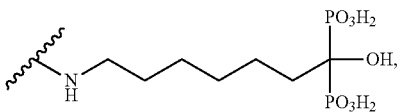

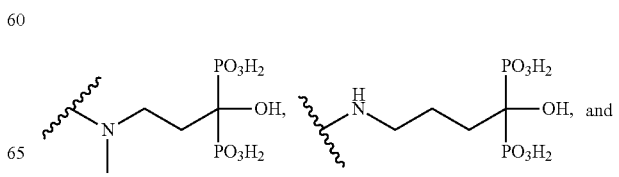

-continued
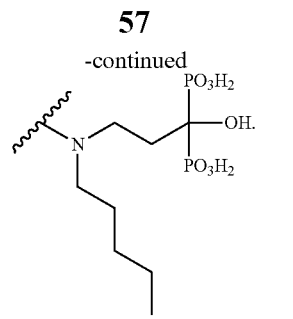
In some embodiments, the compounds of Formula I, Formula Ia, and Formula II are selected from:

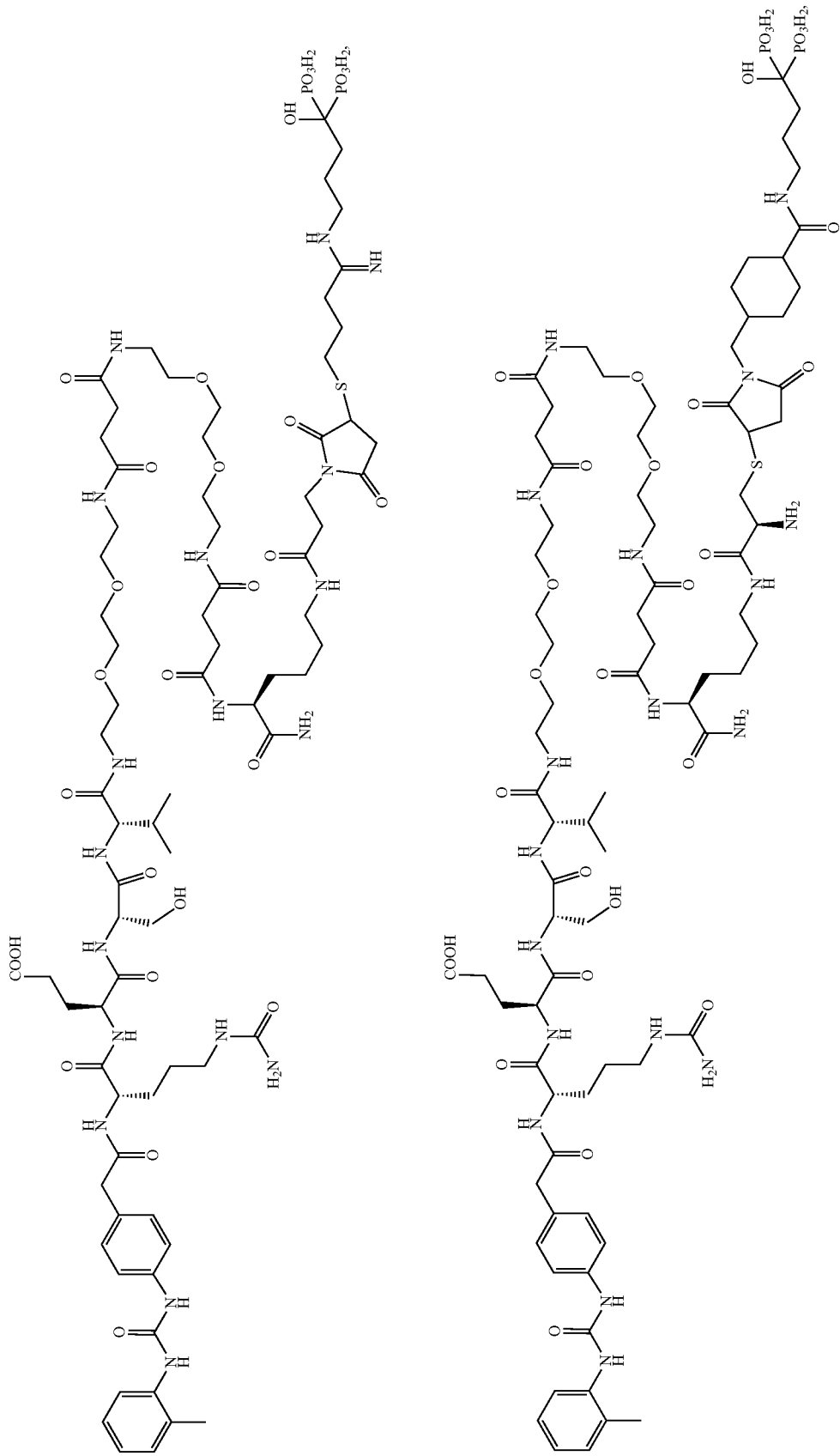

-continued
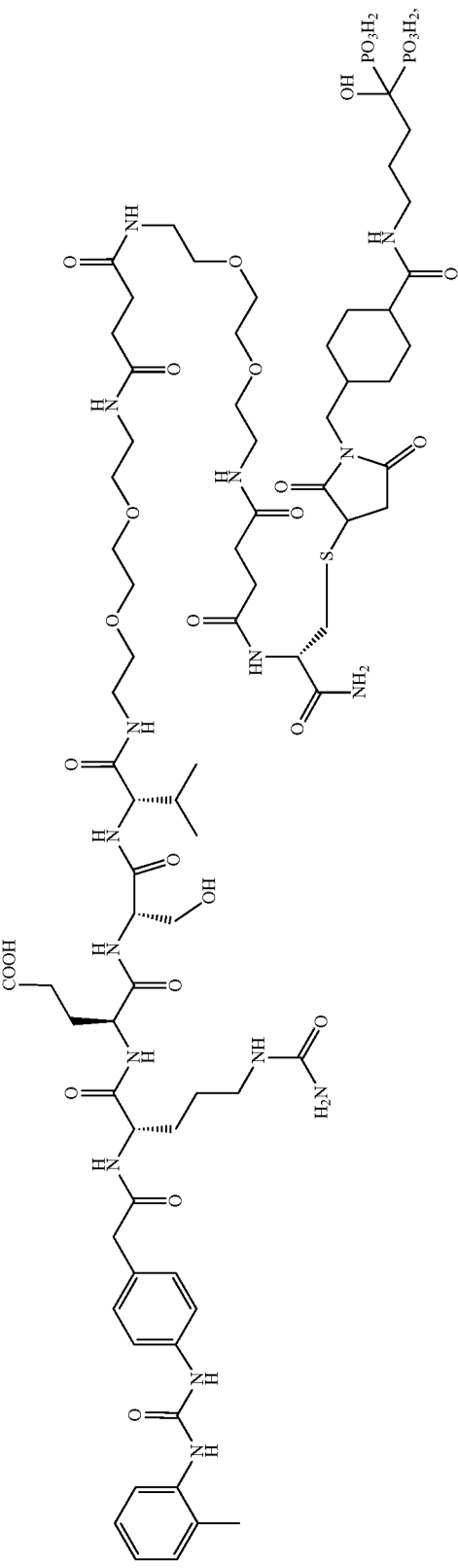 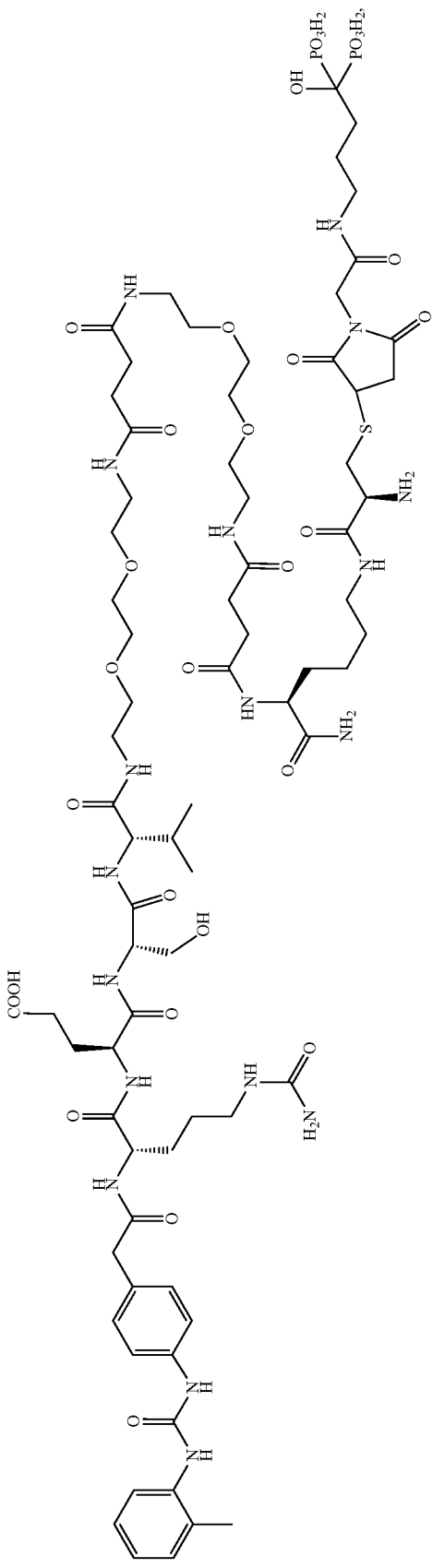

-continued
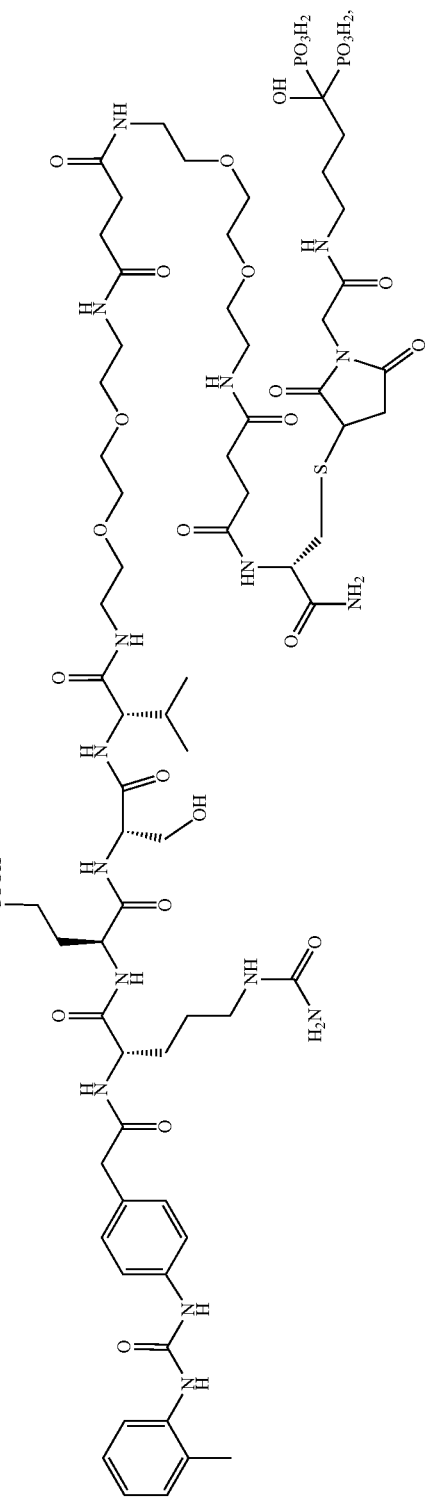
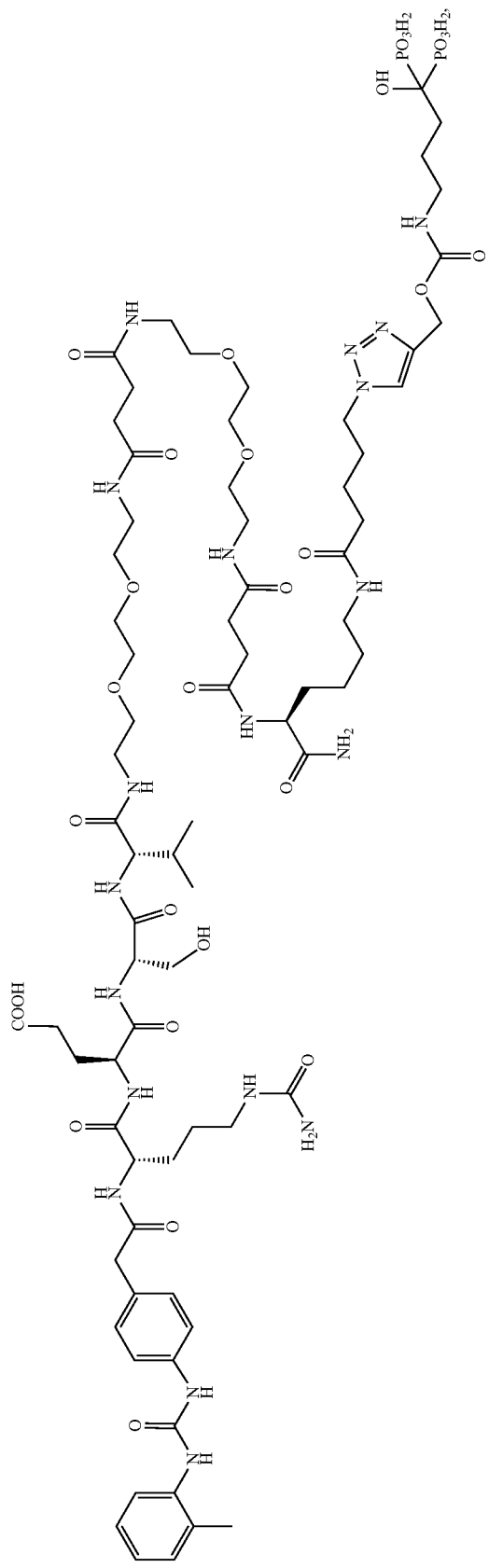

-continued
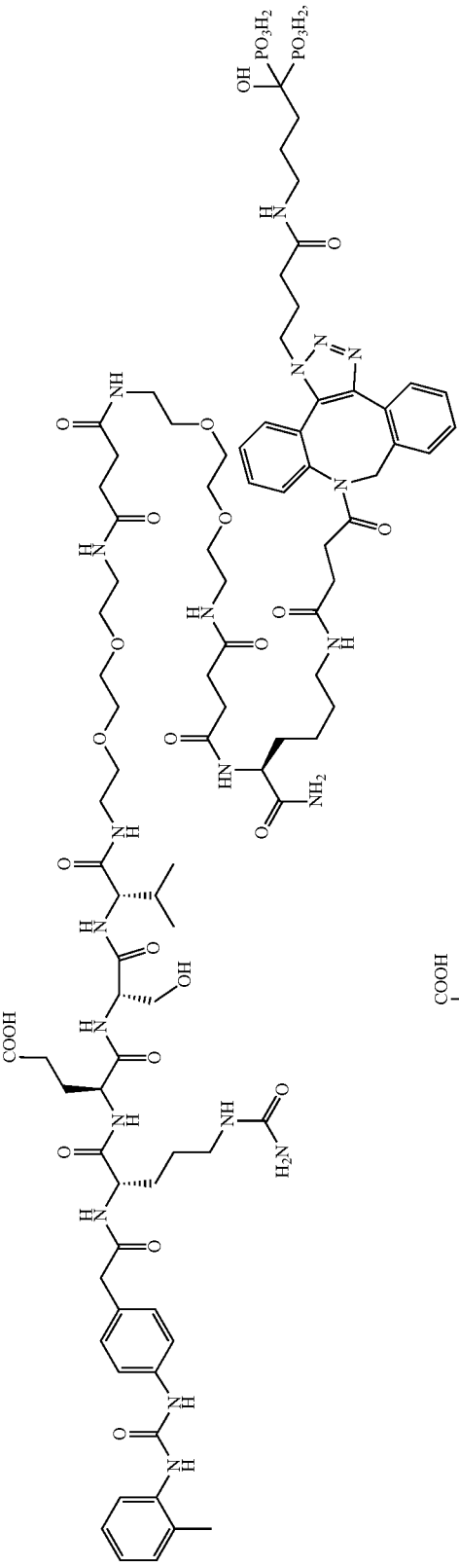
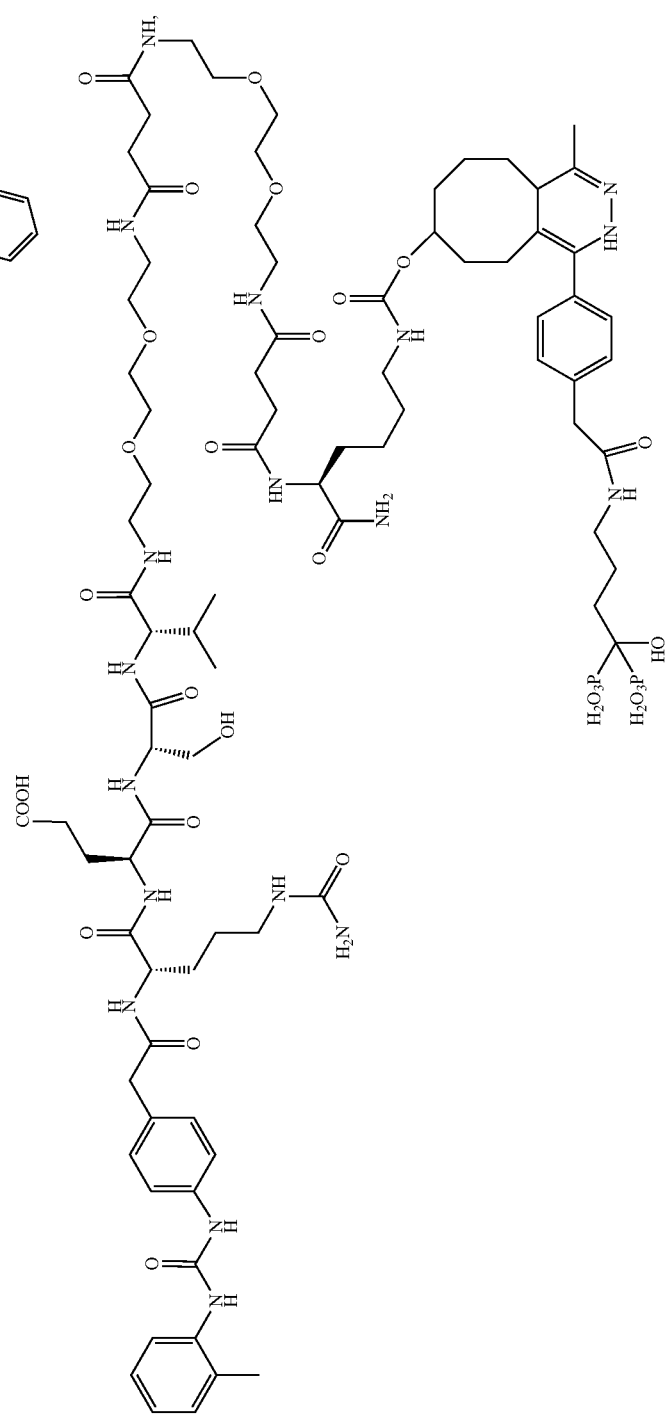

-continued
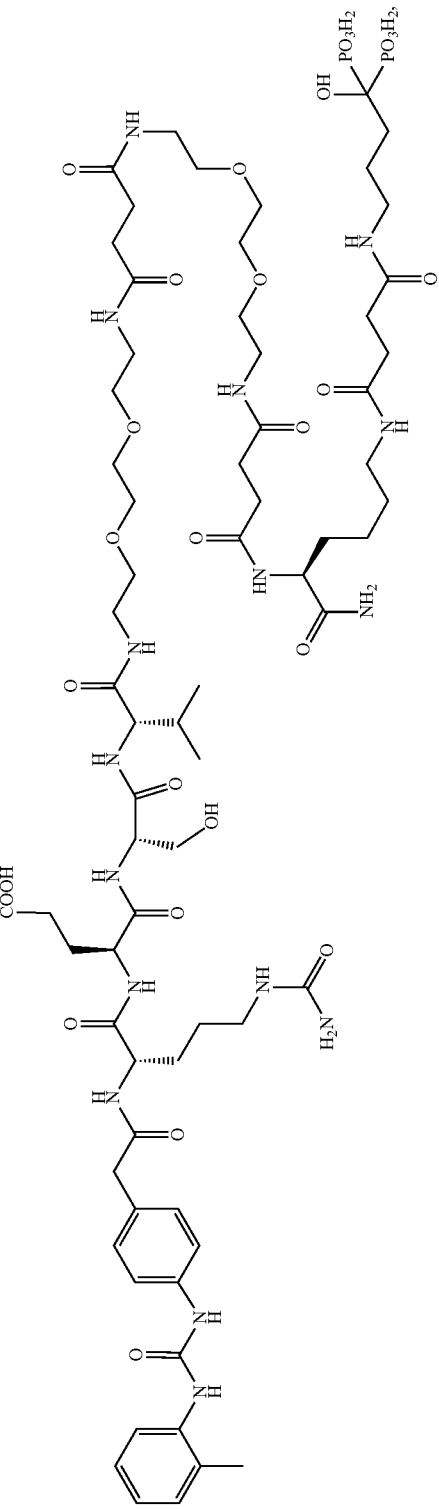
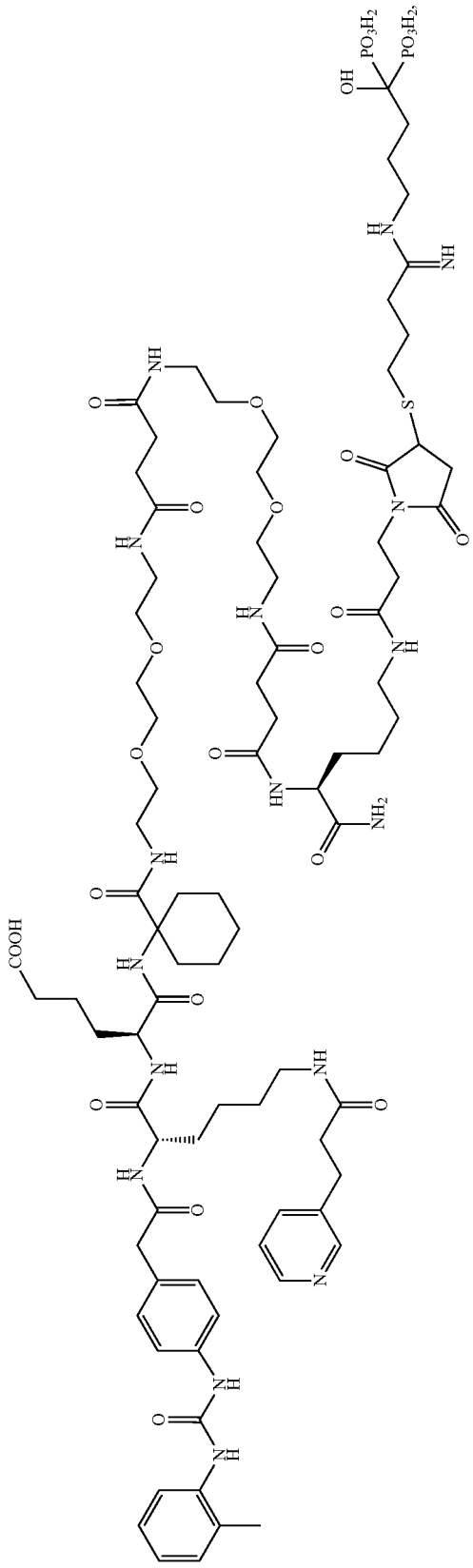

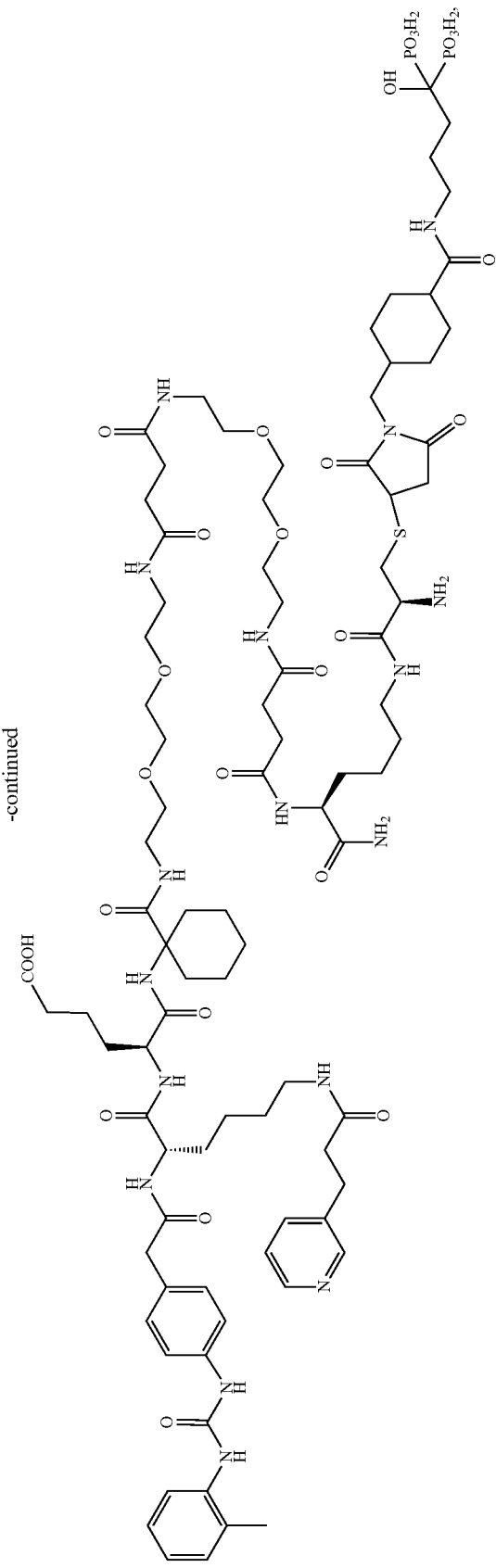
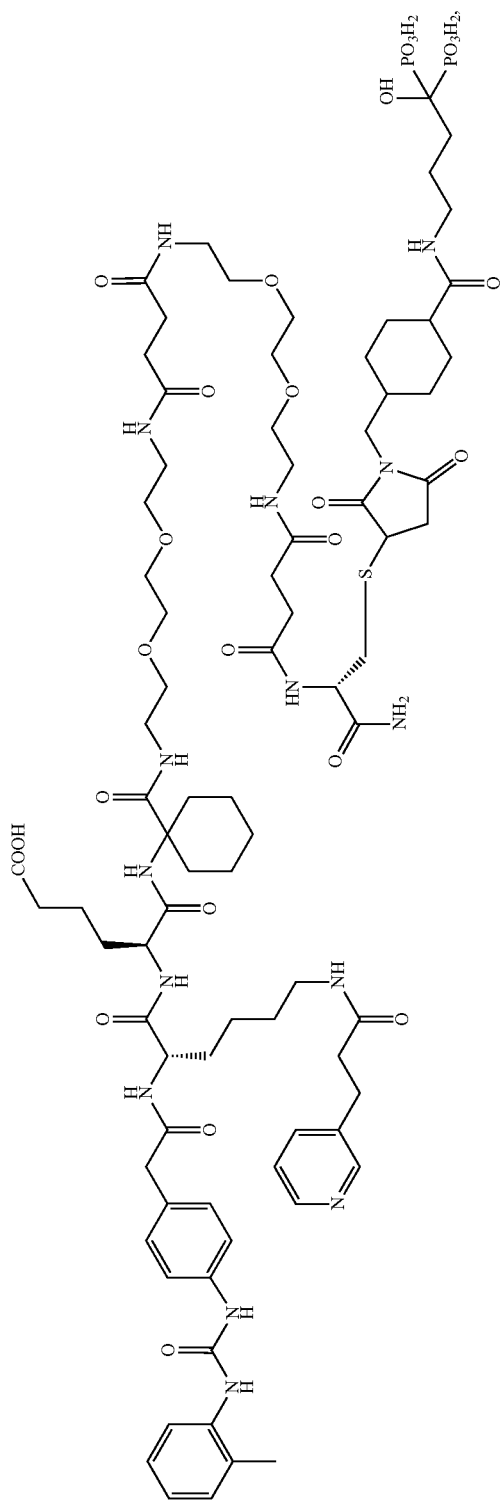

-continued
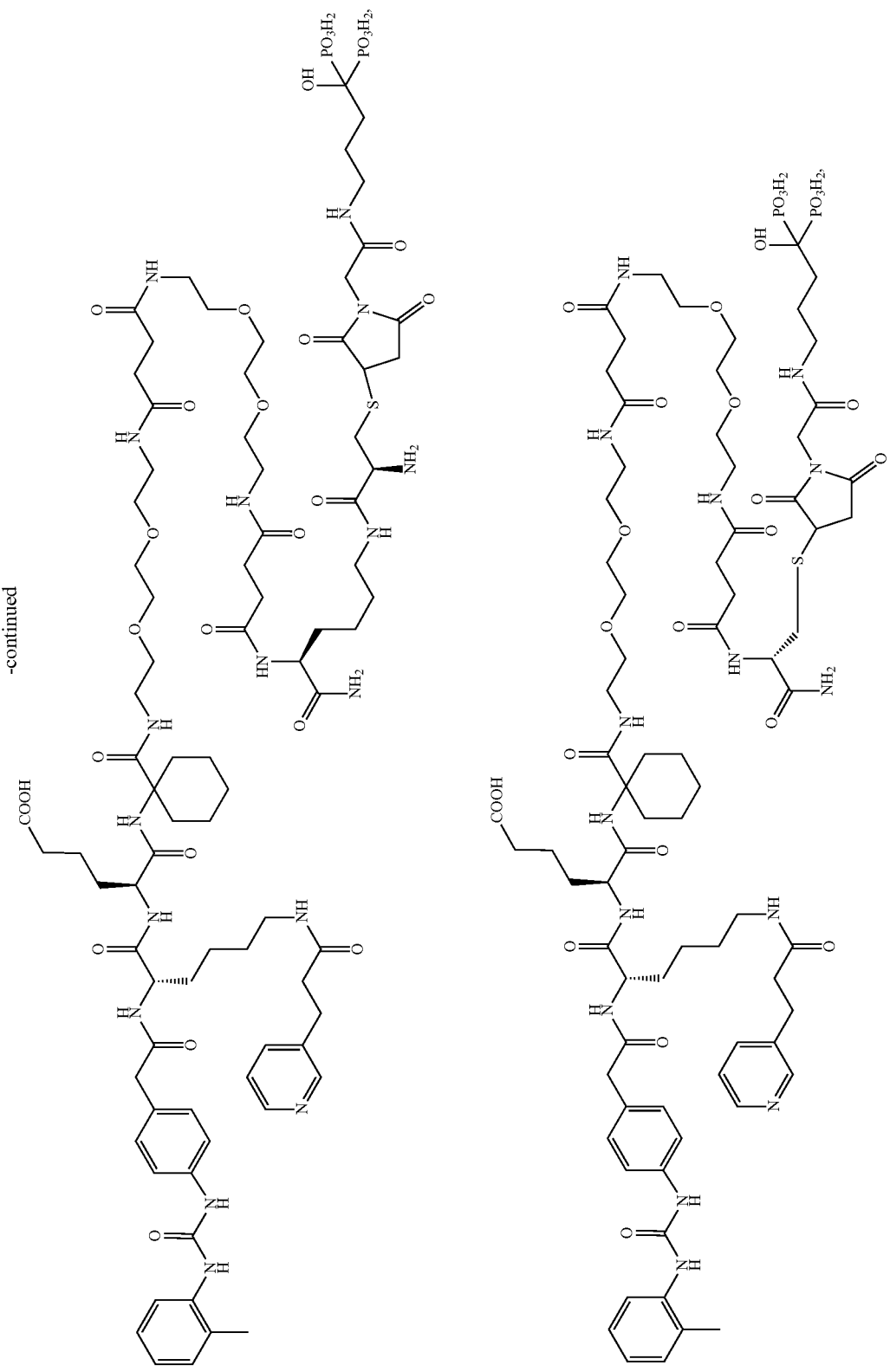

-continued
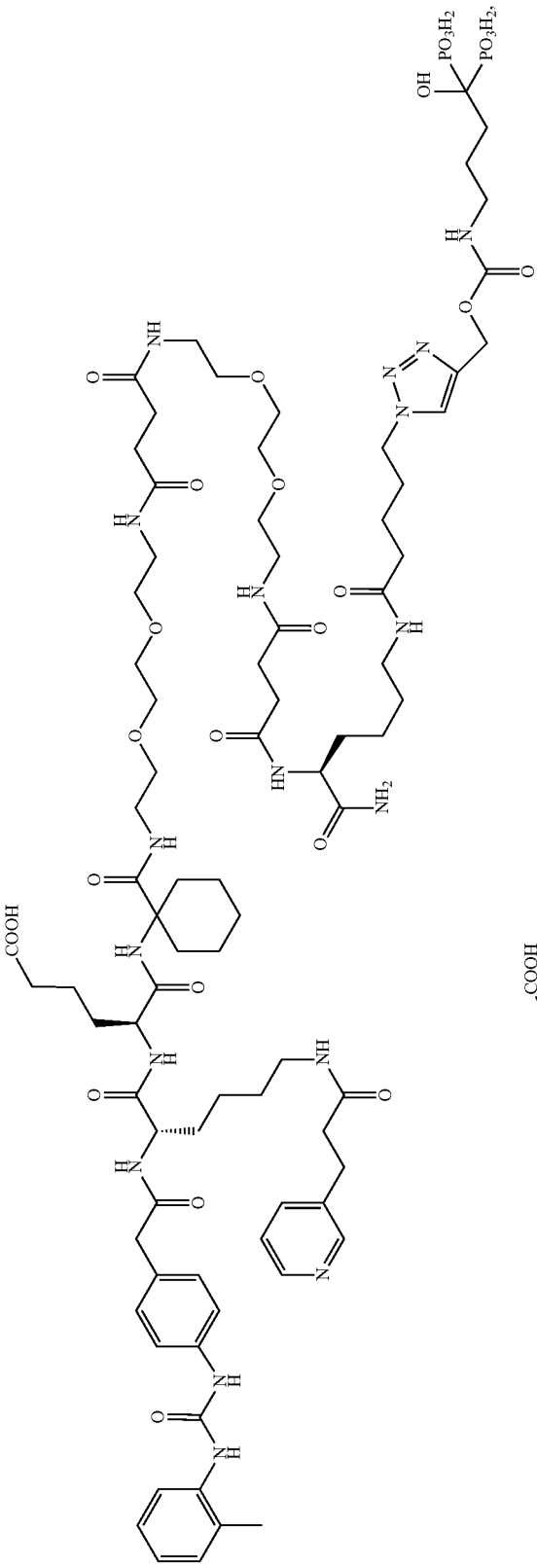
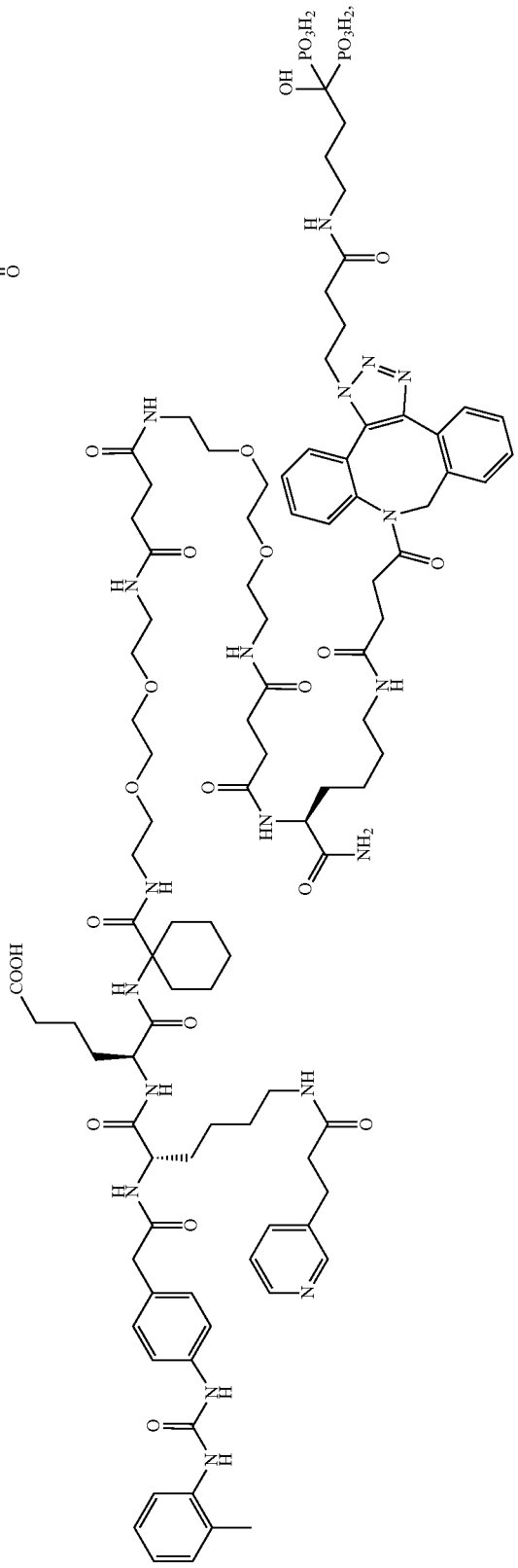

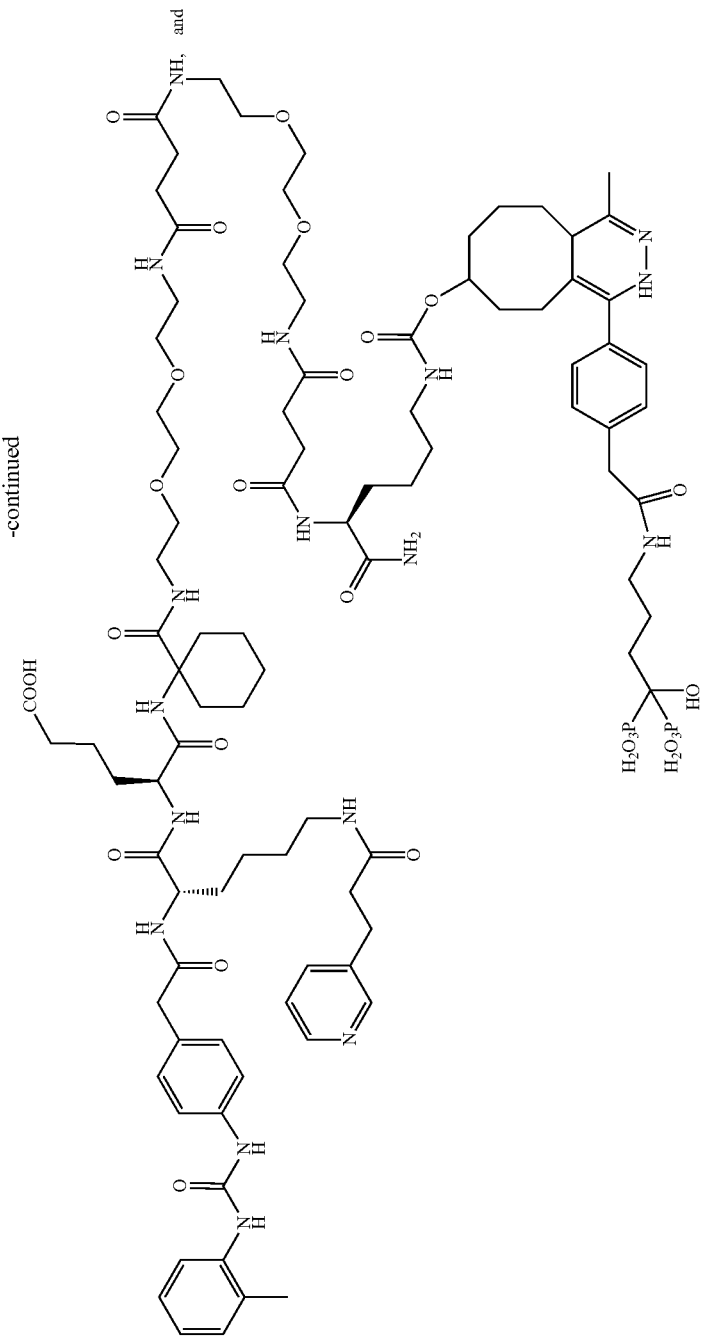

-continued
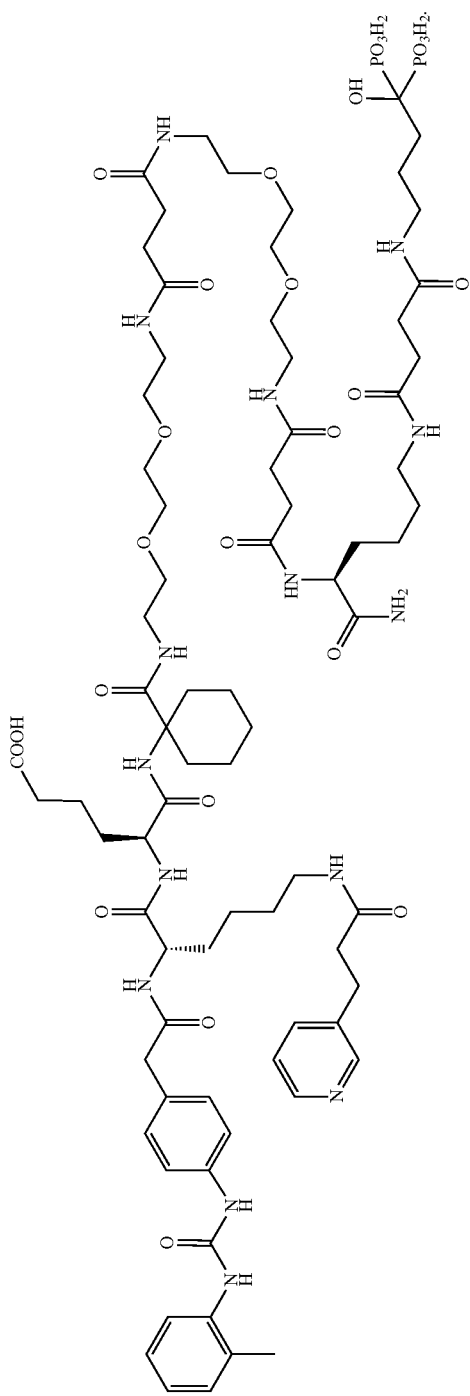

In some embodiments, the compounds of Formula I, Formula Ia, and Formula II are selected from:

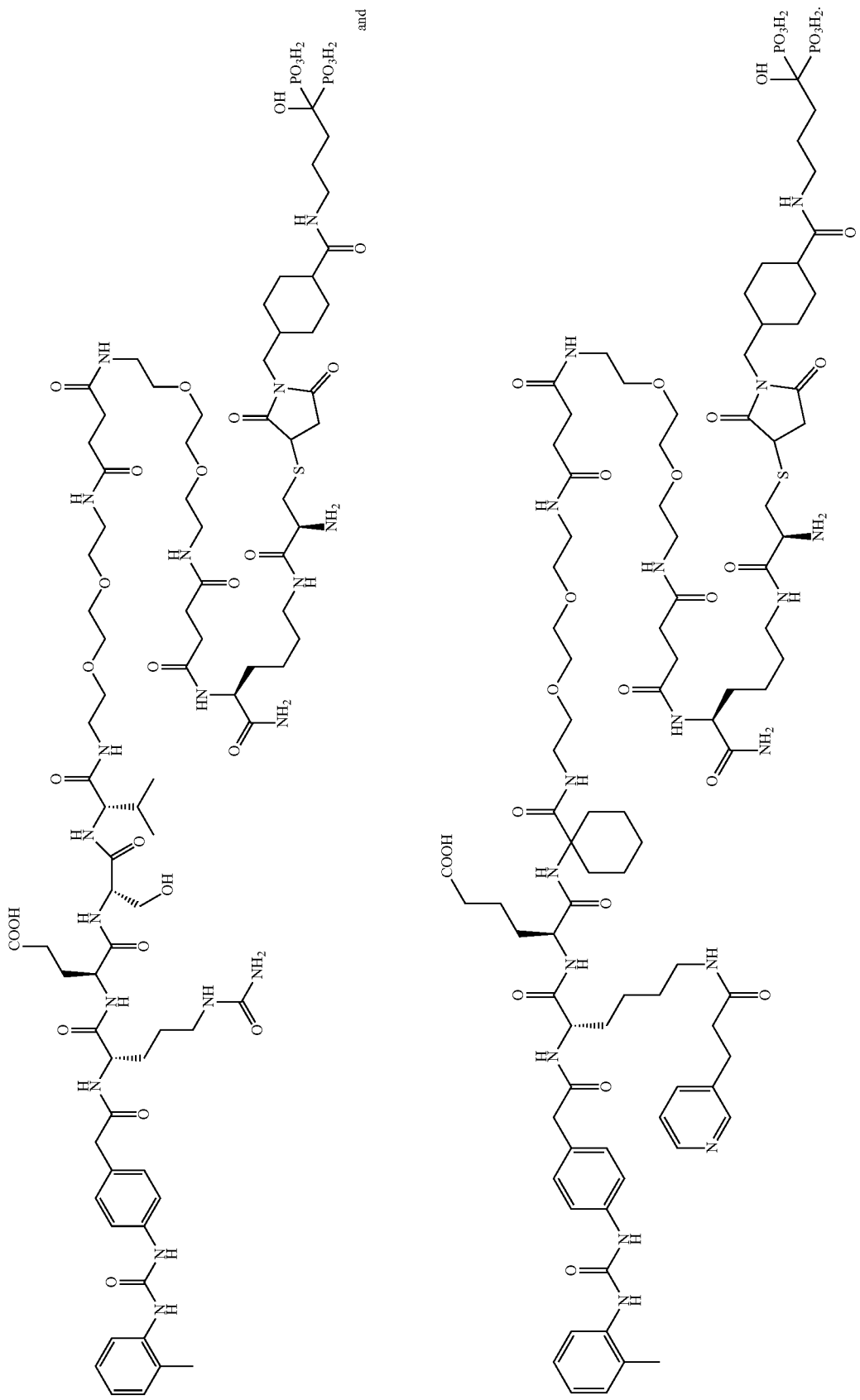

In some embodiments, the salts, hydrates, solvates, prodrug forms, isomers, and metabolites of compounds of Formula I, Formula Ia, and Formula II are provided.

In some embodiments, the invention provides isomers or pharmaceutically acceptable salts of the compounds of Formula I, Formula Ia, and Formula II. Salts include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Other salts include, but are not limited to, salts with inorganic bases including alkali metal salts such as sodium salts, lithium salts, and potassium salts; alkaline earth metal salts such as calcium salts, and magnesium salts; aluminum salts; and ammonium salts, such as ammonium, trimethyl-ammonium, diethylammonium, and tris-(hydroxymethyl)-methyl-ammonium salts. Other salts with organic bases include salts with diethylamine, diethanolamine, meglumine, and N,N'-dibenzylethylenediamine. Acid addition salts, such as mineral acids, organic carboxylic and organic sulfonic acids, e.g., hydrochloric acid, methanesulfonic acid, maleic acid, are also possible provided a basic group, such as pyridyl, constitutes part of the structure.

The neutral forms of the compounds of Formula I, Formula Ia, and Formula II can be regenerated by contacting the pharmaceutically acceptable salt of Formula I, Formula Ia, or Formula II with a base or acid and isolating the parent compound in the conventional manner. The parent form of the compound of Formula I, Formula Ia, and Formula II differs from the various salt forms in certain physical properties, such as solubility in polar solvents, but otherwise the salts are equivalent to the parent form of the compound for the purposes of the present invention.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the enantiomers, racemates, diastereomers, tautomers, geometric isomers, stereoisomeric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques.

The present invention also provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The compounds of the invention can be synthesized by a variety of methods known to one of skill in the art (see Comprehensive Organic Transformations by Richard C. Larock, 1989) or by an appropriate combination of generally well known synthetic methods. Techniques useful in synthesizing the compounds of the invention are both readily apparent and accessible to those of skill in the relevant art. The discussion below is offered to illustrate certain of the diverse methods available for use in assembling the compounds of the invention. However, the discussion is not intended to define the scope of reactions or reaction sequences that are useful in preparing the compounds of the present invention. One of skill in the art will appreciate that other methods of making the compounds are useful in the present invention.

The "one-bead one-compound" (OBOC) combinatorial library method was first reported in 1991 (Lam et al., *Nature*, 1991, 354: p. 82-4). In essence, when a "split-mix" synthesis method (Lam et al., id; Houghten et al., *Nature*, 1991, 354: p. 84-6; Furka et al., *Int. J. Peptide Protein Res.*, 1991, 37: p. 487-93) is used to generate a combinatorial library, each bead expresses only one chemical entity (Lam et al., id; Lam et al., *Chem. Rev.*, 1997, 97: p. 411-48). Random libraries of millions of beads can then be screened in parallel for a specific acceptor molecule (e.g., receptor, antibody, enzyme, virus, whole cell, etc.). Positive beads are physically isolated for structural determination by microsequencing using automatic Edman degradation (Lam et al., *Nature*, 1991, 354: p. 82-4).

The one-bead-one compound (OBOC) combinatorial library method synthesizes millions of compounds such that each bead displays only one compound. One example of a compound identified through the OBOC combinatorial library methods is LLP2A, which specifically binds to the integrin $\alpha_4\beta_1$ ($IC_{50}$=2 pM). LLP2A, when conjugated a to near-infrared fluorescent dye, can be used to image $\alpha_4\beta_1$-expressing cells with high sensitivity and specificity and to guide a therapeutic compound to the $\alpha_4\beta_1$-expressing lymphomas (Peng, L., et al., *Nat Chem Biol*, 2006, 2(7): p. 381-9). The ligand is known to direct compounds to the $\alpha_4\beta_1$-expressing lymphomas (Peng, L., et al., *Nat Chem Biol*, 2006, 2(7): p. 381-9; Peng, L., et al., Mol Cancer Ther, 2008, 7(2): p. 432-7 Aina, O. H., et al., Mol Pharm, 2007. 4(5): p. 631-51; Aina, O. H., et al., Mol Cancer Ther, 2005. 4(5): p. 806-13.).

The compounds described herein can be used in combination with one another, with other active agents known to be useful in treating osteoporosis or promoting bone growth, or with adjunctive agents that may not be effective alone, but may contribute to the efficacy of the active agent. In some embodiments, co-administration of the compounds herein with other agents includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

III. PHARMACEUTICAL COMPOSITIONS AND METHODS OF ADMINISTRATION

In another embodiment, the present invention provides a pharmaceutical composition, including a compound of the present invention and a pharmaceutically acceptable excipient.

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intramuscularly, intracutaneously, subcutaneously, intraduodenally, or intraperitoneally. Also, the compounds described herein can be administered by inhalation, for example, intranasally. Additionally, the compounds of the present invention can be administered transdermally. The compounds of the present invention can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995).

The compositions typically include a conventional pharmaceutical carrier or excipient and may additionally include other medicinal agents, carriers, adjuvants, diluents, tissue permeation enhancers, solubilizers, and the like. In some embodiments, the composition will contain about 0.01% to about 90% (e.g., from about 0.1% to about 75%, or from about 0.1% to about 50%, or from about 0.1% to about 10%) by weight of the peptidomimetic ligand compound(s), with the remainder consisting of suitable pharmaceutical carrier and/or excipients. Appropriate excipients can be tailored to the particular composition and route of administration by methods well known in the art as described, e.g., by Remington, supra.

For oral administration, the compositions can be in the form of tablets, capsules, emulsions, suspensions, solutions, syrups, sprays, lozenges, powders, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the pharmaceutical compositions take the form of a pill, tablet, or capsule, and thus, the composition can contain, along with the ligands or combination of ligands, any of the following: a diluent such as lactose, sucrose, dicalcium phosphate, and the like; a disintegrant such as starch or derivatives thereof; a lubricant such as magnesium stearate and the like; and a binder such a starch, gum acacia, polyvinylpyrrolidone, gelatin, cellulose and derivatives thereof. The ligands can also be formulated into a suppository disposed, for example, in a polyethylene glycol (PEG) carrier.

Liquid compositions can be prepared by dissolving or dispersing a ligand or a combination of ligands and optionally one or more pharmaceutically acceptable adjuvants in a carrier such as, for example, aqueous saline (e.g., 0.9% w/v sodium chloride), aqueous dextrose, glycerol, ethanol, and the like, to form a solution or suspension, e.g., for oral, topical, or intravenous administration. The ligands of the present invention can also be formulated into a retention enema.

For topical administration, the compositions of the present invention can be in the form of emulsions, lotions, gels, creams, jellies, solutions, suspensions, ointments, and transdermal patches. For delivery by inhalation, the composition can be delivered as a dry powder or in liquid form via a nebulizer. For parenteral administration, the compositions can be in the form of sterile injectable solutions and sterile packaged powders. Injectable solutions may be formulated in some embodiments at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

In powders, the carrier is a finely divided solid, which is in a mixture with the finely divided active component. In tablets, the active component is mixed with the carrier having the necessary binding properties in suitable proportions and compacted in the shape and size desired. Suitable solid excipients include, but are not limited to, magnesium carbonate; magnesium stearate; calcium phosphate; calcium silicate; talc; pectin; dextran, dextrin, and cyclodextrin inclusion complexes; a low melting wax; cocoa butter; carbohydrates; sugars including, but not limited to, lactose, dextrose, sucrose, mannitol, or sorbitol; starches including, but not limited to, starch from corn, wheat, rice, potato, or other plants; cellulose such as methyl cellulose, hydroxypropylmethyl-cellulose, or sodium carboxymethylcellulose; and gums including arabic, tragacanth, and acacia; as well as proteins including, but not limited to, gelatin, collagen; microcrystalline cellulose, water, saline, syrup, ethylcellulose, and polyacrylic acids such as Carbopols, e.g., Carbopol 941, Carbopol 980, Carbopol 981, etc.; lubricating agents; mineral oil; wetting agents; emulsifying agents; suspending agents; preserving agents such as methyl-, ethyl-, and propyl-hydroxy-benzoates (i.e., the parabens); pH adjusting agents such as inorganic and organic acids and bases; sweetening agents; and flavoring agents; biodegradable polymer beads. If desired, disintegrating or solubilizing agents may be added, such as the cross-linked polyvinyl pyrrolidone, agar, alginic acid, alginates, or a salt thereof, such as sodium alginate.

A pharmaceutically acceptable carrier may include physiologically acceptable compounds that act, for example, to stabilize the compounds of the present invention or modulate their absorption, or other excipients as desired. Physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the compounds of the present invention and on the particular physio-chemical characteristics of the compounds of the present invention. Generally, such carriers should be nontoxic to recipients at the dosages and concentrations employed. Ordinarily, the preparation of such compositions entails combining the therapeutic agent with buffers, antioxidants such as ascorbic acid, low molecular weight (less than about 10 residues) polypeptides, proteins, amino acids, carbohydrates including glucose, maltose, sucrose or dextrins, chelating agents such as EDTA, glutathione and other stabilizers and excipients. Neutral buffered saline or saline mixed with nonspecific serum albumin are exemplary appropriate diluents.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain compounds of the present invention mixed with a filler or binders such as lactose or starches, lubricants such as talc or magnesium stearate, and, optionally, stabilizers. In soft capsules, the compounds of the present invention may be dissolved or suspended in suitable liquids, such as fatty oils, liquid paraffin, or liquid polyethylene glycol with or without stabilizers.

Some slow release embodiments include polymeric substances that are biodegradable and/or dissolve slowly. Such polymeric substances include polyvinylpyrrolidone, low- and medium-molecular-weight hydroxypropyl cellulose and hydroxypropyl methylcellulose, cross-linked sodium carboxymethylcellulose, carboxymethyl starch, potassium methacrylatedivinylbenzene copolymer, polyvinyl alcohols, starches, starch derivatives, microcrystalline cellulose, ethylcellulose, methylcellulose, and cellulose derivatives, β-cyclodextrin, poly(methyl vinyl ethers/maleic anhydride), glucans, scierozlucans, mannans, xanthans, alzinic acid and derivatives thereof, dextrin derivatives, glyceryl monostearate, semisynthetic glycerides, glyceryl palmitostearate, glyceryl behenate, polyvinylpyrrolidone, gelatine, agnesium stearate, stearic acid, sodium stearate, talc, sodium benzoate, boric acid, and colloidal silica.

Slow release agents of the invention may also include adjuvants such as starch, pregelled starch, calcium phosphate mannitol, lactose, saccharose, glucose, sorbitol, microcrystalline cellulose, gelatin, polyvinylpyrrolidone, methylcellulose, starch solution, ethylcellulose, arabic gum, tragacanth gum, magnesium stearate, stearic acid, colloidal silica, glyceryl monostearate, hydrogenated castor oil, waxes, and mono-, bi-, and trisubstituted glycerides. Slow release agents may also be prepared as generally described in WO94/06416.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a compound of the present invention in a vegetable oil, such as *arachis* oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

In some embodiments, the pharmaceutical preparation is in unit dosage form. The term "unit dosage form" refers to physically discrete units suitable as unitary dosages for human subjects and other mammals (e.g., dogs), each unit containing a predetermined quantity of active material calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of a ligand or a combination of ligands. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents. Certain pharmaceutical preparations can deliver the compounds of the invention in a sustained release formulation.

IV. ADMINISTRATION AND METHODS OF TREATMENT

Administration of the ligands of the present invention with a suitable pharmaceutical excipient as necessary can be carried out via any of the accepted modes of administration. Thus, administration can be, for example, intravenous, topical, subcutaneous, transcutaneous, transdermal, intramuscular, oral, intra joint, parenteral, intra-arteriole, intradermal, intraventricular, intracranial, intraperitoneal, intralesional, intranasal, rectal, vaginal, or by inhalation. Administration may also be directly to the bone surface and/or into tissues surrounding the bone. The formulations may take any of the solid forms, semi-solid forms, or liquid dosage forms described above, such as, for example, tablets, pills, capsules, powders, solutions, suspensions, emulsions, suppositories, retention enemas, creams, ointments, lotions, gels, aerosols, or the like.

The pharmaceutical preparations are typically delivered to a mammal, including humans and non-human mammals. Non-human mammals treated using the present methods include domesticated animals (i.e., canine, feline, murine, rodentia, and lagomorpha) and agricultural animals (bovine, equine, ovine, porcine). Local increase in bone can be used for fracture healing, fusion (arthrodesis), orthopedic reconstruction, and periodontal repair. Systemic increase in bone can be used for the treatment of low bone mass, i.e., osteopenia.

Generally, administered dosages will be effective to deliver picomolar to micromolar concentrations of the ligand to the appropriate site or sites. However, one of ordinary skill in the art understands that the dose administered will vary depending on a number of factors, including, but not limited to, the particular ligand or set of ligands to be administered, the mode of administration, the type of application (e.g., imaging, therapeutic), the age of the patient, and the physical condition of the patient. Preferably, the smallest dose and concentration required to produce the desired result should be used. Dosage should be appropriately adjusted for children, the elderly, debilitated patients, and patients with cardiac and/or liver disease. Further guidance can be obtained from studies known in the art using experimental animal models for evaluating dosage. However, the increased cell binding affinity and specificity associated with the ligands of the present invention permits a wider margin of safety for dosage concentrations and for repeated dosing.

Figures 7A, 7B:
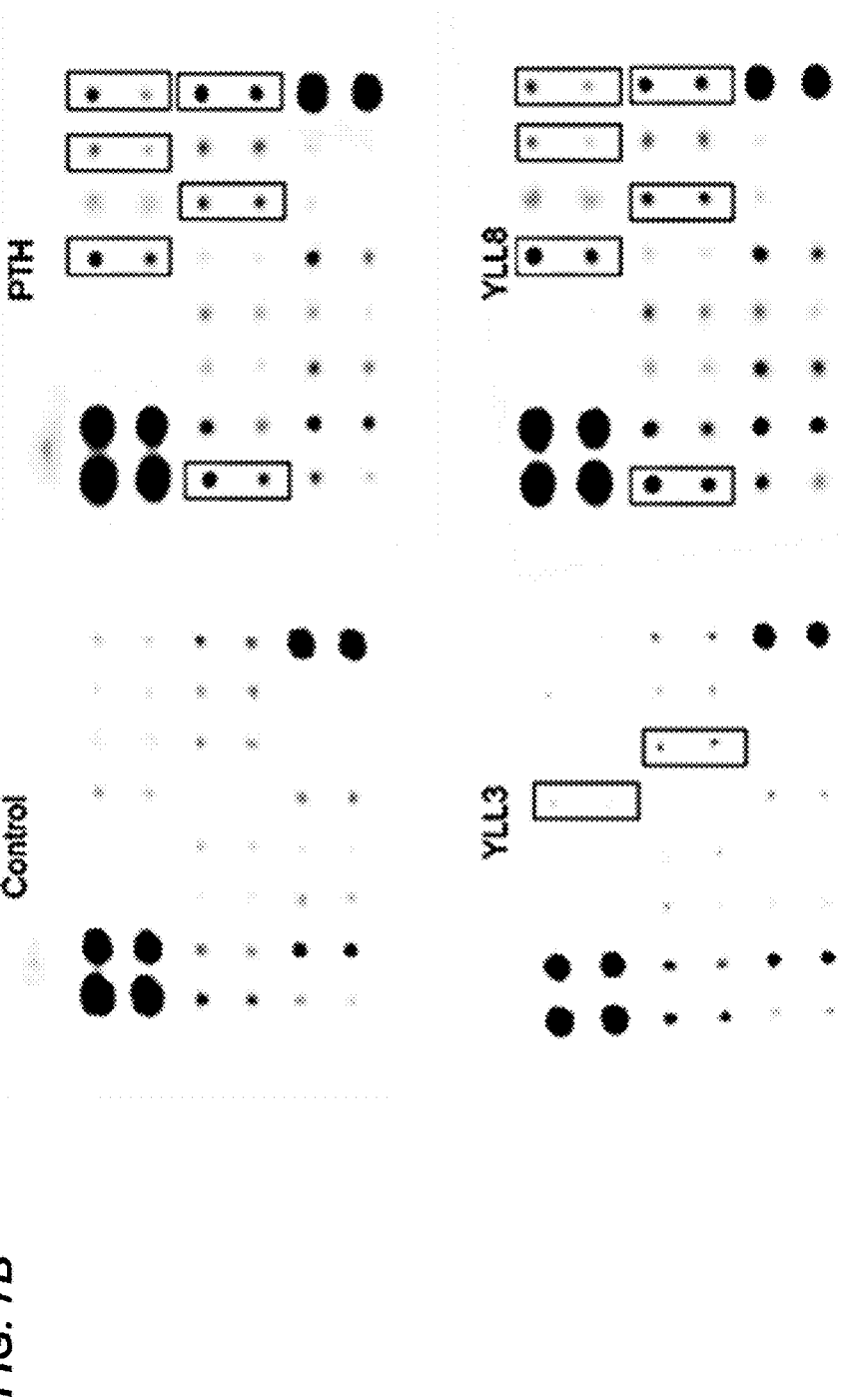
FIGS. 7A-7C show activation of Akt signaling using YLL8.
Figure 7C:
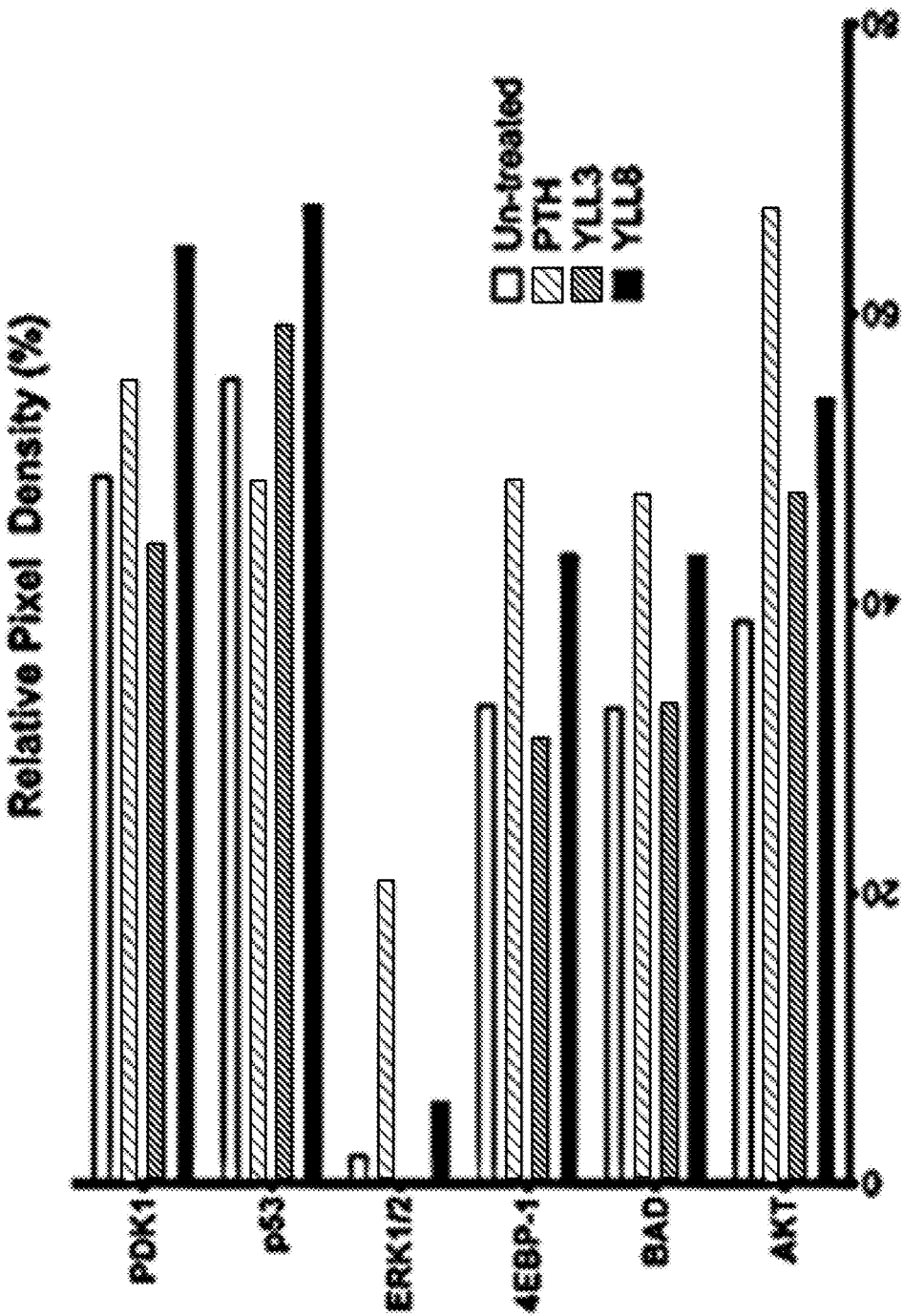

In some embodiments, the therapeutically effective amount is an amount that activates Akt signaling in the subject. Akt signaling and activation thereof can be assessed, for example, in bone marrow stromal cells using an Akt signaling array as depicted in FIGS. 7A-7C. Typically, the peptidomimetic ligand compound(s) will be administered at a dose ranging from about 0.01 milligrams to about 1000 milligrams per kilogram of a subject's body weight (i.e., about 0.01-1000 mg/kg). The dose of the compound can be, for example, about 0.01-1000 mg/kg, or about 0.1-250 mg/kg, or about 0.2-100 mg/kg. The dose of the compound can be about 0.1, 0.2, 0.3, 0.4, 0.5, 1, 5, 10, 25, 50, 75, 100, 200, 300, 400, 500, 600, 700, 800, 900, or 1000 mg/kg. The dosages can be varied depending upon the requirements of the patient, the severity of the disorder being treated, and the particular formulation being administered. The size of the dose will also be determined by the existence, nature, and extent of any adverse side-effects that accompany the administration of the drug in a particular patient. The total dosage can be divided and administered in portions over a period of time suitable to treat to the condition or disorder.

The compounds can be administered for periods of time which will vary depending upon the nature of the particular disorder, its severity, and the overall condition of the subject to whom the compound is administered. Compositions containing a ligand or a combination of ligands of the present invention may be administered repeatedly, e.g., at least 2, 3, 4, 5, 6, 7, 8, or more times, or the composition may be administered by continuous infusion. Administration can be conducted, for example, hourly, every 2 hours, three hours, four hours, six hours, eight hours, or twice daily including every 12 hours, or any intervening interval thereof. Administration can be conducted once daily, or once every 36 hours or 48 hours, or once every month or several months. Following treatment, a subject can be monitored for changes in his or her condition and for alleviation of the symptoms of the disorder. The dosage of the compound can either be increased in the event the subject does not respond significantly to a particular dosage level, or the dose can be decreased if an alleviation of the symptoms of the disorder is observed, or if the disorder has been remedied, or if unacceptable side effects are seen with a particular dosage.

In practicing the methods of the present invention, the pharmaceutical compositions can be used alone, or in combination with other therapeutic or diagnostic agents. The additional drugs used in the combination protocols of the present invention can be administered separately or one or more of the drugs used in the combination protocols can be administered together, such as in an admixture. Where one or more drugs are administered separately, the timing and schedule of administration of each drug can vary. The other therapeutic or diagnostic agents can be administered at the same time as the compounds of the present invention, separately or at different times.

In some embodiments, the present invention provides a method of promoting systemic bone growth. Systemic bone growth refers to the growth of bone throughout the subject, and can affect all the bones in the subject's body. A subject in need of systemic bone growth can suffer from a variety of ailments and disease states. In some embodiments, the subject suffers from a low bone mass phenotype disease. Low bone mass can be determined by a variety of methods known to one of skill in the art. For example, low bone mass can be characterized by a T-score less than about −1. Low bone mass phenotype diseases can include osteoporosis, osteopenia, and osteoporosis-pseudoglioma syndrome (OPPG). In some other embodiments, the low bone mass phenotype disease can be osteopenia or osteoporosis-pseudoglioma syndrome (OPPG). In some other embodiments, the present invention provides a method of treating low bone mass by administering to a subject in need thereof a therapeutically effective amount of a compound of the present invention.

Following administration of the compounds of the present invention, systemic bone growth can be determined by a variety of methods, such as improvements in bone density. Bone density can be measured by a variety of different methods, including the T-score and Z-score. The T-score is the number of standard deviations above or below the mean for a healthy 30 year old adult of the same sex as the patient. Low bone mass is characterized by a T-score of −1 to -2.15. Osteoporosis is characterized by a T-score less than −2.15. The Z-score is the number of standard deviations above or below the mean for the patient's age and sex. Improvement in the T-score or Z-score indicate bone growth. Bone density can be measured in a variety of places of the skeleton, such the spine or the hip. One of skill in the art will appreciate that other methods of determining bone density are useful in the present invention.

In some embodiments, the present invention provides a method of treating osteoporosis, wherein the method includes administering to a subject in need thereof, a therapeutically effective amount of a compound of Formula I, Formula Ia, Formula Ib, Formula II, or pharmaceutically acceptable salts thereof.

The present invention also provides methods of treating diseases characterized by secondary-induced osteoporosis ("secondary low bone mass"), but not limited to, osteomalacia, polyostotic fibrous dysplasia, Paget's disease, rheumatoid arthritis, zero gravity, osteoarthritis, prolonged inactivity or immobility, osteomyelitis, celiac disease, Crohn's disease, ulcerative colitis, inflammatory bowel disease, gastrectomy, secondary-induced osteoporosis, amenorrhea, Cushing's disease, Cushing's syndrome, diabetes mellitus, diabetes, eating disorders, hyperparathyroidism, hyperthyroidism, hyperprolactinemia, Kleinefelter syndrome, thyroid disease, Turner syndrome, steroid-induced osteoporosis, seizure or depression-induced osteoporosis, immobility, arthritis, cancer-induced secondary osteoporosis, gonadotropin-releasing hormone agonist-induced low bone mass, thyroid medication-induced low bone mass, dilantin (phenytoin), depakote-induced low bone mass, chemotherapy-induced low bone mass, immunosuppressant-induced low bone mass, blood thinning agent-induced low bone mass, Grave's disease, juvenile rheumatoid arthritis, malabsorption syndromes, anorexia nervosa, kidney disease, anticonvulsant treatment (e.g., for epilepsy), corticosteroid treatment (e.g., for rheumatoid arthritis, asthma), Immunosuppressive treatment (e.g., for cancer), inadequate nutrition (especially calcium, vitamin D), excessive exercise leading to amenorrhea (absence of periods), smoking, and alcohol abuse, pregnancy-associated osteoporosis, copper deficiency, dibasic aminoaciduria type 2, Werner's syndrome, Hajdu-Cheney syndrome, hyperostosis corticalis deformans juvenilis, methylmalonic aciduria type 2, cystathionine beta-synthase deficiency, exemestane, hyperimmunoglobulin E (IgE) syndrome, Haemochromatosis, Singleton-Merten syndrome, beta thalassaemia (homozygous), reflex sympathetic osteodystrophy, sarcoidosis, Winchester syndrome, Hallermann-Streiff syndrome (HSS), cyproterone, glycerol kinase deficiency, Bonnet-Dechaume-Blanc syndrome, prednisolone, heparin, geroderma osteodysplastica, Torg osteolysis syndrome, orchidectomy, Fabry's disease, pseudoprogeria syndrome, Wolcott-Rallison syndrome, ankylosing spondylitis, myeloma, systemic infantile hyalinosis, Albright's hereditary osteodystrophy, autoimmune lymphoproliferative syndrome, Brown-Sequard syndrome, Diamond-Blackfan anemia, galactorrhoea-hyperprolactinaemia, gonadal dysgenesis, kidney conditions, Menkes disease, menopause, neuritis, ovarian insufficiency due to FSH resistance, familial ovarian insufficiency, premature aging, primary biliary cirrhosis, prolactinoma, familial prolactinoma, renal osteodystrophy, ulcerative colitis, underweight, Werner syndrome, bone tumor, bone cancer, brittle bone disease, osteogenesis imperfecta congenita, and osteogenesis imperfecta tarda. Other conditions include a bone injury, such as a fracture or weakened bone, or bone injured due to radiation treatment. One of skill in the art will appreciate that other types of conditions, diseases and treatments lead to osteoporosis.

Glucocorticoids are a class of corticosteroids, a type of steroid hormone, which are frequently used to treat diseases or conditions associated with an overactive immune system, such as, for example, asthma, allergies, asthma, autoimmune diseases (e.g., Grave's disease, rheumatoid arthritis, lupus, inflammatory bowel disease, etc.) and sepsis. However, using steroids or glucocorticoids can lead to rapid bone loss and result in a high incident fracture risk. In some cases, steroids or glucocorticoids (i.e., glucocorticosteroids) can cause osteonecrosis, the details of which are described below.

In some embodiments, the present invention provides a method of treating steroid-induced bone loss by administering to a subject in need thereof a therapeutically effective amount of a compound of Formula I, Formula Ia, Formula Ib, Formula II, or pharmaceutically acceptable salts thereof. In some embodiments, the present invention provides a method of treating glucocorticoid-induced bone loss by administering to a subject in need thereof a therapeutically effective amount of a compound of Formula I, Formula Ia, Formula Ib, Formula II, or pharmaceutically acceptable salts thereof. In some embodiments, the present invention provides a method of treating steroid-induced osteoporosis by administering to a subject in need thereof a therapeutically effective amount of a compound of Formula I, Formula Ia, Formula Ib, Formula II, or pharmaceutically acceptable salts thereof. In some embodiments, the present invention provides a method of treating glucocorticoid-induced osteoporosis by administering to a subject in need thereof a therapeutically effective amount of a compound of Formula I, Formula Ia, Formula Ib, Formula II, or pharmaceutically acceptable salts thereof.

Osteonecrosis, which is also called avascular necrosis or aseptic necrosis, is the death of bone cells in a bone due to decreased blood flow. If untreated, the death of the bone cells in the bone can lead to the collapse of areas of bone, which in turn, can lead to degenerative arthritis of joints near the bone. Osteonecrosis most commonly affects the hips and knees, but also can affect the shoulders, wrists, hands, ankles, feet, and jaw. Osteonecrosis can have various causes, including traumatic and non-traumatic causes. Typically in traumatic osteonecrosis, a serious trauma to a bone interrupts the bone's blood supply. Non-traumatic osteonecrosis may result from certain medications, such as corticosteroid medications (e.g., prednisone, cortisone, dexamethasone, or methylprednisolone), particularly when a high dose of the medication is administered for a prolonged period of time; from excessive alcohol consumption; from radiation therapy; or as a result of a disease or condition. See, e.g., Xie et al., 2015, *Journal of Orthopaedic Translation*, 3:58-70, incorporated by reference herein.

In some embodiments, the present invention provides a method of treating osteonecrosis by administering to a subject in need thereof a therapeutically effective amount of a compound of Formula I, Formula Ia, Formula Ib, Formula II, or pharmaceutically acceptable salts thereof. In some embodiments, the present invention provides a method of treating post-traumatic osteonecrosis (e.g., osteonecrosis that occurs following a fracture or dislocation of a bone) by administering to a subject in need thereof a therapeutically effective amount of a compound of Formula I, Formula Ia, Formula Ib, Formula II, or pharmaceutically acceptable salts thereof. In some embodiments, the present invention provides a method of treating non-traumatic osteonecrosis by administering to a subject in need thereof a therapeutically effective amount of a compound of Formula I, Formula Ia, Formula Ib, Formula II, or pharmaceutically acceptable salts thereof. In some embodiments, the present invention provides a method of treating steroid-induced osteonecrosis (e.g., high dose steroid-induced osteonecrosis or glucocorticoid-induced osteonecrosis), alcohol-induced osteonecrosis, or smoking-induced osteonecrosis by administering to a subject in need thereof a therapeutically effective amount of a compound of Formula I, Formula Ia, Formula Ib, Formula II, or pharmaceutically acceptable salts thereof. In some embodiments, the present invention provides a method of increasing vascular density in an osteonecrotic tissue by administering to a subject in need thereof a therapeutically effective amount of a compound of Formula I, Formula Ia, Formula Ib, Formula II, or pharmaceutically acceptable salts thereof. In some embodiments, the present invention provides a method of preventing or reducing cell death in an osteonecrotic tissue by administering to a subject in need thereof a therapeutically effective amount of a compound of Formula I, Formula Ia, Formula Ib, Formula II, or pharmaceutically acceptable salts thereof.

In some other embodiments, the present invention provides a method of treating secondary-induced osteonecrosis by administering to a subject in need thereof a therapeutically effective amount of a compound of Formula I, Formula Ia, Formula Ib, Formula II, or pharmaceutically acceptable salts thereof. Examples of diseases or conditions which can induce osteonecrosis (i.e., secondary-induced osteonecrosis) include, without limitation, Legg-Calvé-Perthes disease, Caisson disease, sickle cell disease, post-irradiation, chemotherapy, arterial disease, Gaucher's disease, lipid disturbances, connective tissue disease, pancreatitis, kidney disease, liver disease, or lupus. In some embodiments, the osteonecrosis is idiopathic osteonecrosis.

The present invention also provides methods of treating patient populations characterized by injured bone, such as fractured bone or bone injured due to radiation, as well as children for whom osteoporosies medications are contraindicated.

In some embodiments, the present invention provides a method of promoting bone growth by administering to a subject in need thereof a therapeutically effective amount of a compound of the present invention. Bone growth can be measured in a variety of ways known to one of skill in the art. Methods of measuring bone growth include, but are not limited to, Uct (micro CT), Dual X-ray absorption (Bone density), ultrasound, QCT, SPA, DPA, DXR, SEXA, QUS, X-ray, using the human eye during surgically manipulation, Alizarin red S, serum osteocalcin, serum alkaline phosphatase, Serum bone Gla-protein (BGP), bone mineral content, serum calcium, serum phosphorus, tantalum markers, and serum IGF-1.

Many indicators of bone growth can be used to measure bone growth, including bone density. In some embodiments, bone growth can be demonstrated by an increase of 0.1% in bone density. In other embodiments, bone growth can be demonstrated by an increase of 0.2, 0.3, 0.4, 0.5, 0.6, 0.7, 0.8, 0.9, 1.0, 5, 10, 20, 30, 40, 50, 60, 70, 80, 90, 100, 200, 300, 400, 500, 600, 700, 800, 900 or 1000% or greater, in bone density. One of skill in the art appreciates that bone growth be local, systemic or both.

In some other embodiments, the method of the present invention promotes bone growth by administering the compound of the present invention, such as a compound of formula I. Administration of a compound of the present invention can promote local bone growth and/or systemic bone growth. In some embodiments, the administration of a compound of the present invention promotes systemic bone growth. Bone growth can be achieved by increasing bone mineral content, increasing bone density and/or growth of new bone. In other embodiments, local application of the compound of the present invention and a drug achieves systemic bone growth.

V. EXAMPLES

Example 1: Screening Cell Signaling Activators that have Affinity for Osterix+ Osteoprogenitor Cells The methods used to discover bone cell-targeted, osteogenic-specific peptides that possess both cell binding affinity and intracellular signaling involved on-bead screening of a focused one-bead one-compound (OBOC) peptide library, the design of which was based on integrin $\alpha_4\beta_1$ motifs. The synthetic approach used to develop the focused OBOC combinatory library is shown below in Scheme 1.

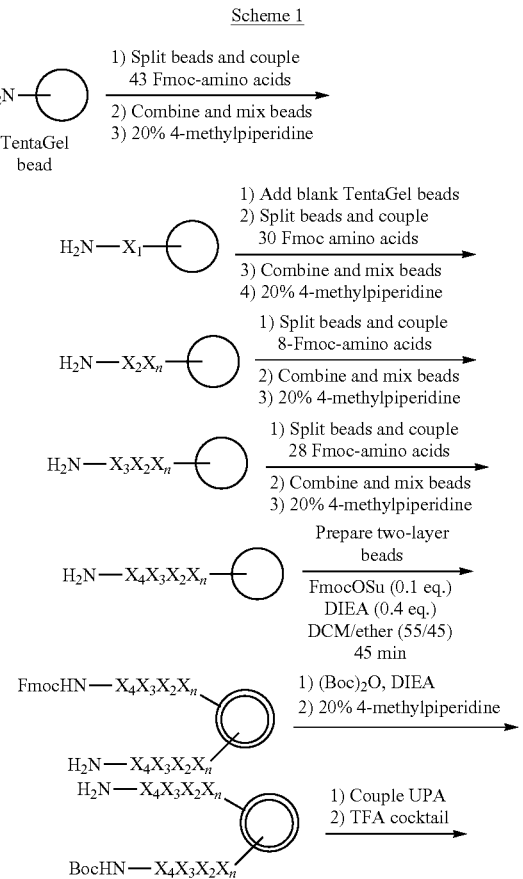

-continued

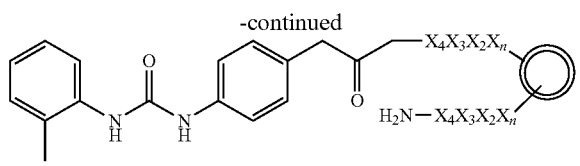

n = 0 or 1
Coding tag 90%
Focused OBOC library
Testing molecule 10%

In brief, TentaGel beads (1.0 g, loading 0.26 mmol/g) were swollen in DMF (20 mL) for 3 h. The resin was split into 43 equal portions in 43 disposable polypropylene columns with a polyethylene frit. Forty-three different Fmoc-amino acids (Table 4) (4 equiv.) were separately dissolved in a solution of 6-Cl HOBt (4 equiv.) and DIC (4 equiv.) in DMF and were added into 43 columns (each column received only one amino acid). The coupling was carried out at room temperature for 2 h. After filtration, the beads were combined, mixed and washed three times each with DMF, MeOH, and DMF again. The beads were subjected to Fmoc deprotection with 20% 4-methylpiperidine (5 min, 15 min). After washing with DMF, MeOH, and DMF, the beads were mixed with 1 g of blank TentaGel beads. The 2 g of combined beads were sequentially coupled with 30 Fmoc-amino acids (Table 5) at $X_2$ position, 8 Fmoc-amino acids (Table 6) at $X_3$ position and 18 Fmoc-amino acids (Table 7) at $X_4$ position using same split-mix synthesis as above, respectively. After Fmoc-deprotected, the beads were washed with DMF, MeOH, DCM, and thoroughly dried in vacuum.

TABLE 4

Amino acids for positions $X_1$.

1 Fmoc-Orn(Boc)-OH

2 Fmoc-HoSer(Trt)-OH

3 Fmoc-Acpc-OH

4 Fmoc-L-HoCit

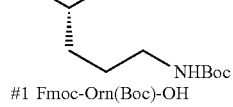
5 Fmoc-Hyp(tBu)-OH

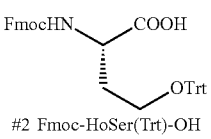

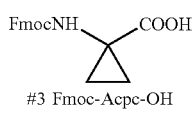

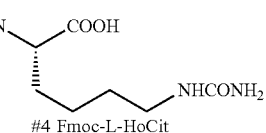

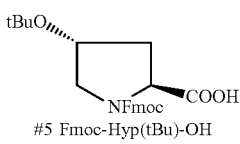

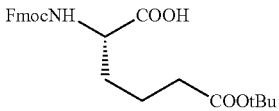

TABLE 4-continued

Amino acids for positions $X_1$.

6 Fmoc-Aad(OtBu)-OH

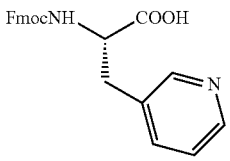
7 Fmoc-D-3-Pal-OH

8 Fmoc-L-Phg-OH

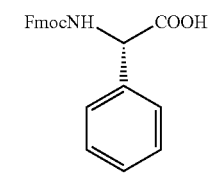
9 Fmoc-Nva-OH

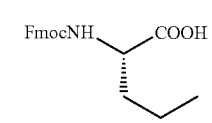
10 Fmoc-Dpr(Boc)-OH

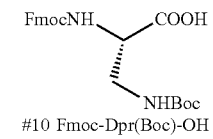
11 Fmoc-D-Tyr(Me)-OH

12 Fmoc-Aib-OH

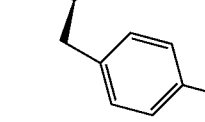
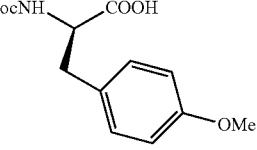
13 Fmoc-D-Chg-OH

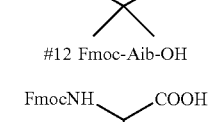
14 Fmoc-4-Apc(Boc)-OH

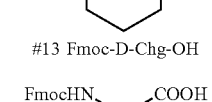
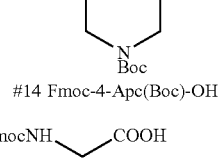
15 Fmoc-Phe(4-Me)-OH

TABLE 4-continued

Amino acids for positions $X_1$.

16 Fmoc-Nle-OH

17 Fmoc-D-Phe(3-Cl)-OH

18 Fmoc-D-HoPhe-OH

19 Fmoc-Aic-OH

20 Fmpc-Cha-OH

21 Fmoc-D-2-Nal-OH

22 Fmoc-L-1-Nal-OH

23 Fmoc-Phe(3,4-diCl)-OH

24 Fmoc-Bpa-OH

25 Fmoc-D-Ala-OH

26 Fmoc-D-Glu(OtBu)-

27 Fmoc-D-Asn(Trt)-OH

28 Fmoc-Gln(Trt)-OH

29 Fmoc-Ile-OH

30 Fmoc-D-Leu-OH

31 Fmoc-D-Lys(Boc)-OH

32 Fmoc-D-Ser(tBu)-OH

33 Fmoc-D-Met-OH

TABLE 4-continued
Amino acids for positions $X_1$.
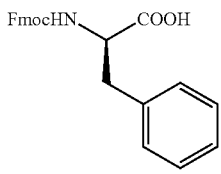
34 Fmoc-D-Phe-OH
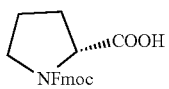
35 Fmoc-D-Pro-OH
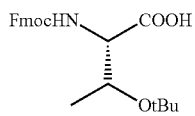
36 Fmoc-Thr(tBu)-OH
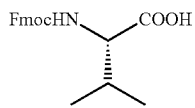
37 Fmoc-Val-OH
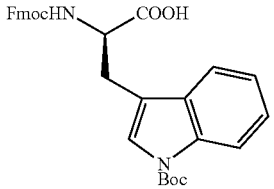
38 Fmoc-D-Trp(Boc)-OH
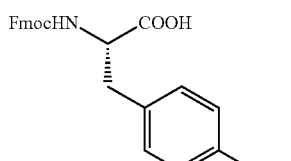
39 Fmoc-Tyr(tBu)-OH
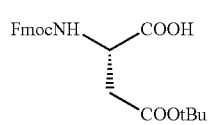
40 Fmoc-Asp(OtBu)-OH
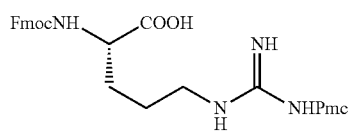
TABLE 4-continued
Amino acids for positions $X_1$.
41 Fmoc-Arg(Pmc)-OH
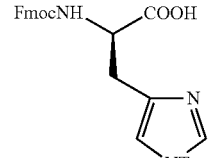
42 Fmoc-D-His(Trt)-OH
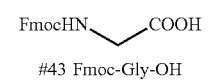
43 Fmoc-Gly-OH
TABLE 5
Amino acids for positions $X_2$.
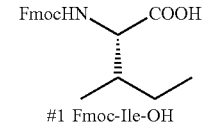
1 Fmoc-Ile-OH
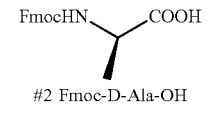
2 Fmoc-D-Ala-OH
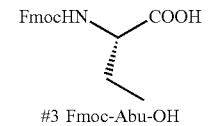
3 Fmoc-Abu-OH
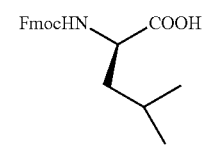
4 Fmoc-D-Leu-OH
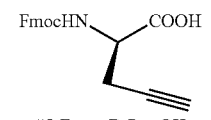
5 Fmoc-D-Pra-OH
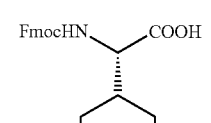
6 Fmoc-Chg-OH
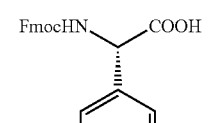
7 Fmoc-Phg-OH TABLE 5-continued Amino acids for positions $X_2$.

8 Fmoc-Nva-OH

9 Fmoc-Cha-OH

10 Fmoc-D-Tyr(tBu)-OH

11 Fmoc-Asp(OtBu)-OH

12 Fmoc-D-Val-OH

13 Fmoc-Acpc-OH

14 Fmoc-Glu(OtBu)-OH

15 Fmoc-Ser(tBu)-OH

16 Fmoc-Nle-OH

17 Fmoc-Bpa-OH

18 Fmoc-D-2-Nal-OH

19 Fmoc-D-Trp(Boc)-OH

20 Fmoc-Ana-OH

21 Fmoc-HoSer(tBu)-OH

22 Fmoc-Ach-OH

23 Fmoc-Aad(OtBu)-OH

24 Fmoc-D-Thi-OH

25 Fmoc-Phe(4-Me)-OH

TABLE 5-continued

Amino acids for positions $X_2$.

26 Fmoc-Aic-OH

27 Fmoc-D-Phe-OH

28 Fmoc-HoPhe-OH

29 Fmoc-D-Phe(3-Cl)-OH

30 Fmoc-D-Tyr(Me)-OH

TABLE 6

Amino acids for positions $X_3$.

11 Fmoc-Asp(OtBu)-OH

2 Fmoc-Glu(OtBu)-OH

3 Fmoc-Aad(OtBu)-OH

TABLE 6-continued

Amino acids for positions $X_3$.

4 Fmoc-Bmc(OtBu)-OH

5 Fmoc-Ile-OH

6 Fmoc-N-Me-Ile-OH

7 Fmoc-Leu-OH

8 Fmoc-Nle-OH

TABLE 7

Amino acids for positions $X_4$.

1 Fmoc-Ile-OH

2 Fmoc-Cha-OH

3 Fmoc-HoPhe-OH

4 Fmoc-Leu-OH

TABLE 7-continued

Amino acids for positions $X_4$.

5 Fmoc-Nle-OH

6 Fmoc-N-Me-Nle-OH

7 Fmoc-N-Me-Ile-OH

8 Fmoc-HoArg(Pbf)-OH

9 Fmoc-Gln(Trt)-OH

10 Fmoc-Aup-OH

11 Fmoc-Phe(4-CF$_3$)-OH

12 Fmoc-Cpa-OH

13 Fmoc-Orn(pyra)-OH

14 Fmoc-Phe(3,5-diF)-OH

15 Fmoc-HoCit-OH

16 Fmoc-Cit-OH

17 Fmoc-K(A38)-OH

18 Fmoc-K(A12)-OH

Two-layer beads were then prepared using bi-phasic solvent approach as described in ref (Liu R, Marik J, Lam K S. J Am Chem Soc. 2002 Jul. 3; 124(26):7678-80.). In brief, the dry beads were swollen in water for 1 day. Water was removed by filtration, and the solution of Fmoc-OSu (17.5 mg, 0.052 mmol, 0.1 equiv. to beads) in DCM/diethyl ether (150 mL, 55/45) was added to the wet beads, followed by addition of DIEA (36 µL, 0.208 mmol). The mixture was shaken vigorously at room temperature for 45 min. The liquid was removed by filtration. The beads were washed three times each with DMF, MeOH, and DCM again. A solution of Boc anhydride (567 mg, 2.6 mmol) and DIEA (906 µL, 5.2 mmol) in DCM was added to the beads and rotated for 1 h. The Kaiser test was negative indicating the coupling was complete. The Fmoc on the bead surface was removed with 20% 4-methylpiperidine (5 min, 15 min). The beads were washed and coupled with 4-[(N'-2-methylphenyl)ureido]-phenylacetic acid (UPA) (4 equiv.) in presence of 6-Cl HOBt (4 equiv.) and DIC (4 equiv.) in DMF. The coupling was complete in 4 h, confirmed by negative Kaiser test. After washing with DMF, methanol, and DCM, the beads were then dried under vacuum for 1 h. Side chain deprotection was achieved using a mixture of 82.5% TFA: 5% phenol: 5% thioanisole: 5% water: 2.5% TIS. After neutralization with 2% DIEA/DMF twice, the resin was washed sequentially with DMF, MeOH, DCM, DMF, DMF/water, water, and PBS. The bead library was stored in 70% ethanol.

Figure 2:
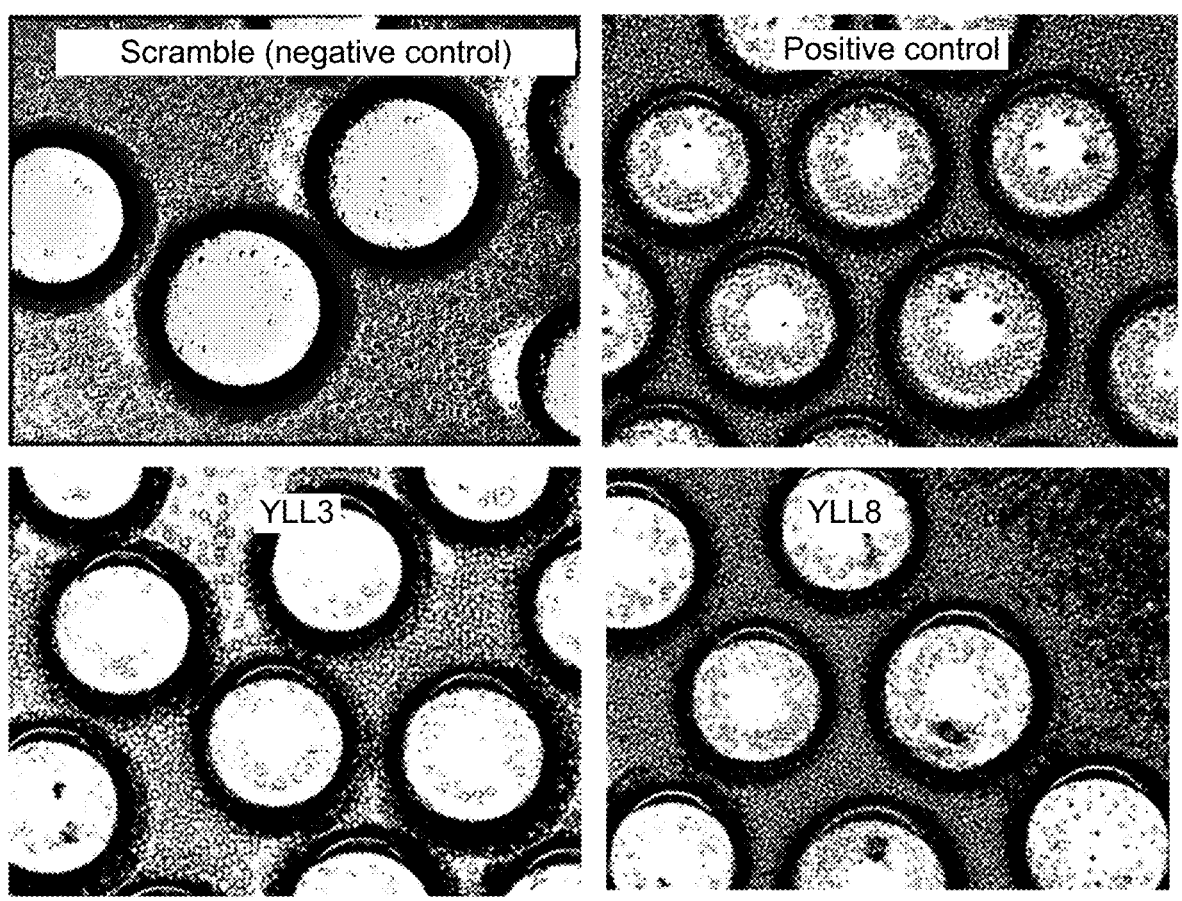
FIG. 2 shows lymphocyte bindings. Peripheral mononuclear cells were extracted from the blood and incubated with the beads displaying scramble, YLL3, or YLL8 peptides for 1 hour.

As shown in FIG. 1, the OBOC combinatorial library was screened and peptides that exhibited affinity towards the cell of interest and served as activators or inhibitors for the cell signaling pathway of interest (one bead/one-compound/two functions) were identified (See, Liu, R. et al, *Curr Opin Chem Biol.*, 2017, 38:117-26). Bone marrow stromal cells (BMSCs) were obtained from mice and maintained in mesenchymal maintenance medium for 7 days to two weeks (about 3 passages), switched to osteogenic medium for 3 days, and then incubated with the focused integrin library for 1 hour. The cells and beads were then fixed and stained for phosphorylated Akt, a signaling transduction pathway that promotes cell survival and growth in response to extracellular signals (See, Manning B D, et al. *Cell.* 2007, 129: 1261-74). The positive beads were identified as having cell binding and stained with green fluorescence (p-Akt+) (FIG. 1, step A). The positive beads were manually picked and subjected to microsequencing with Edman degradation (see, Liu and Lam, *Anal. Biochem.* 2001, 295:9-16). Individual peptides on beads were resynthesized with a fluorescence quencher (nitrotyrosine) residue inside the beads to quench autofluorescence of the beads. These beads were incubated with osteoprogenitor cells (OPCs) obtained from osterix-mCherry reporter mice. Osterix is expressed by osteochondral progenitors and is generally accepted as an early marker for osteoblast maturation, as described in Mizoguchi T, et al., *Developmental cell.* 2014, 29, 340-9 and Liu Y, et al., *PLoS One.* 2013, 8:e71318. The positive beads from the second round of screening were identified by their binding affinity toward osterix+ cells (FIG. 1 step B). Activation of Akt binding was reconfirmed (FIG. 1, step C). Using this method, 22 peptides (Table 8) were identified as Akt signaling activators having high affinity for osterix+ cells (FIG. 1, step D). Lead peptides YLL3 and YLL8 demonstrated high binding affinity to osterix cells and in vitro osteogenic effects. Beads displaying YLL3 and YLL8 also showed low affinity to lymphocytes (FIG. 2).

Example 2: Synthesis of YLL Ligands

YLL3, YLL8, and the other ligands set forth in Table 8 were prepared using commercially available starting materials and methods known in the art. In general, the YLL ligands were prepared via Fmoc solid phase peptide synthesis using 4-[(N'-2-methylphenyl)ureido]phenylacetic acid (UPA), Rink Amide MBHA resin, and the relevant component protecting amino acids, as described in International Publication Number WO 2012/031228 A2.

Solid Phase Synthesis of YLL3 and YLL8

YLL8 was synthesized on Rink amide MBHA resin (GL Biochem, Shanghai, China) using standard solid phase peptide synthesis method. In brief, Rink amide MBHA resin (0.5 g, 0.325 mmol, loading 0.65 mmol/g) was swollen in DMF for 2 h before Fmoc-deprotection with 20% 4-methylpiperidine in DMF twice (5 min, 15 min). The beads were washed with DMF (3×10 mL), MeOH (3×10 mL) and DMF (3×10 mL). Fmoc-Ach-OH (0.365 g, 0.975 mmol) was dissolved in a solution of 6-Cl HOBt (0.165 g, 0.975 mmol) and DIC (152 µL, 0.975 mmol) in DMF, and was then added into the beads. The coupling was carried out at room temperature for 2 h. After filtration, the beads were washed with DMF (3×10 mL), MeOH (3×10 mL), and DMF (3×10 mL), respectively, three times each. The Fmoc deprotection group was removed with 20% 4-methylpiperidine twice (5 min, 15 min). After washing with DMF, MeOH, and DMF respectively, the beads were then subjected to additional coupling and deprotection cycles stepwise with Fmoc-Aad (tBu) and Fmoc-Lys(A12) in the same manner as described above. After removal of Fmoc, a solution of 4-[(N'-2-methylphenyl)ureido]phenylacetic acid (UPA, 0.923 g, 3.25 mmol), HOBt (0.498 g, 3.25 mmol) and DIC (509 µL, 3.25 mmol) in DMF was added to the beads. The reaction was conducted at room temperature overnight. The beads were washed with DMF (5×5 mL), MeOH (3×5 mL) and DCM (3×5 mL). The beads were then dried in vacuo for 1 h before adding a cleavage mixture of 95% TFA: 2.5% water: 2.5% TIS. The cleavage reaction was conducted at room temperature for 2 h. The liquid was collected and concentrated. The crude product was precipitated with diethyl ether and purified using preparative RP-HPLC. The fraction was collected and lyophilized to give designed product YLL8, MALDI-TOF MS: 813.30 daltons.

YLL3 was synthesized using similar approach as YLL8, but coupled the following different building blocks Fmoc-Val-OH, Fmoc-Ser(tBu)-OH, Fmoc-Glu(OtBu)-OH, Fmoc-Cit-OH, and UPA sequentially to beads. The crude YLL3 was cleaved off the beads and purified by RP-HPLC. MALDI-TOF MS: 756.25 daltons.

TABLE 8

YLL Ligands.

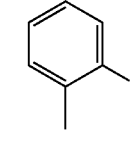

| Name | $X^4$ | $X^3$ | $X^2$ |
|---|---|---|---|
| YLL1 | N-Me Ile | Glu | Asp |

TABLE 8-continued

YLL Ligands.

| | | | |
|---|---|---|---|
| YLL2 | K$_{12}$ | Glu | Ile |
| YLL3 | Cit | Glu | Ser |
| YLL4 | K$_{12}$ | Glu | Glu |
| YLL5 | N-MeLeu | Asp | D-Pra |
| YLL6 | K$_{38}$ | Glu | Ile |
| YLL7 | K$_{38}$ | Glu | Glu |
| YLL8 | K$_{12}$ | Aad | Ach |
| YLL9 | Ile | Glu | Acpc |
| YLL10 | HoCit | Ile | Phe(4-Me) |

TABLE 8-continued

YLL Ligands.

| | | | |
|---|---|---|---|
| YLL11 | Leu | Ser | Cha |
| YLL12 | HoCit | Glu | Glu |
| YLL13 | Ile | Glu | Aad |
| YLL14 | HoPhe | Nle | Glu |
| YLL15 | K38 | Aad | Phe(4-Me) |
| YLL16 | K12 | Aad | Hyp |
| YLL17 | K38 | Aad | Aic |
| YLL18 | Ile | Aad | Ser |
| YLL19 | Ile | Aad | Ser |

TABLE 8-continued

YLL Ligands.

| | | | |
|---|---|---|---|
| YLL20 | HoCit | Aad | Gln |
| YLL21 | HoCit | Aad | D-Glu |
| YLL22 | HoCit | Aad | D-Chg |

| Name | X¹ (or X$^{1a}$)* | X$^{1b}$* |
|---|---|---|
| YLL1 | Pro | — |
| YLL2 | Aad | — |
| YLL3 | Val | — |
| YLL4 | Arg | — |
| YLL5 | 4-Apc | — |

TABLE 8-continued
| | YLL Ligands. | |
|---|---|---|
| YLL6 | 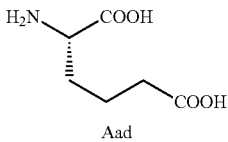 [SMILES: N[C@@H](CCCC(=O)O)C(=O)O] Aad | — |
| YLL7 | 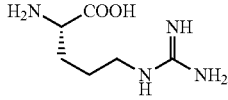 Arg | — |
| YLL8 | — | — |
| YLL9 | — | — |
| YLL10 | 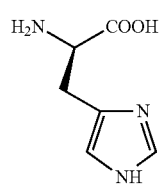 D-His | — |
| YLL11 | 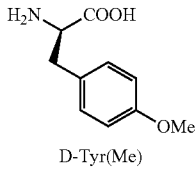 D-Tyr(Me) | — |
| YLL12 | 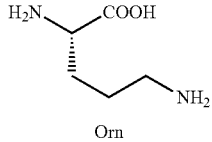 Orn | — |
| YLL13 | 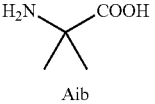 Aib | — |
| YLL14 | — | — |
| YLL15 | 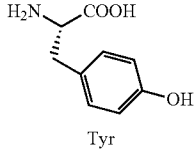 [SMILES: N[C@@H](Cc1ccc(O)cc1)C(=O)O] Tyr | — |
| YLL16 | 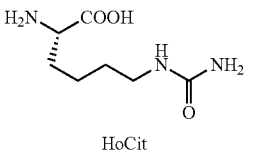 [SMILES: NC(=O)NCCCC[C@H](N)C(=O)O] HoCit | 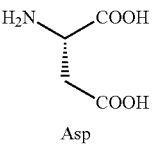 Asp |
| YLL17 | 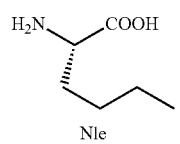 Nle | — |

TABLE 8-continued

YLL Ligands.

| | | |
|---|---|---|
| YLL18 | Asp | — |
| YLL19 | Tyr | — |
| YLL20 | Ile | Asp |
| YLL21 | D-Leu | Thr |
| YLL22 | Asp | D-Tyr(Me) |

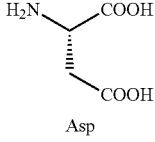

*when m = 1, —(X$^1$)$_m$— = X$^1$; when m = 2, —(X$^1$)$_m$— = —X$^{1a}$—X$^{1b}$—

Example 3: In Vitro Osteogenic Effects of the YLL Peptides

Figure 3:
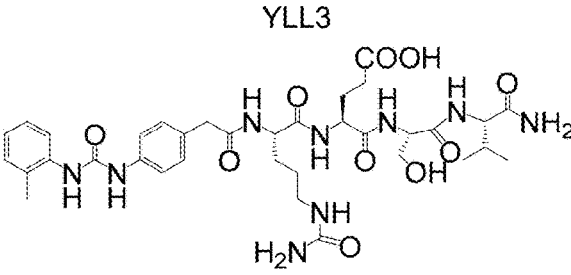
FIG. 3 is a comparison of YLL3, YLL8, and LLP2A peptides on affinity towards osteoprogenitor cells binding after a 10 day culture.
Figure 4:
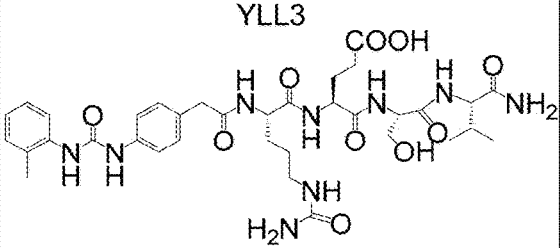
FIG. 4 is a comparison of YLL3, YLL8, and LLP2A peptides on activation of Akt signaling in osteoprogenitor cells after a 10 day culture.
Figure 5:
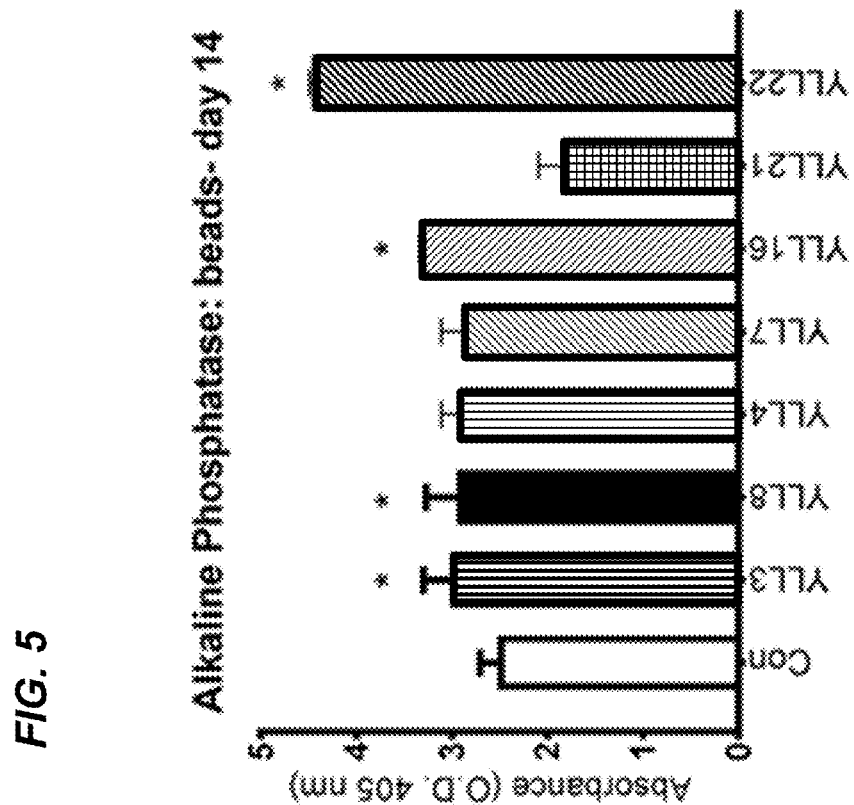
FIG. 5 is a comparison of several YLL peptides on osteogenesis in osteoprogenitor cells. Alkaline phosphatase levels were measured after 14 days. Osteoblast maturation and mineralization was measured after 21 days using alizarin red staining.
Figure 5:
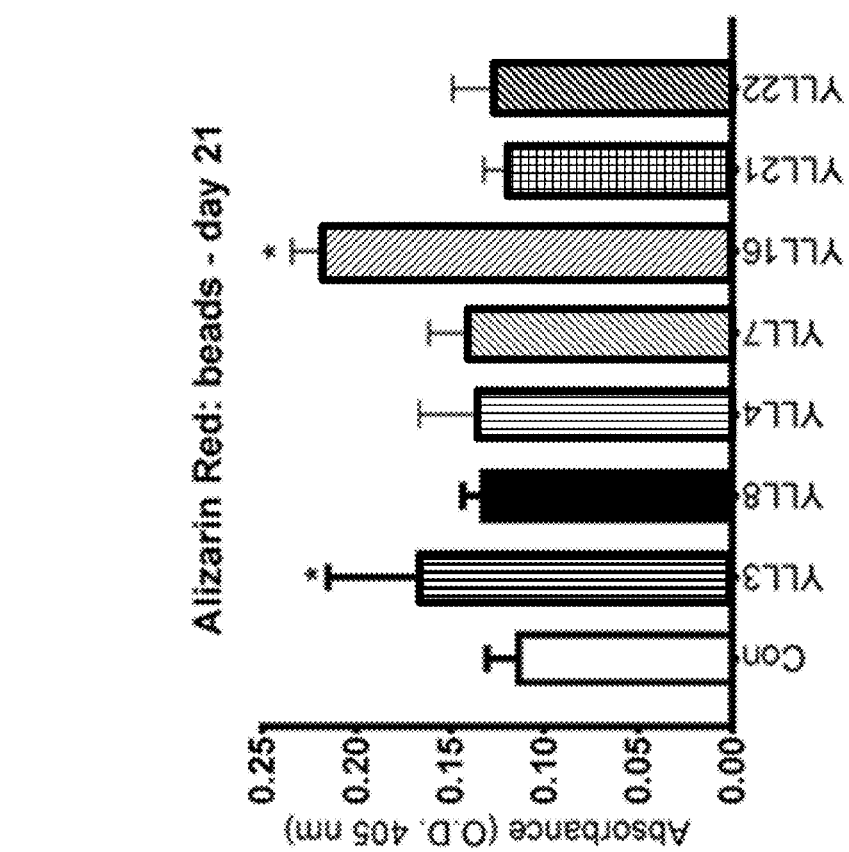

Lead peptides YLL3 and YLL8 had high binding affinity to osterix cells and demonstrated osteogenic effects in vitro, as shown in FIG. 3 and FIG. 4. Mouse bone marrow stromal cells (BMSCs) were obtained from osterix-mcherry transgenic mice and were cultured with the focus-library beads encoding YLL3, YLL8, and LLP2A peptides in osteogenic media for 10 days and fixed. Osterix (OSX+) labels osteochondrogenic progenitors and positive cells are in red. (FIG. 3). Mouse BMSCs were obtained from regular mice were incubated with focus-library beads displaying LLP2A, YLL3, or YLL8 peptides and cultured in osteogenic media for 10 days. The cells with beads were stained for anti-Akt-Alexa488. Positive cells demonstrated activation of Akt, which were stained in green (FIG. 4). Focus-library beads displaying several peptides of Table 4 were also incubated with mouse BMSCs obtained from regular mice and cultured in osteogenic media for 10 days. Alkaline phosphatase level, corresponding to osteogenic differentiation and osteoblast maturation, were measured at day 14. Alizarin red, a measure for osteoblast maturation and mineralization, was measured at day 21 (FIG. 5).

Figure 6A:
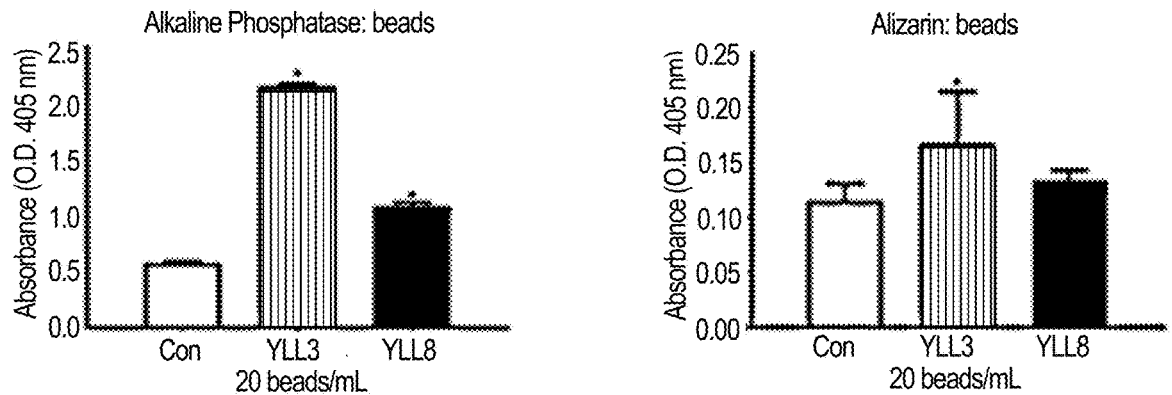
FIGS. 6A-6D show YLL3 and YLL8 stimulated osteogenesis in vitro. Bone marrow stromal cells were incubated with auto-fluorescence-quenched beads displaying YLL3 or YLL8 peptides in osteogenic media.
Figure 6B:
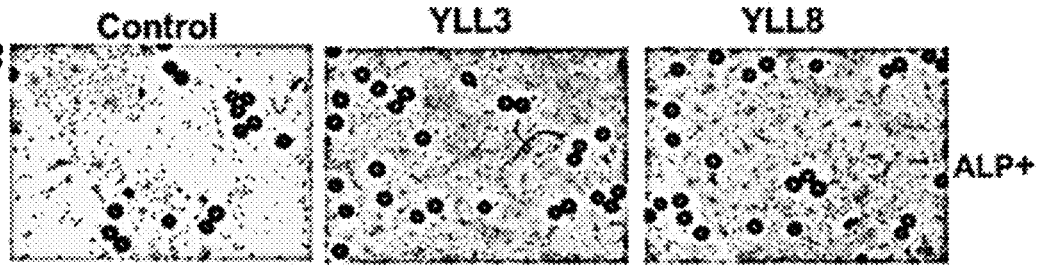
Figure 6C:
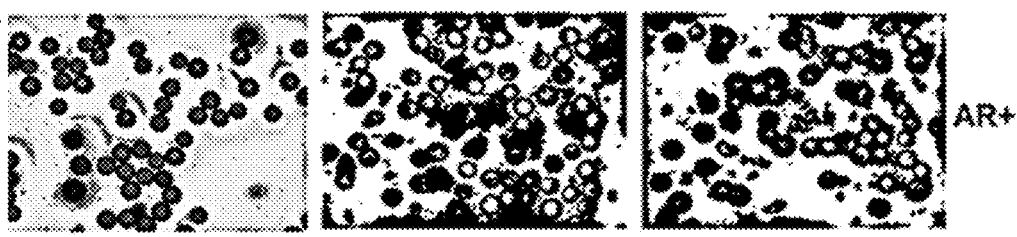
Figure 6D:
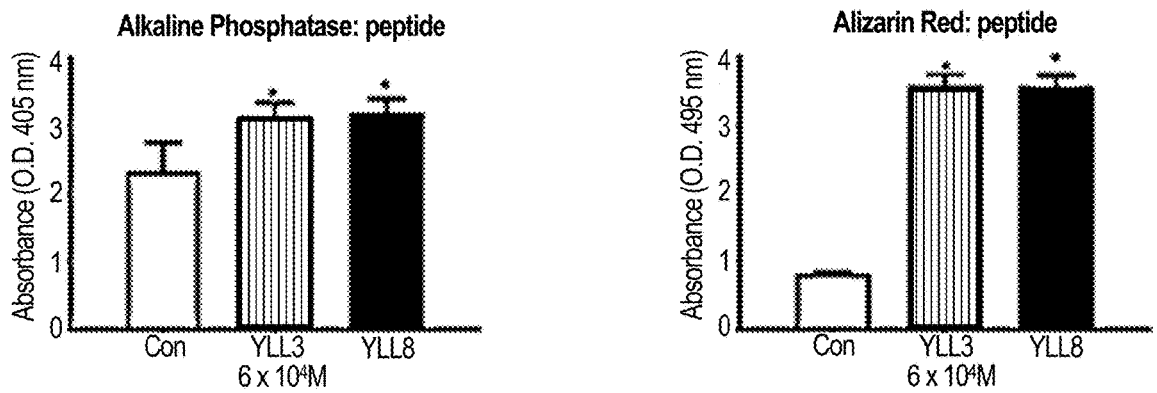

In an additional in vitro osteogenesis study, the osteogenic differentiation of YLL3 and YLL8 was measured (Alkaline phosphatase, ALP activity) at day 10 and osteoblast maturation (alizarin red staining) at day 21. Compared to beads displaying a scramble peptide (Con), beads displaying peptides YLL3 or YLL8 increased ALP levels (FIGS. 6A and 6B) and induced higher mineralization nodule formation (FIGS. 6A and 6C). Note that the cells were localized to or surrounded the beads and deposited minerals (FIG. 6C). These results were confirmed by directly adding the peptides to the osteoblast differentiation culture (FIG. 6D).

The specificity of Akt signaling activation by YLLs was then studied by western blot analysis using an Akt signaling array. Activation of the Akt pathway (FIG. 7A) was confirmed by first incubating the peptides (6×10$^{-8}$M) with BMSC in osteogenic medium for three days. Human PTH (1-34) (6×10$^{-8}$M) was used as a positive control. As shown in FIG. 7B, compared to the control and YLL3, YLL8 had a very similar profile with PTH in activating members in the Akt signaling pathway, including phosphorylation of Akt, Phosphoinositide-dependent kinase 1 (ERK1/2), P53, PDK1), p53, 4EBP1 and BCL2 Associated Agonist of Cell Death (BAD) and RIK1 (FIGS. 7B, 7C). YLL3 activated p53 and Akt (FIGS. 7B, 7C). These results suggested that the osteoblast-targeting peptide (e.g., YLL8) increased osteoblast differentiation and maturation through promoting signaling pathway ways for cell growth or pro-surviving mechanism.

Example 4: In Vivo Anabolic Effects of the YLL Peptides

Figure 8:
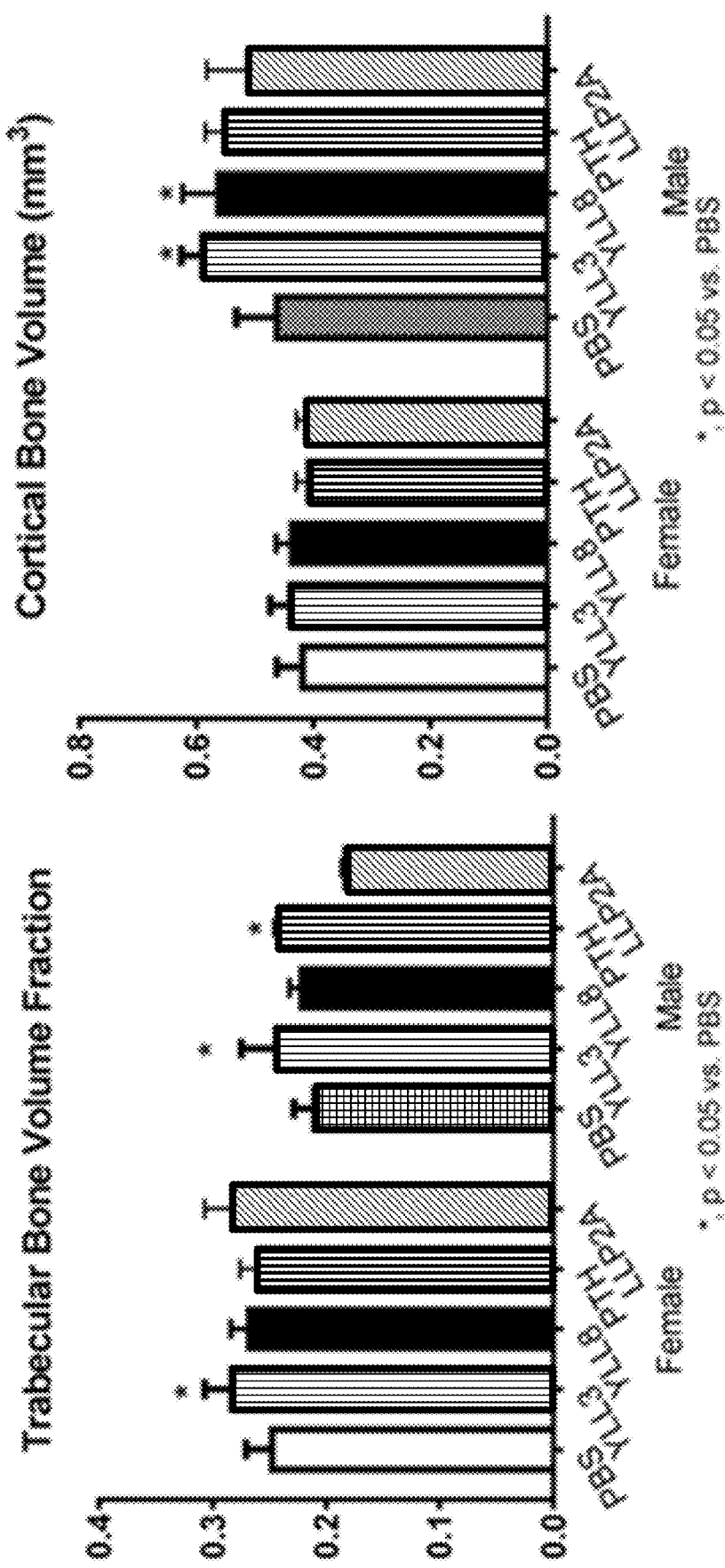
FIG. 8 is a comparison of treatments of YLL3, YLL8, and LLP2A peptides on bone mass in young mice.

In one study to determine whether the YLL peptide would effect bone metabolism in vivo, two-month-old female and male mice were treated with PBS control, YLL3, YLL8 or LLP2A at 50 µg/kg, IV at day 1. hPTH (1-34) was given at 25 µg/kg, sc., 5×/week for 21 days (n=4-6/group). Trabecular bone volume and cortical bone volume measured in the distal femur and cortical bone volume were measured at the distal femurs and the mid-femur by microCT (FIG. 8).

Figures 9A, 9B, 9C:
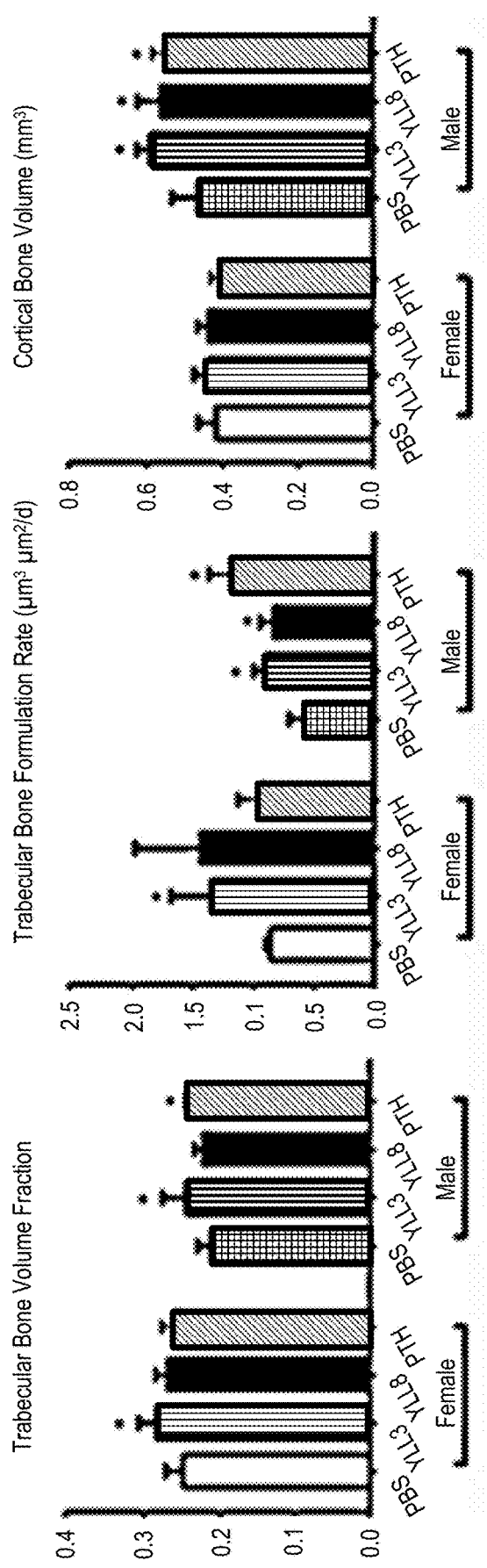
FIGS. 9A-9E show in vivo anabolic effects of YLL3 and YLL8 on bone mass in young mice. Two-month-old female and male mice were treated with PBS control, YLL3 or YLL8 at 50 µg/kg or PTH at 25 µg/kg, sc., 5×/week for 21 days (n=4-6/group). All mice received calcein at −7 and −2 days before euthanization. Trabecular bone volume and surface-based bone formation were measured in the distal femur and cortical bone volume and bone formation were measured in the mid-femur (FIGS. 9A, 9B, and 9C).
Figures 9D, 9E:
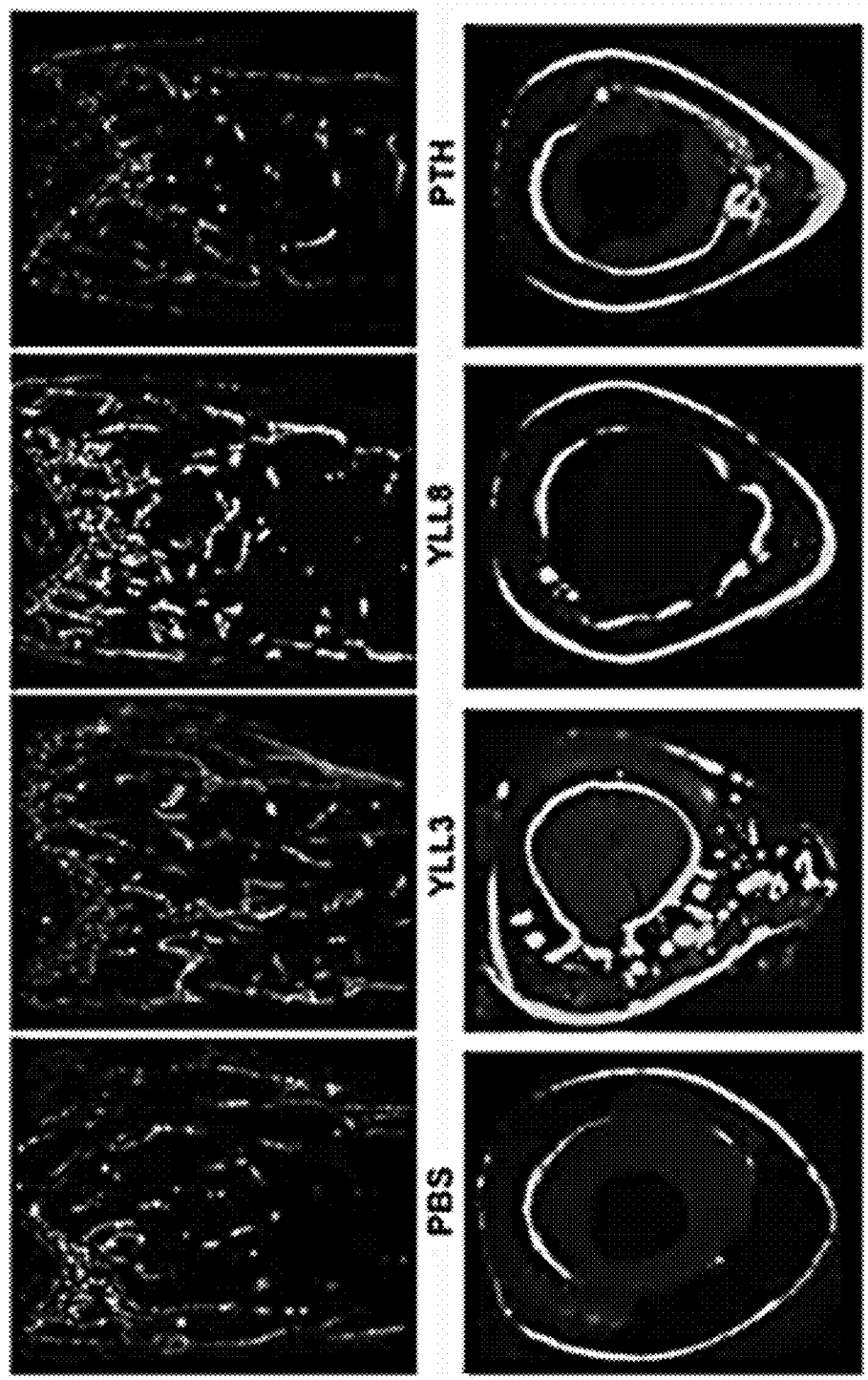

In an additional study to determine whether YLLs would affect bone metabolism in vivo, YLL3 and YLL8 were injected into 2-month-old mice at 25 or 50 µg/kg subcutaneously (SC), 5×/week, for 21 days. hPTH (1-34) was injected SC at 25 µg/kg, 5×/week as a positive control. Results from the 50 µg/kg groups are presented in FIG. 9. Daily injection of both YLL peptides for 21 days did not change body weights or caused any visible side-effects. In females, YLL3 and YLL8 increased trabecular bone volume by about 13% (p<0.05 vs. PBS) and 8% respectively (FIG. 9A), which were associated with 60% (p<0.05 vs. PBS) and 86% increases in surface-based trabecular bone formation rates (FIG. 9B and FIG. 9D). In males, YLL3 and YLL8 increased trabecular bone volume by about 15% (p<0.05 vs. PBS) and 6% respectively (FIG. 9A), which were associated with 53% (p<0.05 vs. PBS) and 50% (p<0.05 vs. PBS) increases in trabecular bone formation rates (FIG. 9A and FIG. 9D). Both YLL3 and YLL8 increased cortical bone volume by approximately 15% in males with higher bone formation being observed at the periosteal surface (FIG. 9C and FIG. 9E). Note that YLL3 increased intracortical bone remodeling (FIG. 9E). These results suggest that both YLL3 and YLL8 stimulated bone formation at both the trabecular and cortical surfaces and were comparable to the anabolic effects of daily PTH treatment.

Figures 10B, 10C:
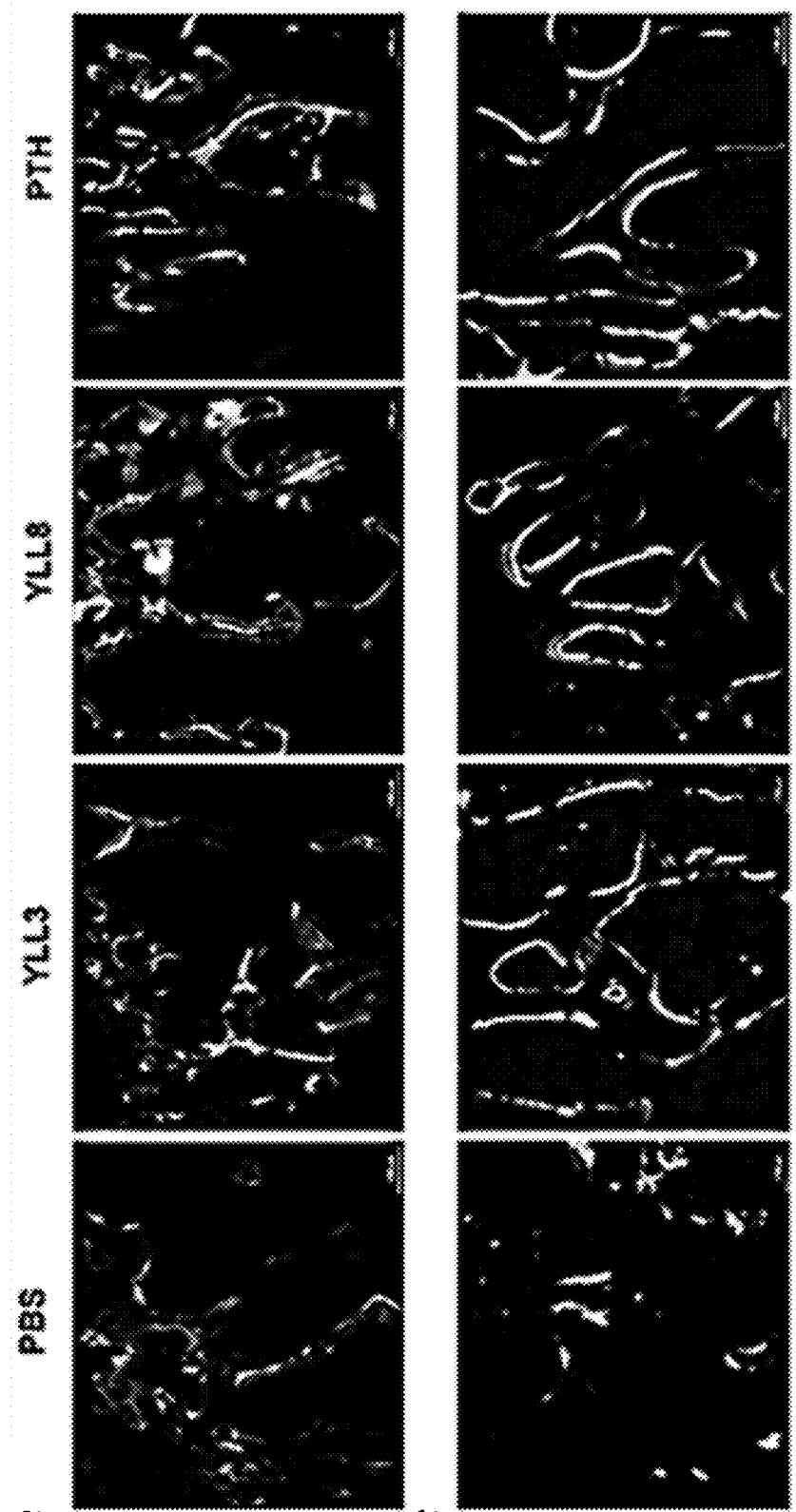
Figure 10D:
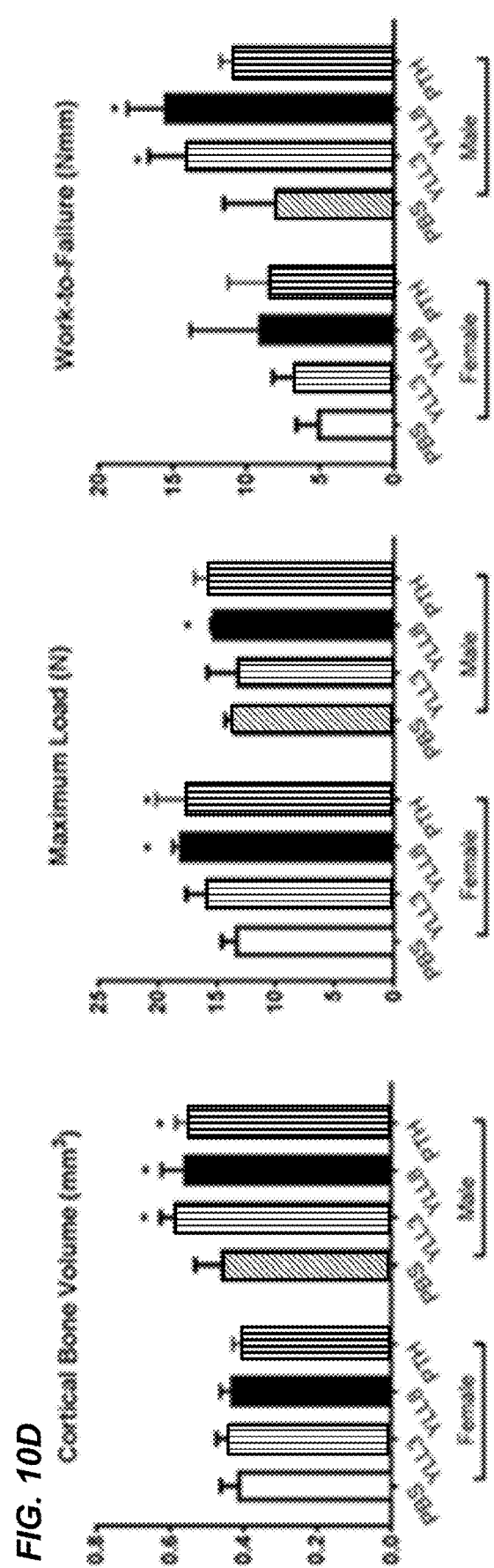
Figure 11:
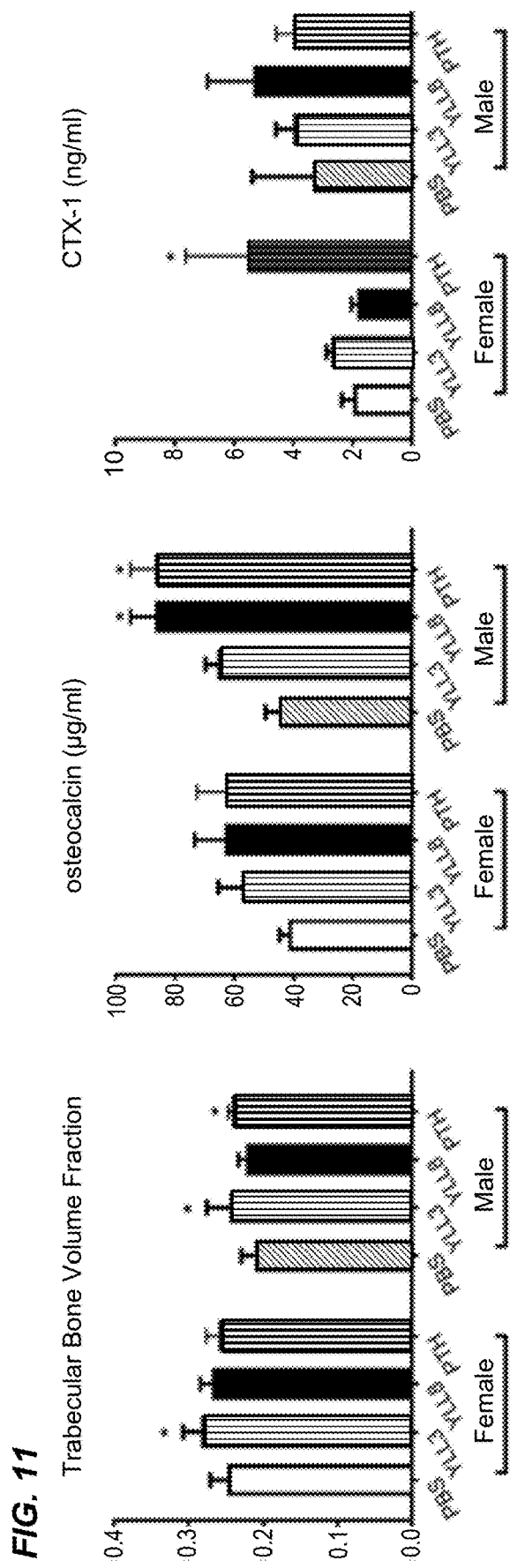
FIG. 11 shows the anabolic effect of YLLs on trabecular bone volume, osteocalcin, and CTX-1 in young mice. Four-month-old female and male mice were treated with PBS control, YLL3 at 5 µg/kg, YLL8 at 5 µg/kg, or PTH at 25 µg/kg, sc., 5×/week for 28 days (n=4-6/group). Trabecular bone volume was obtained by micro CT scans at the distal femoral metaphysis. Osteocalcin and CTX-1 were measured at the serum.

In another similar study to determine whether YLLs would affect bone metabolism in vivo, YLL3 and YLL8 were injected into 4-month-old female and male mice at 5 µg/kg subcutaneously (s.c.), 5×/week, for 21 days (n=5-7/group). hPTH (1-34) was injected s.c. at 25 µg/kg, 5×/week as a positive control. Daily injection of YLL8 for 21 days did not change body weights or cause any visible side-effects. Both YLL8 and hPTH (1-34) increased femoral trabecular bone volume by approximately 130% in the female mice, compared to the PBS-treated mice. In the male mice, YLL8 increase femoral trabecular bone volume by approximately 70%, and hPTH (1-34) increased femoral trabecular bone volume by approximately 30% (FIG. 10A). Mineral apposition rate, a parameter corresponding to osteoblast activity, was increased by more than 70% in the females and about 30% in the males, resulting in an overall increase in surface-based bone formation rate (FIGS. 10A, 10B). The anabolic effect of YLLs was confirmed by increased trabecular bone mass measured at the distal femur metaphysis by micro CT and serum level of osteocalcin (FIG. 11). Bone resorption measured by serum CTX1 suggested that PTH increased bone resorption by 200% from the PBS-treated group, especially in the female mice, while YLLLs did not change CTX1 significantly (FIG. 11). Daily YLL3 and YLL8 treatment for 21 days increased cortical bone mass in the males and increased bone strength in both females and males, which was comparable to daily hPTH (1-34) injections (FIG. 10D). These results suggested YLL3 and YLL8 induced uncoupling of bone formation and resorption and increased bone mass.

Figure 12:
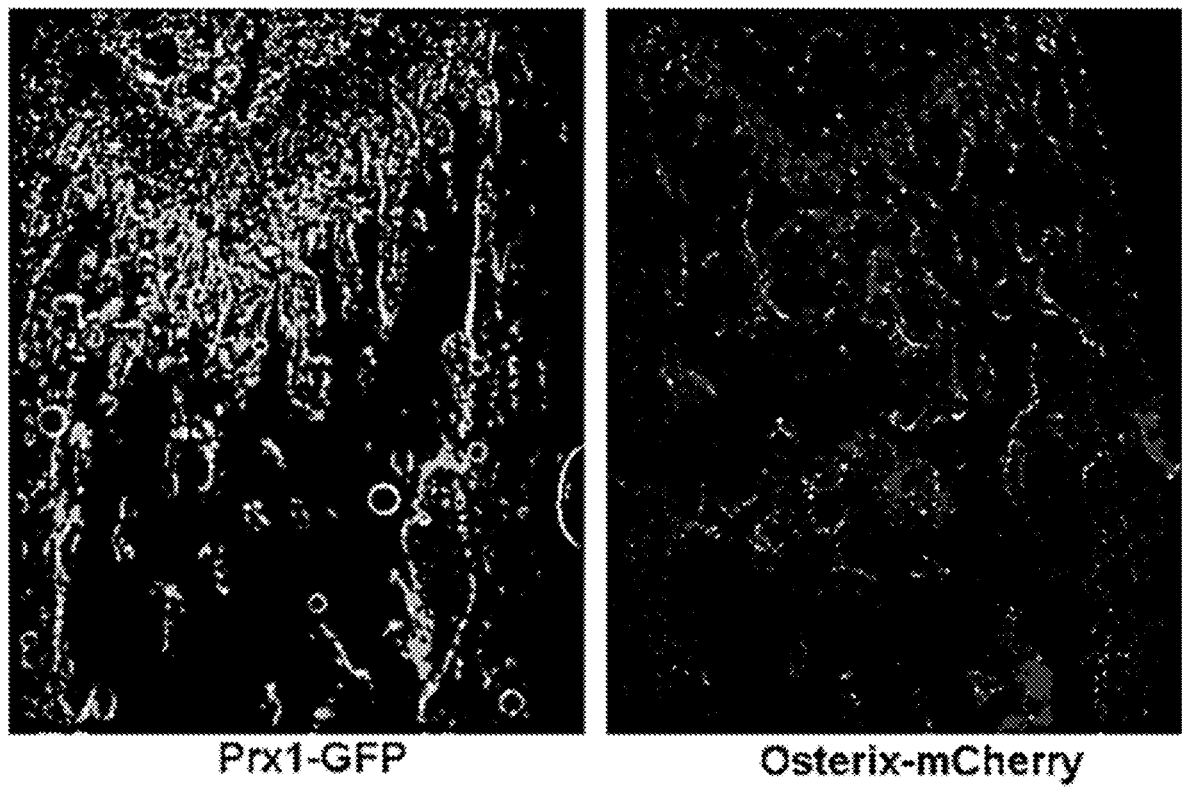
FIG. 12 shows expressions of Prx1 and osterix in bone. Representative distal femurs were shown for Prx1-GFP (green, left) and osterix-mCherry (red, right) mice
Figure 13C:
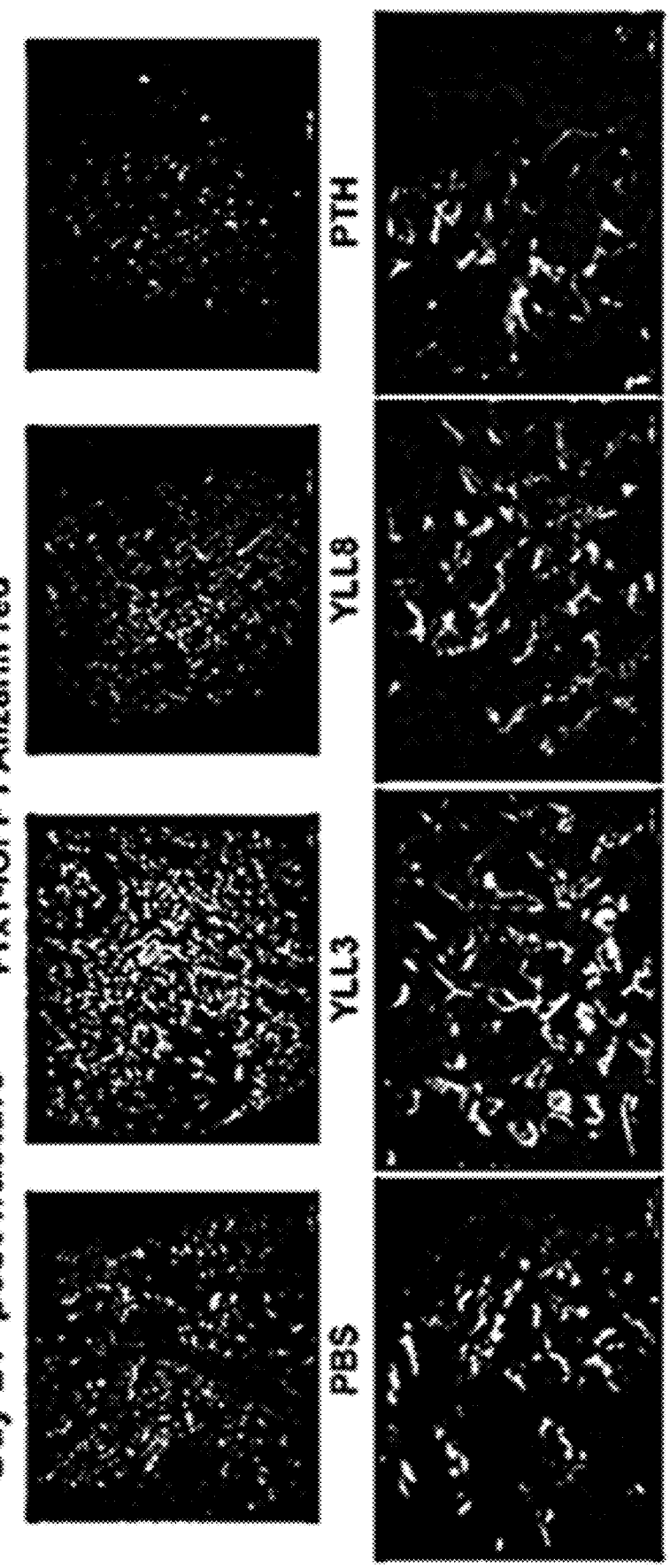
Figure 13D:
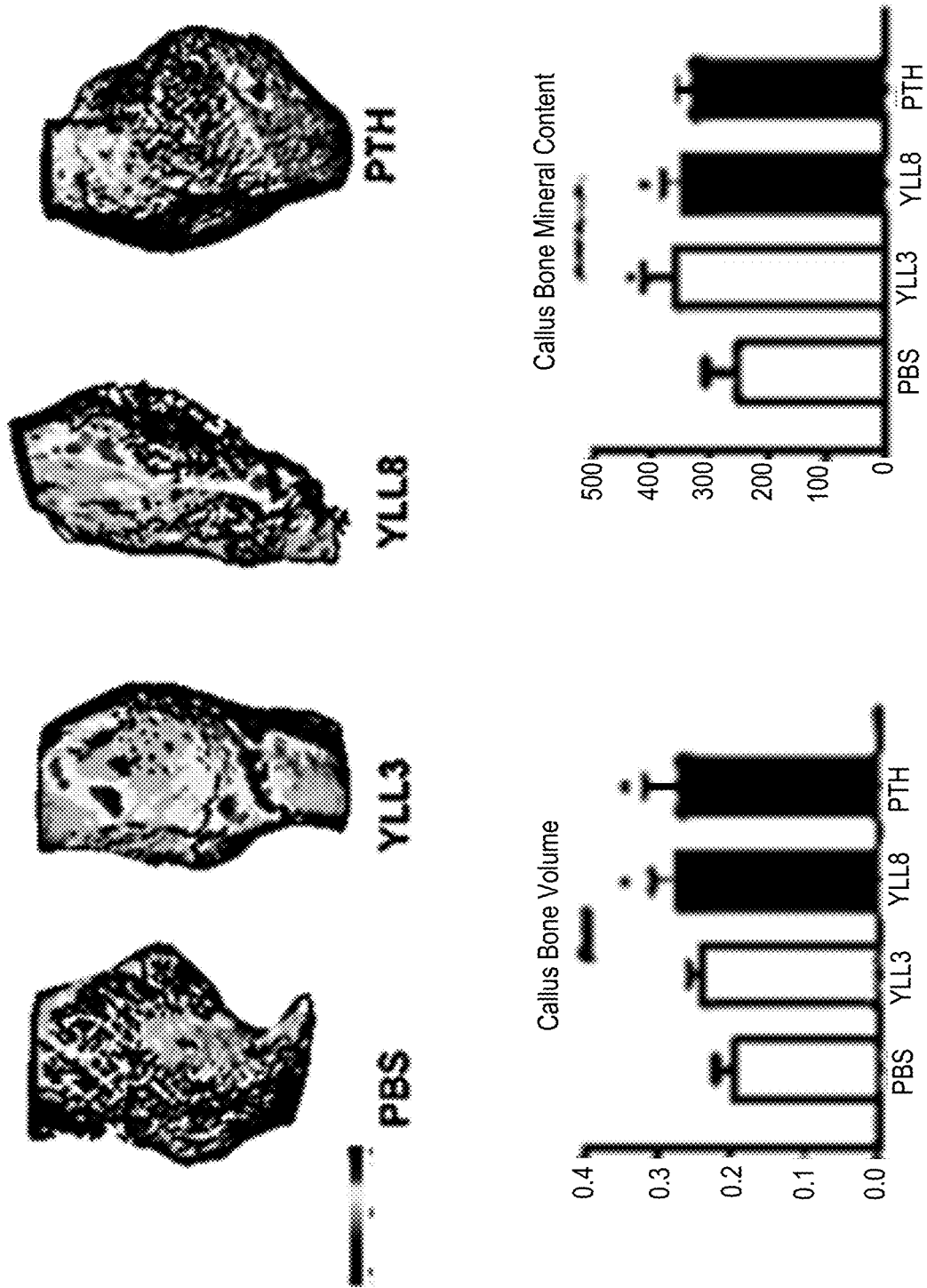

Example 5: Mineralization Potential During Fracture Repair Using YLL Peptides The following experiments were performed to determine whether the YLL peptides expedite fracture repair. The recruitment and activation of the endogenous osteoblast lineage cells during fracture healing is a crucial step to repair the fracture. Because the inducible osterix-reporting mouse is not directly commensally available, the inducible Prx1-CreERT-GFP mouse was used to track the recruitment and osteogenic differentiation of the osteoprogenitor cells following fracture and YLLs treatment. Prx1 marked the osteoprogenitor cells at the growth plate as well as alongside the trabeculae and endocortical bone surfaces in the un-injured mice, similar to where the osterix was expressed in bone (FIG. 12). A closed, stabilized middle-femur fracture model was used to track the movement of the osteoblastic lineage cells contribution to intramembrane or endochondral bone formation in this model. Human PTH (1-34) was used as a positive control (50 µg/kg, 5×/week). At day 10 following fracture, the presence of Prx1/GFP-expressing cells was observed within the callus, some co-localized with alizarin red, which suggested active bone apposition from those adjacent cells (FIG. 13A). The numbers of Prx1+ cells were greatly expanded in YLL8 and PTH-treated mice, some were co-localized with mineral apposition (FIG. 13A). Almost all the Prx1+ green cells were overlapping with alizarin red, suggesting high osteoblast differentiation and mineral uptake in these cells following YLL3 treatment (FIG. 13A), resulting in 100% higher callus bone volume compared to the PBS-treated mice at day 10 (FIG. 13B). Further dynamic histomorphometry studies using fluorochrome labeling for mineralization at day 21-post-fracture indicated that almost all the Prx1+ and their descendant cell were overlapping with AR mineral apposition in all the groups. Prx1+ and their descendant cells were activated in YLL3-treated mice and contributed to the callus formation, co-localized within the regenerated bone-callus regions (FIG. 13C). Quantitative measurements by micro CT scans confirmed higher callus mineral content in YLL3-treated mice by day 21 post-fracture (FIG. 13D). These data suggested that similar anabolic mechanisms activate the osteoblastic lineage cells by YLL8 and PTH during fracture healing. YLL3 injections greatly activated the osteogenic differentiation of the osteoprogenitor cells and induced significantly higher callus mineralization that expedited the fracture repair.

Example 6: Synthesis of YLL3-Alendronate (YLL3-Ale) & YLL8-Alendronate (YLL8-Ale)

To ensure that the anabolic effects were bone-specific, the YLL3 and YLL8 peptides were conjugated to alendronate.

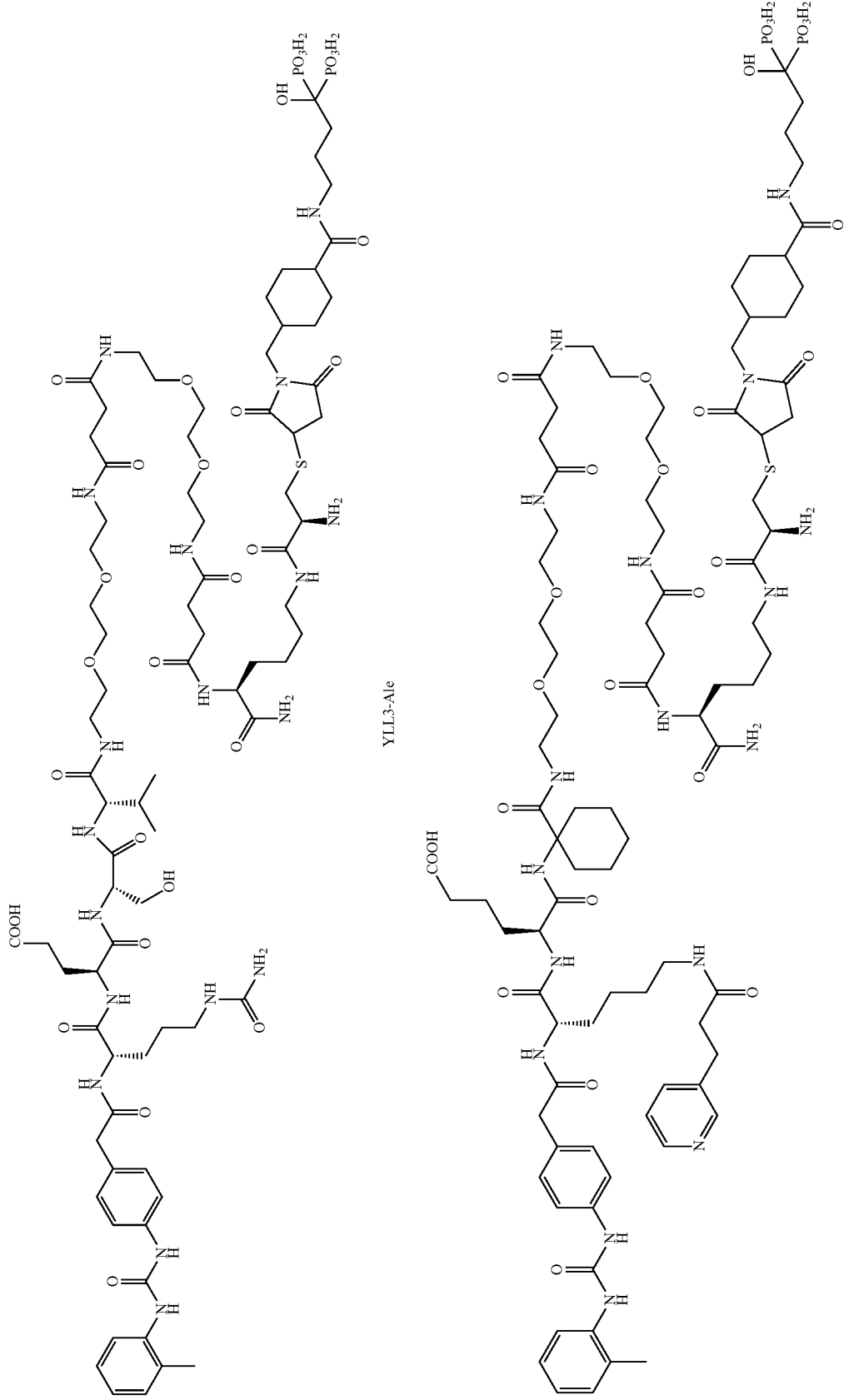

Figure 14:
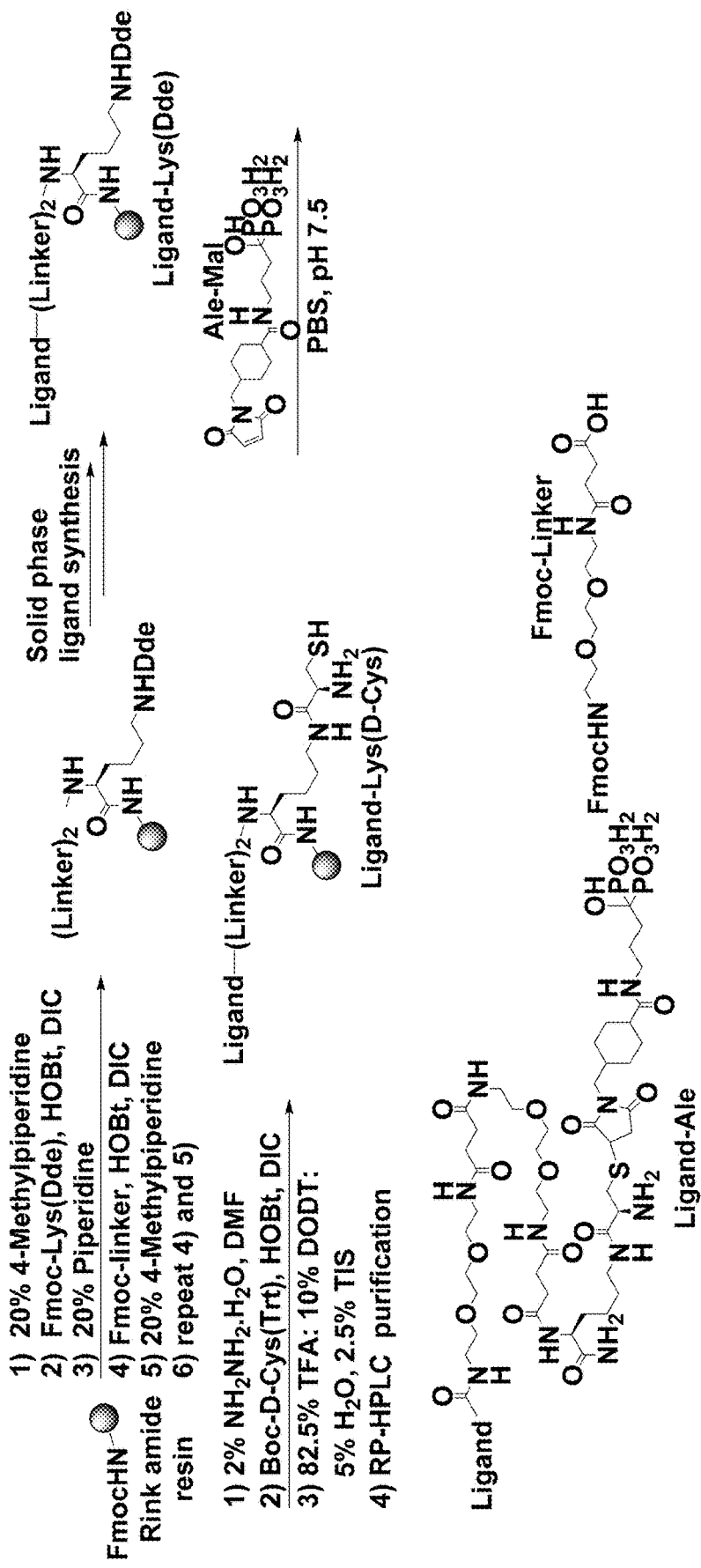
FIG. 14 shows the synthetic scheme of YLL3-Ale and YLL8-Ale conjugates.
Figure 14:
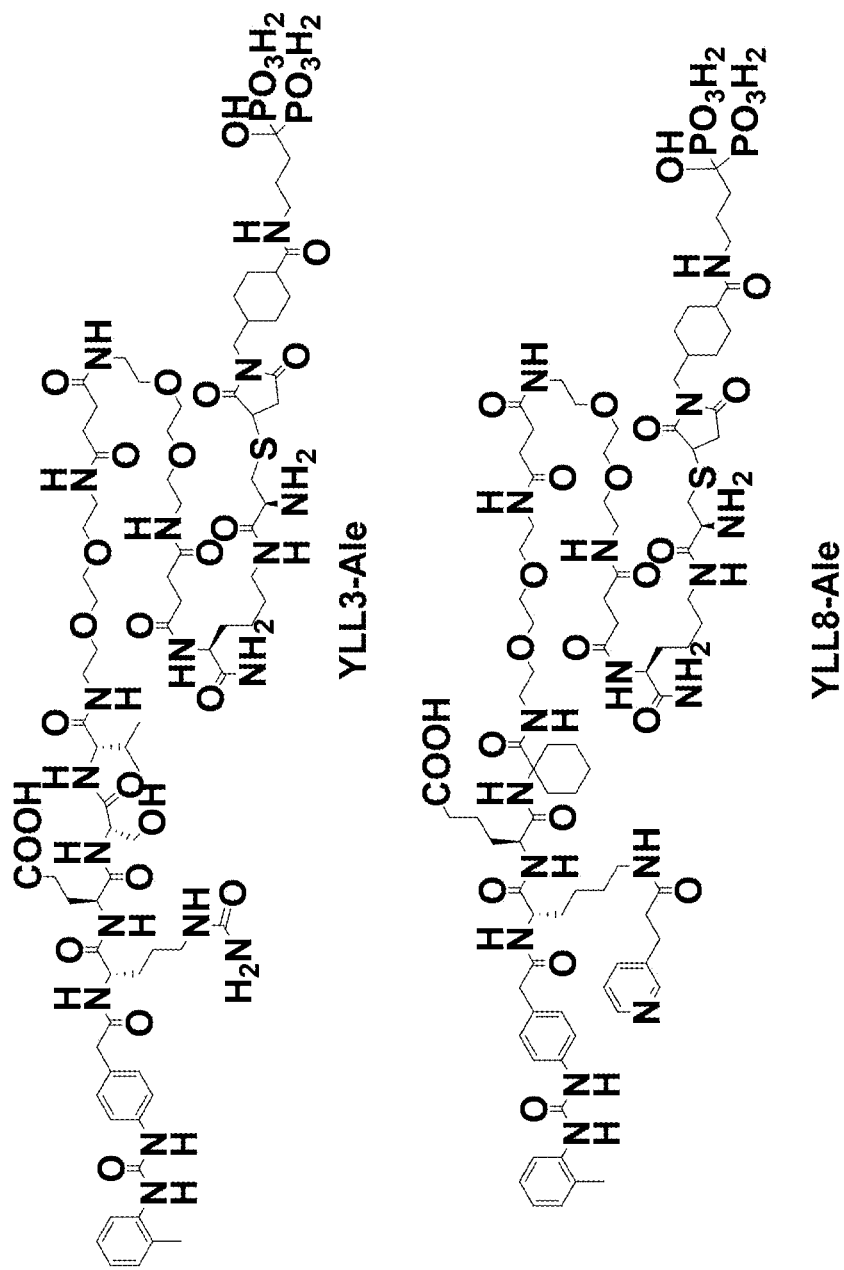

YLL3-Alendronate (YLL3-Ale) and YLL8-Alendronate (YLL8-Ale) were made by linking alendronate-maleimide (Ale-Mal) (produced via conjugation of alendronate and sulfosuccinimidyl-4-(N-maleimidomethyl)cyclohexane-1-carboxylate (sulfo-SMCC)) with D-cysteine, lysine, two N-(8-amino-3,6-dioxa-octyl)succinamide linkers, and YLL3 or YLL8 as shown in FIG. 14, and further described in International Publication Number WO 2012/031228 A2, or as described below.

In general, the synthesis of YLL8-Aln involves in three steps.

Step 1. Solid Phase Synthesis of YLL8-Lys(D-Cys)

The synthetic approach used to synthesize YLL8-Lys(D-Cys) is shown below in Scheme 2. Rink amide MBHA resin (0.5 g, 0.325 mmol, loading 0.65 mmol/g) was swollen in DMF for 3 hours. Fmoc was deprotected with 20% 4-methylpiperidine in DMF twice (5 and 15 minutes, respectively). After filtration, the beads were then washed with DMF (3×10 mL), methanol (MeOH) (3×10 mL) and DMF (3×10 mL), respectively. Fmoc-Lys(Dde)-OH (0.519 g, 0.975 mmol) was dissolved in a solution of 6-Cl HOBt (0.165 g, 0.975 mmol) and DIC (152 μL, 0.975 mmol) in DMF (8 mL), which was then added to the suspension of the beads. The coupling was carried out at room temperature overnight. After filtration, the beads were washed with DMF (3×10 mL), MeOH (3×10 mL), and DMF (3×10 mL), respectively. Fmoc was deprotected with 20% 4-methylpiperidine in DMF (8 mL) twice (5 and 15 minutes, respectively). Fmoc-Linker (0.612 g, 1.3 mmol) was dissolved in a solution of HOBt (0.22 g, 1.3 mmol) and DIC (201 μL, 1.3 mmol) in DMF (8 mL), which was then added to the suspension of the beads. The coupling was carried out at room temperature until Kaiser test is negative. After filtration, the beads were washed with DMF (3×10 mL), MeOH (3×10 mL), and DMF (3×10 mL), respectively. Fmoc was deprotected with 20% 4-methylpiperidine in DMF (8 mL) twice (5 and 15 minutes, respectively). Fmoc-Linker (0.612 g, 1.3 mmol) was dissolved in a solution of HOBt (0.22 g, 1.3 mmol) and DIC (201 μL, 1.3 mmol) in DMF (8 mL), which was then added to the suspension of the beads. The coupling was carried out at room temperature until Kaiser test is negative. After filtration, the beads were washed with DMF (3×10 mL), MeOH (3×10 mL), and DMF (3×10 mL), respectively. Fmoc was deprotected with 20% 4-methylpiperidine in DMF (8 mL) twice (5 and 15 minutes, respectively). After filtration, the beads were washed with DMF (3×10 mL), MeOH (3×10 mL), and DMF (3×10 mL), respectively. Fmoc-Ach-OH (0.365 g, 0.975 mmol) was dissolved in a solution of 6-Cl HOBt (0.165 g, 0.975 mmol) and DIC (152 μL, 0.975 mmol) in DMF, and was then added to the beads. The coupling was carried out at room temperature for 2 hours.

Scheme 2

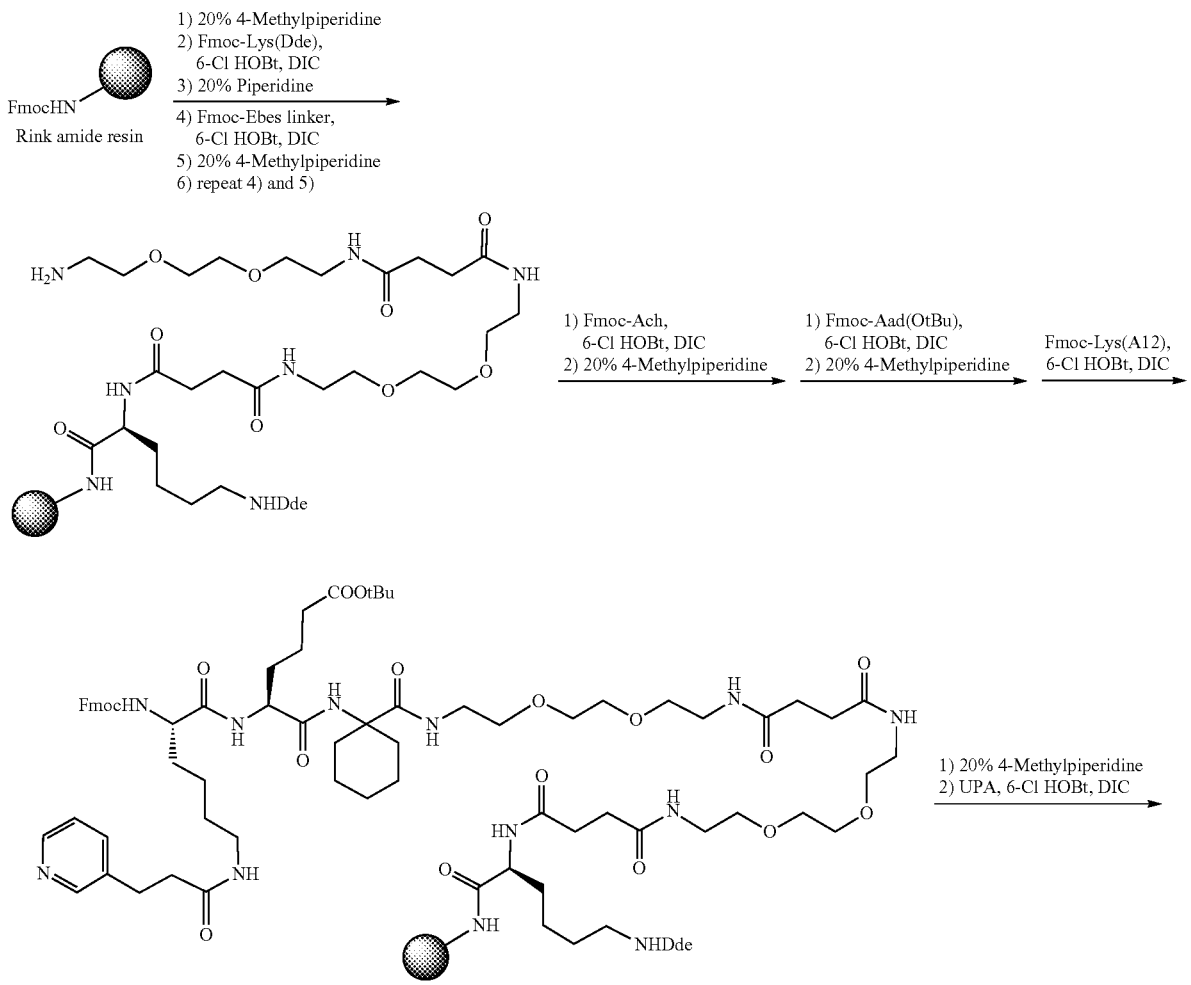

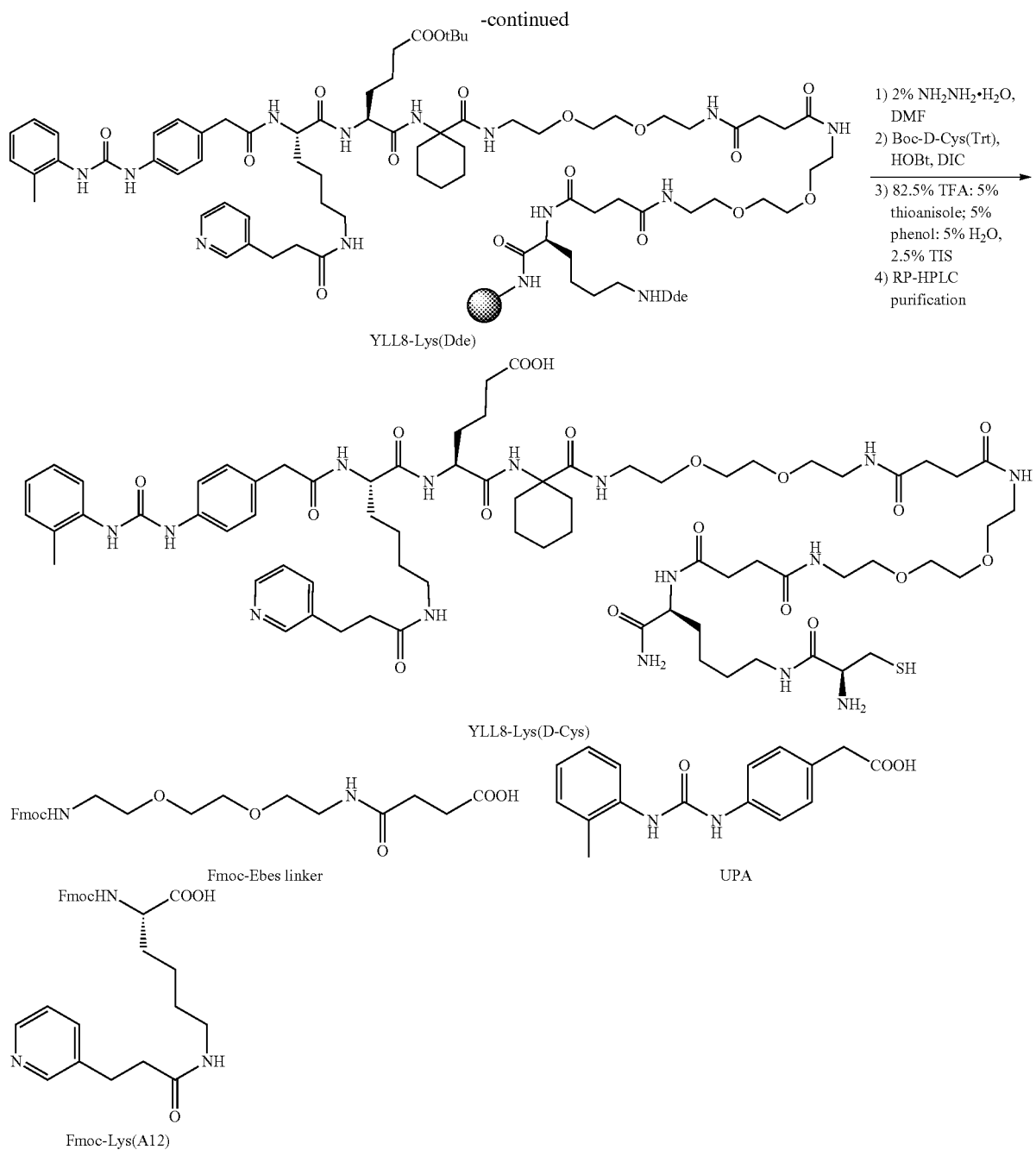

After filtration, the beads were washed with DMF (3×10 mL), MeOH (3×10 mL), and DMF (3×10 mL), respectively. The Fmoc deprotection group was removed with 20% 4-methylpiperidine twice (5 and 15 minutes, respectively). After washing with DMF, MeOH, and DMF respectively, the beads were then subjected to additional coupling and deprotection cycles stepwise with Fmoc-Aad(OtBu)-OH, Fmoc-Lys(A12) and UPA in the same manner as described above.

The Dde protecting group was removed with 2% hydrazine monohydrate in DMF twice (5 and 10 minutes, respectively) and the beads were again washed with DMF, MeOH and DMF, followed by coupling of Boc-D-Cys(Trt)-OH (4 eq. to resin, 220 mg, 1.3 mmol), HOBt (0.176 g, 1.3 mmol), and DIC (201 μL, 1.3 mmol) in DMF (8 mL). The coupling reaction was conducted at room temperature until Kaiser test negative (4 hours to overnight). The beads were thoroughly washed with DMF, MeOH and DCM, respectively, and then dried under vacuum for 1 hour before adding a cleavage mixture (8 mL) of 82.5% trifluoroacetic acid (TFA): 5% thioanisole: 5% phenol:5% water: 2.5% triisopropylsilane (TIS) (v/v). The cleavage reaction was conducted at room temperature over 2-3 hours. The off-white crude product was precipitated out and washed with cold diethyl ether. The purity was determined by analytical HPLC and the crude product was used in the next step without further purification.

Step 2. Synthesis of Aln-Mal

The synthetic approach used to synthesize Aln-Mal is shown below in Scheme 3. Alendronate disodium salt (35.4 mg, 0.1208 mmol) (powder from lyophilization of aqueous solution of alendronic acid and 2 eq. NaOH) was dissolved in 0.1 M PBS (15 mL) (with 10 mM EDTA), pH 7.5. The aqueous solution was then cooled in an ice water bath, and a solution of Sulfo-SMCC (58 mg, 0.133 mmol) in water (14 mL) was added dropwise. Following completion of addition, the resulting solution was allowed to warm to room temperature while being stirred for 2 hours to yield Aln-Mal solution which was used for next step conjugation without purification.

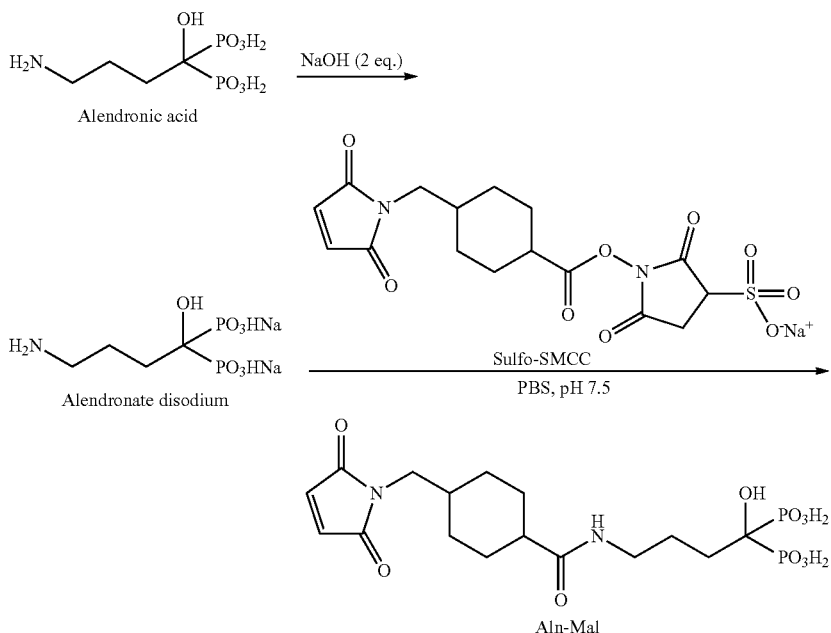

Scheme 3

Step 3. Conjugation of YLL8-Aln

The conjugation approach used to synthesize YLL8-Aln is shown below in Scheme 4. The Aln-Mal solution prepared in step 2 was cooled down with ice-water bath before the addition of acetonitrile (8 mL) and dropwise addition of a solution of LLP2A-Lys(D-Cys) (200 mg, 0.133 mmol) in a small amount (~4 mL) of 50% acetonitrile/water. The pH was adjusted to between 6 and 7 with aqueous $NaHCO_3$. The resulting mixture was stirred 1 hour and then allowed to warm to room temperature. Following a negative Ellman test, the solution was lyophilized. The resulting powder was redissolved in a small amount of 50% acetonitrile/water and purified by Reverse Phase High Performance Liquid Chromatography (RP-HPLC); Vydac C18 column (10 μm, 22×250 mm), Buffer A: 0.1% TFA/H2O, Buffer B: 0.1% TFA/acetonitrile. Gradient: 10% ACN, 1 min; 40% ACN, 50 min; 100% ACN, 3 min. The collected eluent was lyophilized to give an off-white powder YLL8-Aln, MALDI-TOF MS: 1972.75 Daltons. YLL3-Aln was synthesized by conjugation of YLL3-Lys(D-Cys) and Aln-Mal using similar approach as YLL8-Aln. MALDI-TOF MS: 1915.76 Daltons.

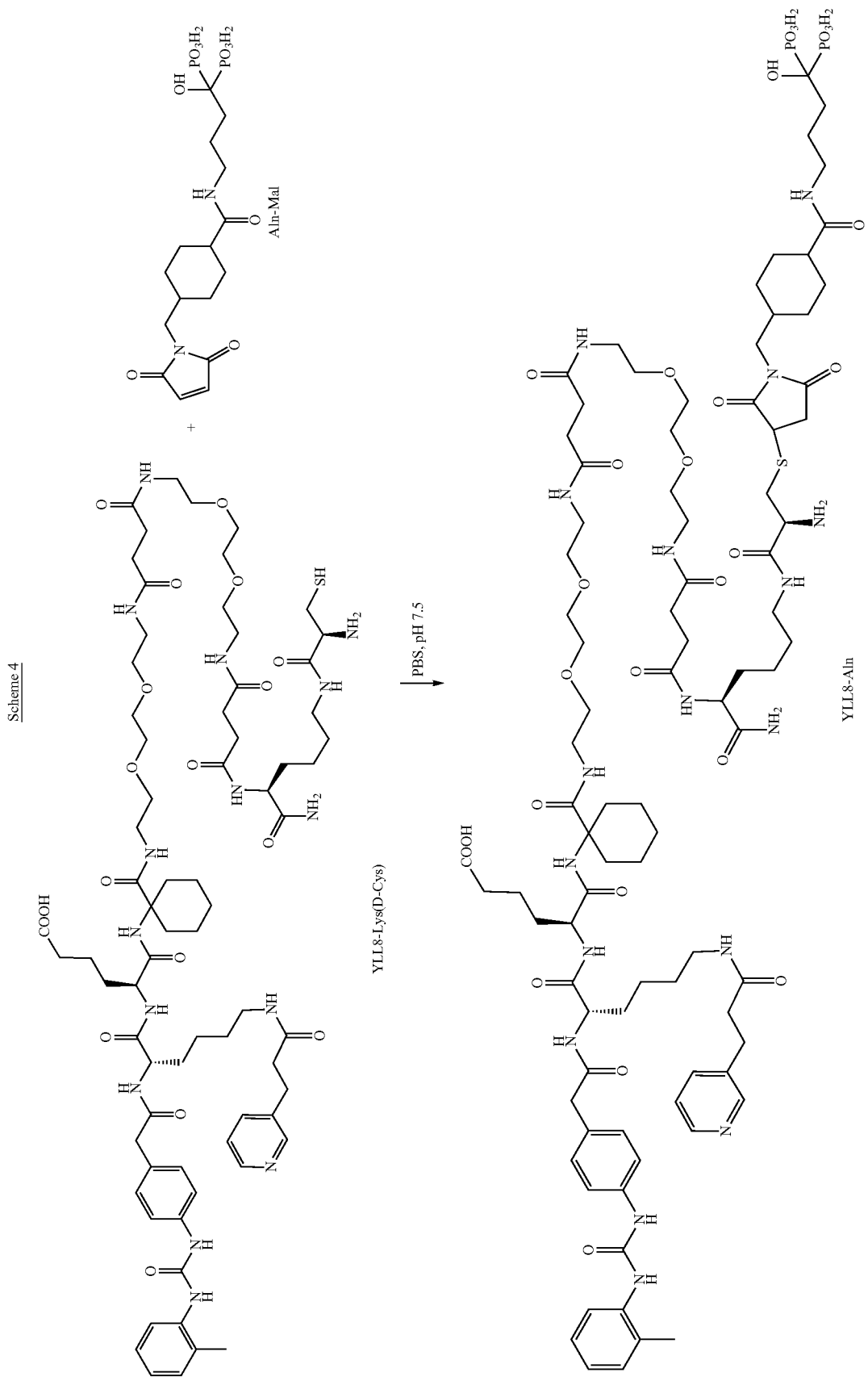

In some cases, the YLL-Ale compound is a single organic molecule consisting of a highly derivatized synthetic peptidomimetic section (the UPA-YLL section), having high affinity and specificity for the OPCs, is attached to the bone-targeting bisphosphonate alendronate via a hydrophilic link where the bisphosphonate section is coupled to the linker section via a Cu-free Click reaction of the DBCO with the $N_3$-modified alendronate (Aln-$N_3$), the latter being prepared from alendronate and 4-azidobutyric acid NHS ester ($N_3$—NHS).

Example 7: Alendronate Conjugated YLL8 Increased Bone Formation and Bone Mass

Figure 15C:
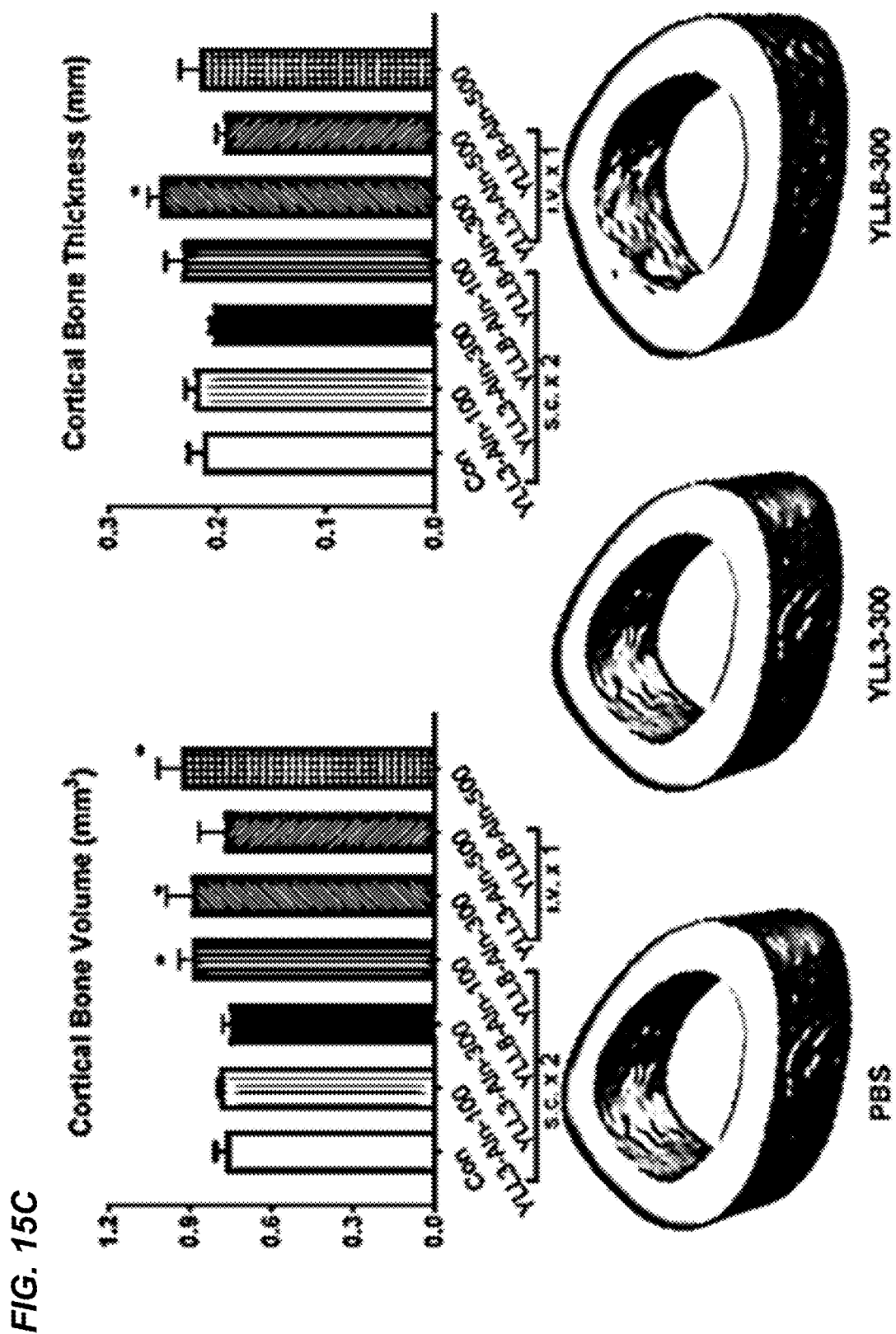
Figure 16:
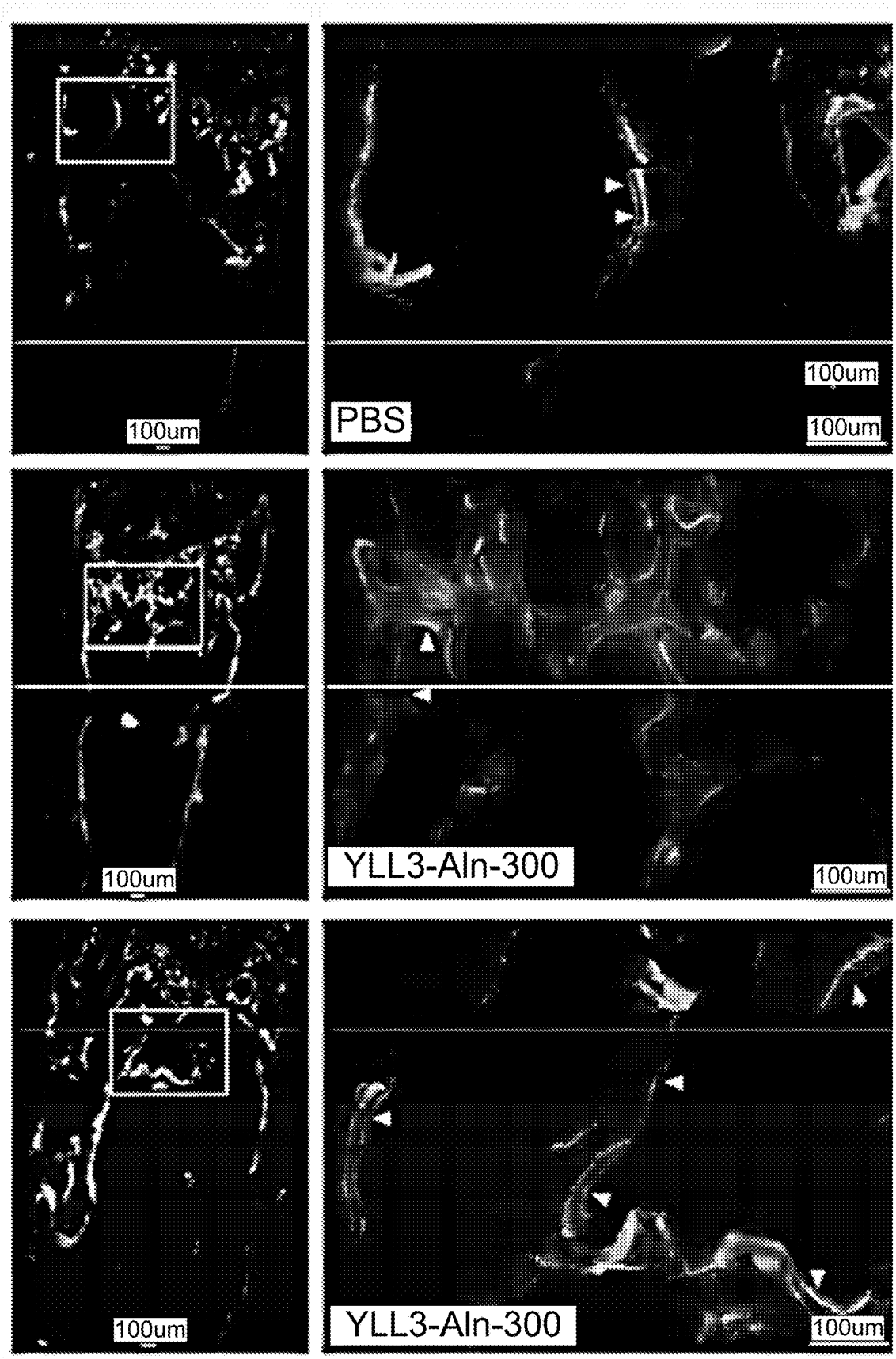
FIG. 16 shows two-month-old female mice treated with PBS control, YLL3-Aln or YLL8-Aln at 100 or 300 m/kg, respectively, sc., once every two weeks for 28 days (n=4-6/group). Trabecular bone formation was measured in the distal femoral metaphysis. *, $p<0.05$ vs PBS. Arrows show double labeled bone surfaces.

Next, the effects of alendronate-conjugated peptides on bone metabolism were evaluated. Two-month-old female mice were treated with PBS control, YLL3-Ale or YLL8-Ale at 100 μg/kg (25 nmol) or 300 μg/kg (75 nmol), subcutaneously, once every other week, or with one IV dose of 500 μg/kg. Two injections were given per mouse. The total cumulative doses were between 200 and 600 μg/kg/month (25-150 nmol), respectively. Alendronate concentration was approximately 1/10-1/5 of the compound. YLL-Ale injections did not change body weights or induced any visible side-effects. Although the peptide YLL3 alone showed an anabolic effect, YLL3-Ale at the two doses used failed to achieve statistically significant differences on bone formation or bone mass as compared to the PBS control (FIG. 15). In contrast, YLL8-Ale at the 300 μg/kg×2 SC doses or 500 μg/kg×1 IV dose increased trabecular bone volume by more than 20% ($p<0.05$ vs. PBS) which was associated with increased trabecular thickness (30%, $p<0.05$ vs. PBS) (FIG. 15A and FIG. 15B) and number (28%, $p<0.05$ vs. PBS). Both 100 μg/kg and 300 μg/kg doses of YLL8-Ale increased cortical bone volume by approximately 16% and cortical thickness by approximately 15% (FIG. 15C). YLL8-Aln increased bone formation rate by increasing osteoblast number and activity (higher double labeled surface and mineral apposition rate at both the trabecular and cortical bone surfaces, as shown in FIG. 16). These results suggest that bisphosphonate-conjugation of the YLL8 peptide decreases dosing frequency and sustains its anabolic effects. More specifically, these results show that 2 doses at total of 600 μg/kg/month of YLL8-Aln or one monthly dose of 500 μg/kg increase osteoblast activities, stimulate bone formation, and increase both trabecular and cortical bone mass.

As described herein, a dual affinity and functional screening method was used to discover "osteogenic-specific" peptides. Osteogenic peptide YLL8 had a high affinity for osterix+cells and activated phosphorylation of Akt, a pro-surviving signal for the osteogenic progenitors. Both YLL3 and YLL8 increased differentiation and maturation of the osteoblasts in vitro. Short term (3 week) daily injection of low dose YLL3 and YLL8 induced comparable bone anabolic action to PTH (1-34), increasing mineral apposition rate, corresponding to osteoblast activity, and bone formation rate. In contrast to PTH (1-34), daily injection of YLLs did not significantly affect bone resorption. This uncoupling of bone-remodeling resulted in rapid modeling-dependent bone gain and a rapid increase in bone strength in both trabecular and cortical bone, which was higher than hPTH (1-34)-treated mice. Daily injections of YLLs for 21 days, especially YLL3, greatly increased callus formation and mineralization during fracture repair. Conjugation of YLL8 to alendronate lowered injection frequency, but demonstrated a similar degree of bone gain in both trabecular and cortical bone. Compared to other bone anabolic drugs (e.g., large molecular-weight proteins), the YLL peptides are relatively small in size (e.g., three to four synthetic amino acids), which allows for easier manufacture and scale-up of YLL peptide-based drugs and/or pharmaceutical formulations, as well as easier metabolic breakdown thereof. YLLs can be used as a "therapeutic peptide," or deployed with a bone-affiliated agent to further its bone specificity.

Current pharmacologic treatment options for osteoporosis generally include antiresorptive treatment and anabolic treatment. For example, the recombinant human PTH (1-34) (Teriparatide) is known for its bone anabolic actions and consists of 34 amino acids, which is the bioactive portion of the hormone. Recently approved by the FDA for the treatment of osteoporosis, PTHrP (Abaloparatide) is a 139-173-amino acid protein with N-terminal homology to PTH. Both hPTH(1-34) and PTHrp have significant anabolic effects on bone, but also have other widespread physiological actions that are expressed in a diversity of tissues. Besides their effects on bone and joint development, PTH and PTHrp act in an autocrine/paracrine fashion to regulate calcein metabolism and organogenesis, such as mammary gland development. The sclerostin-antibody is another bone anabolic agent which may be more specific to bone cells. Sclerostin is primarily expressed in bone by osteocytes. However, sclerostin can also be expressed in the cartilage and in lymphocytes, which may lead to extra-skeletal side-effects. As such, the studies described herein were focused on the development of osteogenic anabolic drugs that can increase both trabecular and cortical bone mass.

The canonical Wnt/β-catenin signaling pathway plays a critical effect on bone formation and is an active drug target to use for studying/discovering bone anabolic therapeutic drugs. The studies described herein were focused on Akt activation because it was one of the lead kinases activated by $α_4β_1$ integrin upon binding to osteoprogenitor cells. Also, a focus was placed on activating the osteoprogenitor cells and their osteogenic potential rather than inducing cell mitogen or inducing de novo bone formation, which is typically observed when using Wnt-targeting or growth factors. To verify the effect of the osteogenic YLL peptides on osteoblast differentiation, ALP and AR staining was performed, which reflect the initial and terminal phases of osteoblast differentiation, respectively. The ALP and AR staining studies showed that YLL3 and YLL8 increased osteogenic differentiation of the osteoprogenitor cells in vitro. Activation of Akt signaling pathway was also confirmed. Similar to PTH, YLL8 showed broader effects on Akt pathway activation, while YLL3 was more specific for Akt activation. The studies described herein also demonstrated that injections of YLL3 and YLL8 resulted in increased mineral apposition rate, which is indicative of active osteoblast function. The YLL3 and YLL8 injections also resulted in increased bone formation, bone mass, and bone strength in young mice. The short-term treatment study (i.e., 21 days) showed that the YLLs generally had higher anabolic effects on the male mice than the female mice, which may have been due to young males having higher osteogenesis than the females and that high estrogen levels during growth may have negatively impacted bone formation in females.

The YLL peptides were conjugated to a bone targeting drug, alendronate. In this case, alendronate was used as a "carrier" for bone-specific delivery of the peptide. To further determine the enhancing bone-targeted effect of YLLs, in vivo experiments were performed and demonstrated that two s.c. doses or one i.v. dose of YLL8-Aln increased both trabecular and cortical bone mass. Collectively, these studies demonstrated that YLL8 could stimulate osteoblast differentiation in vitro and in vivo, demonstrating the efficacy of YLL8-Aln on bone formation. Dynamic bone histomorphometric and histologic analyses confirmed that YLL8 significantly promoted bone formation via enhancing the osteoblast activity. Surprisingly, YLL3-Aln lost its anabolic effects on bone when YLL3 was conjugated to alendronate. This may have been due to a conformational change of YLL3's structural configuration upon Aln conjugation. Increasing the dose and/or dosing frequency of YLL3-Aln may produce the anabolic effects observed for the unconjugated YLL3 peptide. Alternatively, the conjugation methods could be modified such that the YLL3 is cleaved from alendronate-conjugation and released after reaching the bone.

Apart from aging and osteoporosis, in the United States alone, nearly 8 million adults each year experience fractures, of which approximately 5-13% results in non-union or delayed union. Current therapies for the treatment of fracture non-unions consist mainly of bone grafts and the use of recombinant bone morphogenetic proteins (BMPs). Bone grafts have significant complication rates ranging from 10-25%, and are associated with inconsistent outcomes. BMP treatment requires orthopedic operation before BMP delivery. Furthermore, BMPs can cause inflammation, are poorly mineralized, and are costly. It is a continuous effort to develop bone-building anabolic agents that can increase bone mineralization and expedite fracture repair. To this end, daily injections of YLL3 led to mature callus development at an early stage (day 10 post-fracture) and greater callus mineral density at a later stage (day 21 post facture). Since the initial phase of fracture repair is the recruitment and activation of the osteoprogenitor cells, the results showing that the mice treated with YLL3 had massive mineral uptakes by the osteoprogenitor cells at the early stage suggests that activation of these endogenous osteogenic cells are being recruited to the fracture sites. The YLL3-treated mice formed well-mineralized lamellar tissue at day 21 compared to the more apparent woven bone formation in PBS-treated controls. Fracture became union at day 21 post-fracture, which was otherwise observed until after 35-45 days in mice, and was superior to daily injections of PTH used at 50 µg/kg. Whole bone strength measurements were not included in these fracture studies, but the increase in bone mineral density measured by micro CT was a main determinant for bone strength, suggesting that higher bone strength may result from higher bone mineral density following YLL3 treatment.

In conclusion, a screening method was used to identify osteoprogenitor cell specific targeting osteogenic peptides through a pro-cell surviving mechanism. The same "one-entity tri-action" screening principle can be used to screen antagonist or agonist drugs targeting other specific signaling. The two osteoprogenitor cell-targeting peptides, YLL3 and YLL8, increased osteoblast differentiation and maturation in vitro, and increased osteoblast activities in vivo. Improved bone specificity was also observed using peptide-bisphosphonate conjugates that sustain anabolic effects at lower drug dosing frequencies. The osteogenic peptides demonstrate bone-growing properties and may be used as therapeutic agents for treating osteoporosis and/or for expediting fracture repair.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A compound selected from the group consisting of:

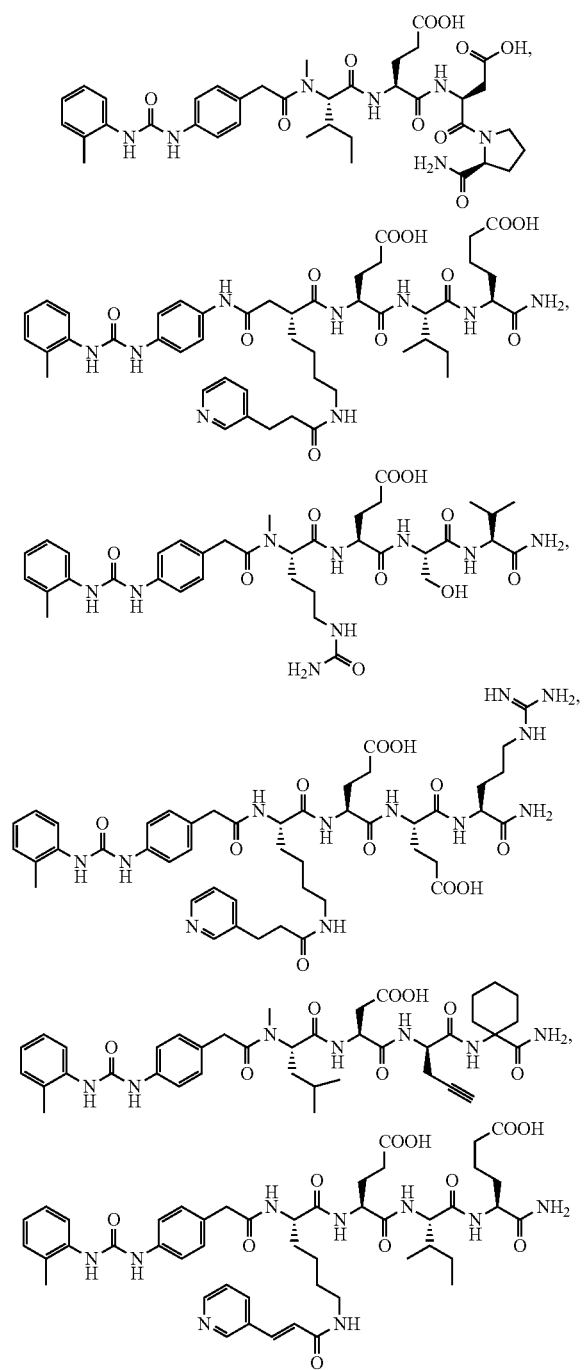

135
-continued
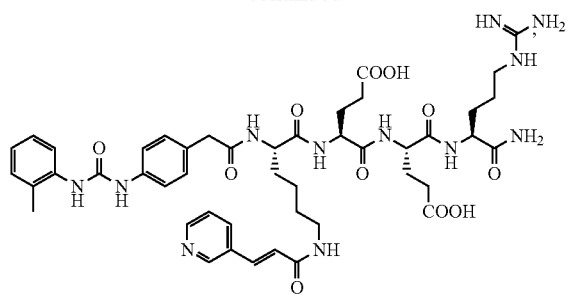
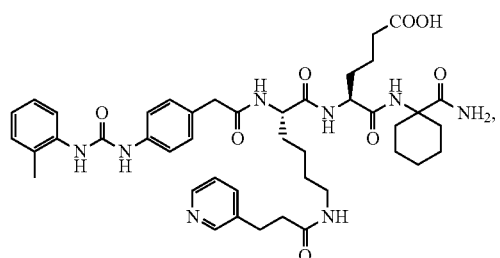
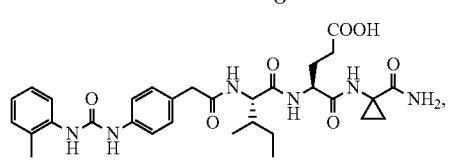
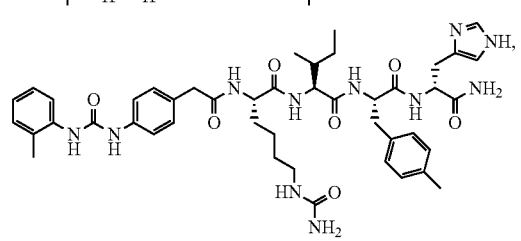
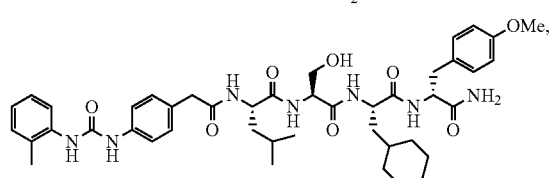
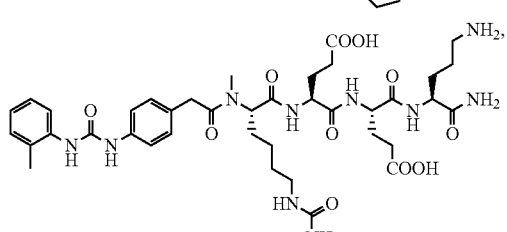
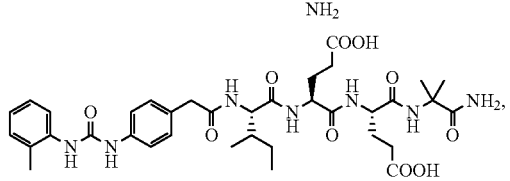
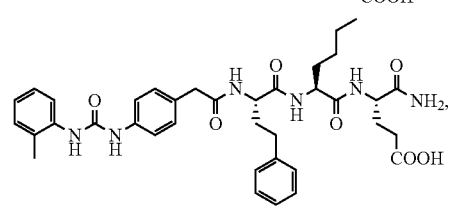
136
-continued
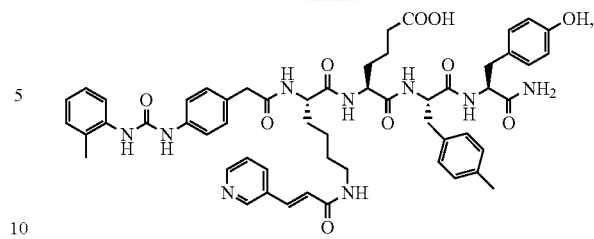
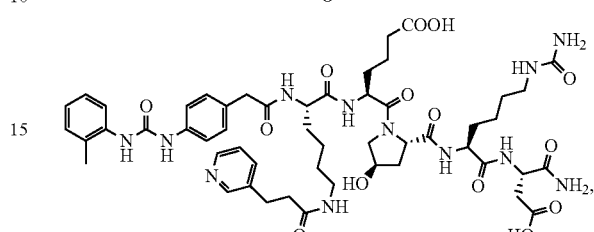
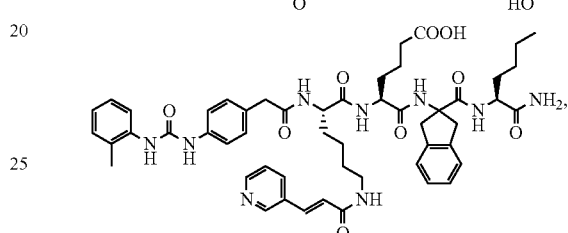
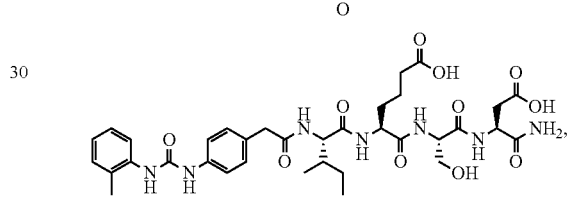
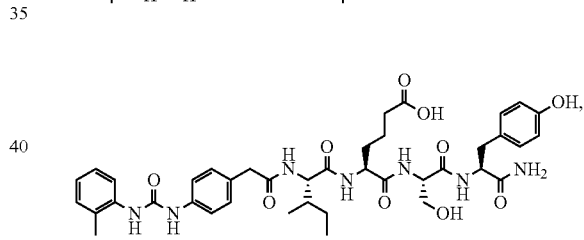
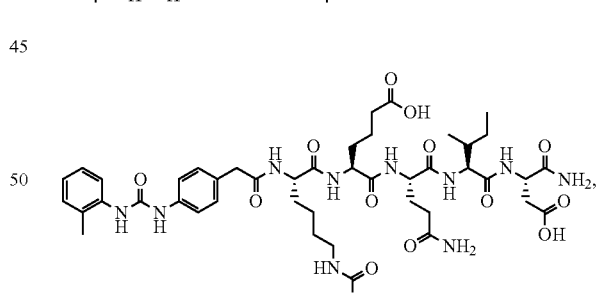
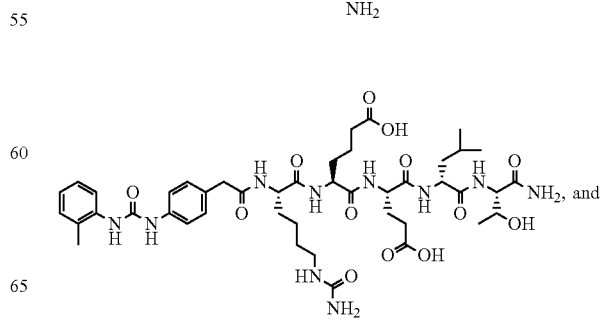

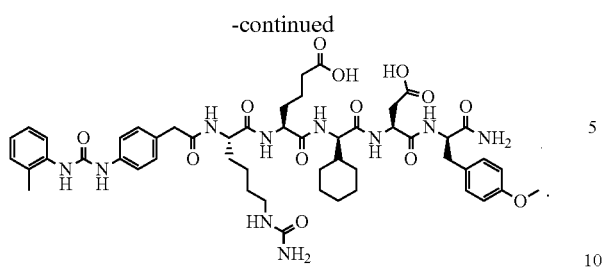

2. A pharmaceutical composition comprising a compound of claim 1, or a pharmaceutically acceptable salt thereof, and one or more pharmaceutically acceptable excipients.

3. A method of treating osteoporosis, comprising administering to a subject in need thereof, a therapeutically effective amount of a compound of claim 1.

4. A method of promoting bone growth, comprising administering to a subject in need thereof, a therapeutically effective amount of a compound of claim 1.

5. A method of treating low bone mass, comprising administering to a subject in need thereof, a therapeutically effective amount of a compound of claim 1.

6. A method of treating a disease or condition characterized by secondary low bone mass, comprising administering to a subject in need thereof, a therapeutically effective amount of a compound of claim 1.

7. The method of claim 3, wherein the therapeutically effective amount is an amount that activates Akt signaling in the subject.

* * * * *